(12) United States Patent
Formica et al.

(10) Patent No.: US 9,878,118 B2
(45) Date of Patent: Jan. 30, 2018

(54) HEADGEAR FOR MASKS

(71) Applicant: ResMed Limited, Bella Vista, New South Wales (AU)

(72) Inventors: Justin John Formica, Sydney (AU); Anthony Paul Barbara, Sydney (AU); Brent James Dravitzki, Sydney (AU); Philip John Gunning, Sydney (AU)

(73) Assignee: ResMed Limited, Bella Vista (AU)

( * ) Notice: Subject to any disclaimer, the term of this patent is extended or adjusted under 35 U.S.C. 154(b) by 207 days.

(21) Appl. No.: 14/601,316

(22) Filed: Jan. 21, 2015

(65) Prior Publication Data

US 2015/0128953 A1    May 14, 2015

Related U.S. Application Data

(63) Continuation of application No. 12/998,420, filed as application No. PCT/AU2009/001605 on Dec. 10, 2009, now Pat. No. 8,950,404.

(30) Foreign Application Priority Data

| Dec. 10, 2008 | (AU) | ................................ 2008906390 |
| Jan. 29, 2009 | (AU) | ................................ 2009900327 |

(Continued)

(51) Int. Cl.
*A61M 16/06* (2006.01)
*A61M 16/08* (2006.01)
*A62B 18/08* (2006.01)

(52) U.S. Cl.
CPC .... *A61M 16/0683* (2013.01); *A61M 16/0622* (2014.02); *A61M 16/0633* (2014.02);
(Continued)

(58) Field of Classification Search
CPC .......... A61M 16/0688; A61M 16/0622; A61M 16/0633; A61M 16/0683; A61M 16/0816; A62B 18/084
See application file for complete search history.

(56) References Cited

U.S. PATENT DOCUMENTS

| 1,942,442 A | 1/1934 | Motsinger |
| 2,016,210 A | 10/1935 | Mann |

(Continued)

FOREIGN PATENT DOCUMENTS

| CA | 2 671 591 | 6/2008 |
| CN | 1326371 A | 12/2001 |

(Continued)

OTHER PUBLICATIONS

Patent Examination Report No. 1 dated May 22, 2015 in Australian Appln. No. 2014201197 (3 pages).

(Continued)

*Primary Examiner* — Steven Douglas
*Assistant Examiner* — Kathrynn Lyddane
(74) *Attorney, Agent, or Firm* — Nixon & Vanderhye P.C.

(57) ABSTRACT

A headgear for use with a mask includes a first strap being configured to engage a back of a patient's head and extend on either side of the patient's parietal bone behind the patient's ears and assume, in use, a substantially circular or oval shape. At least a portion of the first strap is substantially inextensible. The headgear also includes at least one second strap configured to removably connect the first strap to the mask. The second strap may be more extensible than the first strap. At least a portion of the first strap is self-supporting such that the headgear maintains a three dimensional shape when not in use. The substantially inextensible portion of the first strap is constructed to resiliently return to a predetermined shape when not in use. The arcuate region includes a (Continued)

first portion that may be arranged to align substantially parallel with a top of the patient's head and a second portion being arranged to align substantially to a rear surface of the patient's head.

61 Claims, 35 Drawing Sheets

(30) Foreign Application Priority Data

Jun. 12, 2009 (AU) ................................ 2009902731
Sep. 4, 2009 (AU) ................................ 2009904236

(52) U.S. Cl.
CPC .... *A61M 16/0688* (2014.02); *A61M 16/0816* (2013.01); *A61M 2205/02* (2013.01); *A61M 2207/10* (2013.01); *A62B 18/084* (2013.01); *Y10T 156/1077* (2015.01)

(56) References Cited

U.S. PATENT DOCUMENTS

| | | | |
|---|---|---|---|
| 2,126,755 A | 8/1938 | Dreyfus | |
| 2,259,817 A | 10/1941 | Hawkins | |
| 2,353,643 A | 7/1944 | Bulbulian | |
| 2,783,474 A | 3/1957 | Campagna et al. | |
| 2,928,387 A | 3/1960 | Layne | |
| 3,013,556 A | 12/1961 | Galleher, Jr. | |
| 3,234,940 A | 2/1966 | Morton, Jr. | |
| 3,424,633 A * | 1/1969 | Corrigall | A41C 3/00 156/242 |
| 3,752,157 A | 8/1973 | Malmin | |
| 3,792,702 A | 2/1974 | Delest | |
| 4,018,221 A | 4/1977 | Rennie | |
| 4,164,942 A | 8/1979 | Beard et al. | |
| 4,367,735 A | 1/1983 | Dali | |
| 4,409,163 A | 10/1983 | Van Manen | |
| 4,581,773 A | 4/1986 | Cunnane | |
| 4,593,688 A | 6/1986 | Payton | |
| 4,665,566 A | 5/1987 | Garrow | |
| 4,675,919 A | 6/1987 | Heine et al. | |
| 4,695,501 A | 9/1987 | Robinson | |
| 4,744,358 A | 5/1988 | McGinnis | |
| 4,774,946 A | 10/1988 | Ackerman et al. | |
| 4,790,306 A | 12/1988 | Braun et al. | |
| 4,821,736 A | 4/1989 | Watson | |
| 4,856,116 A | 8/1989 | Sullivan | |
| 4,910,804 A | 3/1990 | Lidgren | |
| 4,947,488 A | 8/1990 | Ashinoff | |
| 5,265,595 A | 11/1993 | Rudolph | |
| 5,331,686 A | 7/1994 | Marshall | |
| 5,395,400 A | 3/1995 | Stafford et al. | |
| 5,416,924 A | 5/1995 | Sims | |
| 5,490,980 A | 2/1996 | Richardson et al. | |
| 5,517,986 A | 5/1996 | Starr | |
| 5,538,000 A | 7/1996 | Rudolph | |
| 5,542,128 A | 8/1996 | Lomas | |
| 5,566,395 A | 10/1996 | Nebeker | |
| 5,570,689 A | 11/1996 | Starr et al. | |
| 5,598,585 A | 2/1997 | Stroup | |
| 5,687,715 A | 11/1997 | Landis et al. | |
| 5,720,715 A | 2/1998 | Eriksson | |
| 5,724,677 A | 3/1998 | Bryant et al. | |
| 5,724,965 A | 3/1998 | Handke et al. | |
| 5,817,041 A | 10/1998 | Bader | |
| 5,829,062 A | 11/1998 | Magidson | |
| 5,903,921 A | 5/1999 | Dow | |
| 6,019,101 A | 2/2000 | Cotner et al. | |
| 6,062,221 A | 5/2000 | Brostrom et al. | |
| 6,119,694 A | 9/2000 | Correa et al. | |
| 6,189,151 B1 | 2/2001 | Curtis | |
| 6,205,590 B1 | 3/2001 | Gorman | |
| 6,269,814 B1 | 8/2001 | Blaszczykiewicz et al. | |
| 6,332,465 B1 | 12/2001 | Xue et al. | |
| 6,470,886 B1 | 10/2002 | Jestrabek-Hart | |
| 6,494,207 B1 | 12/2002 | Kwok | |
| 6,565,461 B1 | 5/2003 | Zatlin | |
| 6,610,032 B1 | 8/2003 | Prody | |
| 6,712,072 B1 | 3/2004 | Lang | |
| 6,739,427 B2 | 5/2004 | Gayetty | |
| 6,805,117 B1 | 10/2004 | Ho et al. | |
| 6,861,379 B1 | 3/2005 | Blaszczykiewicz | |
| 6,907,882 B2 | 6/2005 | Ging et al. | |
| 7,047,972 B2 | 5/2006 | Ging et al. | |
| 7,178,528 B2 | 2/2007 | Lau et al. | |
| 7,188,620 B2 * | 3/2007 | Amarasinghe | A61M 16/0683 128/201.22 |
| 7,210,481 B1 | 5/2007 | Lovell | |
| 7,219,670 B2 | 5/2007 | Jones, Jr. et al. | |
| 7,222,374 B2 | 5/2007 | Musal et al. | |
| 7,296,575 B1 * | 11/2007 | Radney | A61M 16/06 128/207.11 |
| 7,318,437 B2 | 1/2008 | Gunaratnam et al. | |
| 7,357,136 B2 | 4/2008 | Ho et al. | |
| 7,509,958 B2 | 3/2009 | Amarasinghe et al. | |
| 7,562,658 B2 * | 7/2009 | Madaus | A61M 16/06 128/201.22 |
| 7,827,990 B1 | 11/2010 | Melidis et al. | |
| 8,286,634 B2 | 10/2012 | Madaus et al. | |
| 8,356,602 B2 | 1/2013 | Crocetti | |
| 8,950,404 B2 | 2/2015 | Formica et al. | |
| 2002/0020416 A1 | 2/2002 | Namey | |
| 2002/0053750 A1 | 5/2002 | Schwaighofer | |
| 2003/0051732 A1 | 3/2003 | Smith et al. | |
| 2003/0056785 A1 | 3/2003 | Narihiko et al. | |
| 2003/0118808 A1 | 6/2003 | Canamero et al. | |
| 2003/0196655 A1 | 10/2003 | Ging et al. | |
| 2004/0025882 A1 | 2/2004 | Madaus et al. | |
| 2004/0065328 A1 | 4/2004 | Amarasinghe et al. | |
| 2004/0067333 A1 | 4/2004 | Amarasinghe | |
| 2004/0073989 A1 | 4/2004 | Horn | |
| 2004/0083534 A1 * | 5/2004 | Ruiz | A61F 5/56 2/171.2 |
| 2004/0112377 A1 | 6/2004 | Amarasinghe et al. | |
| 2004/0149280 A1 | 8/2004 | Semeniuk | |
| 2005/0039753 A1 | 2/2005 | Schumacher | |
| 2006/0000476 A1 | 1/2006 | Salem | |
| 2006/0081250 A1 | 4/2006 | Bordewick et al. | |
| 2006/0081252 A1 * | 4/2006 | Wood | A61M 16/0683 128/207.11 |
| 2006/0096911 A1 | 5/2006 | Brey et al. | |
| 2006/0118117 A1 | 6/2006 | Berthon-Jones et al. | |
| 2006/0118119 A1 | 6/2006 | Berthon-Jones et al. | |
| 2007/0017525 A1 | 1/2007 | Madaus et al. | |
| 2007/0130663 A1 | 6/2007 | Lang et al. | |
| 2007/0181135 A1 | 8/2007 | Baker | |
| 2007/0186931 A1 | 8/2007 | Zollinger et al. | |
| 2007/0209663 A1 | 9/2007 | Marque et al. | |
| 2007/0264462 A1 | 11/2007 | Covelli et al. | |
| 2008/0011305 A1 | 1/2008 | Chandran et al. | |
| 2008/0041390 A1 | 2/2008 | Radney | |
| 2008/0047560 A1 | 2/2008 | Veliss et al. | |
| 2008/0060648 A1 | 3/2008 | Thornton et al. | |
| 2008/0060745 A1 | 3/2008 | Lau | |
| 2008/0142015 A1 | 6/2008 | Groll | |
| 2009/0044808 A1 | 2/2009 | Guney et al. | |
| 2009/0107514 A1 | 4/2009 | Winningham | |
| 2010/0000544 A1 * | 1/2010 | Blaszczykiewicz | A61F 5/56 128/207.17 |
| 2011/0072553 A1 | 3/2011 | Ho | |
| 2011/0197341 A1 | 8/2011 | Formica et al. | |
| 2011/0253143 A1 | 10/2011 | Ho et al. | |
| 2012/0145157 A1 | 6/2012 | Lang et al. | |
| 2013/0000648 A1 | 1/2013 | Madaus et al. | |

FOREIGN PATENT DOCUMENTS

| | | |
|---|---|---|
| CN | 1408453 A | 4/2003 |
| CN | 1642471 A | 7/2005 |
| CN | 1684733 A | 10/2005 |
| CN | 1711059 A | 12/2005 |

(56) References Cited

FOREIGN PATENT DOCUMENTS

| | | |
|---|---|---|
| CN | 1711060 A | 12/2005 |
| CN | 1750853 A | 3/2006 |
| CN | 1997572 A | 7/2007 |
| CN | 101143029 A | 3/2008 |
| CN | 101237902 A | 8/2008 |
| DE | 196 25 337 A1 | 1/1998 |
| DE | 198 07 961 A1 | 8/1999 |
| DE | 299 23 126 U1 | 5/2000 |
| DE | 100 35 946 A1 | 2/2002 |
| DE | 10254399 | 6/2004 |
| EP | 0 958 841 A2 | 11/1999 |
| EP | 1 020 201 A2 | 7/2000 |
| EP | 1057494 | 12/2000 |
| EP | 1 356 843 A2 | 10/2003 |
| EP | 2 373 368 B1 | 3/2016 |
| FR | 2 658 725 A1 | 8/1991 |
| JP | 55-16140 | 7/1978 |
| JP | 8-57055 A | 3/1996 |
| JP | H10-25613 | 1/1998 |
| JP | 2000-102624 A | 4/2000 |
| JP | 2000-135103 A | 5/2000 |
| JP | 2000-254229 A | 9/2000 |
| JP | 2004-571 A | 1/2004 |
| JP | 2004-137635 A | 5/2004 |
| JP | 3602117 | 10/2004 |
| JP | 2004-351040 A | 12/2004 |
| JP | 2005-534383 | 11/2005 |
| JP | 2006-505373 | 2/2006 |
| JP | 2008-502380 A | 1/2008 |
| JP | 5701770 B2 | 4/2015 |
| WO | WO 99/65554 A1 | 12/1999 |
| WO | WO 00/50122 A1 | 8/2000 |
| WO | WO 00/74758 A1 | 12/2000 |
| WO | WO 01/62326 A1 | 8/2001 |
| WO | WO 02/07806 | 1/2002 |
| WO | WO 02/47749 A1 | 6/2002 |
| WO | WO 2004/012803 | 2/2004 |
| WO | WO 2004/041341 | 5/2004 |
| WO | WO 2004/041342 | 5/2004 |
| WO | WO 2005/028010 | 3/2005 |
| WO | WO 2005/032634 | 4/2005 |
| WO | WO 2005/039680 | 5/2005 |
| WO | WO 2005/076874 | 8/2005 |
| WO | WO 2005/079726 | 9/2005 |
| WO | WO 2006/044120 | 4/2006 |
| WO | WO 2006/072128 A1 | 7/2006 |
| WO | WO 2006/127031 | 11/2006 |
| WO | WO 2006/130903 | 12/2006 |
| WO | WO 2006/133012 | 12/2006 |
| WO | WO 2006/138334 | 12/2006 |
| WO | WO 2007/006089 A1 | 1/2007 |
| WO | WO 2007/026063 A1 | 3/2007 |
| WO | WO 2007/147088 | 12/2007 |
| WO | WO 2008/007985 | 1/2008 |
| WO | WO 2008/030831 | 3/2008 |
| WO | WO 2008/068966 | 6/2008 |
| WO | WO 2009/026627 A1 | 3/2009 |
| WO | WO 2009/052560 | 4/2009 |
| WO | WO 2009/059353 | 5/2009 |
| WO | WO 2009/148956 | 12/2009 |
| WO | WO 2010/066004 A1 | 6/2010 |

OTHER PUBLICATIONS

Patent Examination Report No. 2 dated Sep. 16, 2015 in Australian Appln. No. 2014201197 (2 pages).
Further Examination Report dated Jul. 20, 2015 in New Zealand Appln. No. 706870 (2 pages).
Extension of Time Granted dated Sep. 30, 2015 in New Zealand Appln. No. 616559 (1 page), together with Notice of Opposition to Grant of Patent (2 pages) and Application Under Regulation 168 for Extension of Time (1 page).
Notification of Reexamination dated Dec. 7, 2015 in Chinese Application No. 200980149789.4 with English translation (20 pages).
Notice of Reasons for Rejection dated Nov. 30, 2015 in Japanese Application No. 2015-021033 with English translation (4 pages).
Decision of Commissioner dated Sep. 15, 2015 in New Zealand Application No. 610179 (10 pages).
Further Examination Report dated Feb. 23, 2016 in New Zealand Application No. 706870 (2 pages).
Notification of Reexamination dated May 11, 2016 in Chinese Application No. 200980149789.4, with English translation (20 pages).
Notification of the First Office Action dated May 18, 2016 in Chinese Application No. 201510026138.3, with English translation (20 pages).
Patent Examination Report No. 1 dated Nov. 28, 2016 in Australian Application No. 2016201534 (2 pages).
Turbocast 3M. Datenblatt. URL: http://www.servoprax.de/shop/unserangebot/medical-products/verbandmittel/schienen-und-orthesen/turbocast-3m (downloaded Oct. 18, 2016), including English version of page from website downloaded Dec. 1, 2016 (2 pages).
Turbocast—Niedertemperatur—Thermoplast, data sheet; URL: http://www.orthopaedie-bedarf.com/rel/pages/produkte/produkte_a_z/turbocast.php?id=03,01,07, downloaded Dec. 1, 2016 (1 page).
Petition for Inter Partes Review of U.S. Pat. No. 8,950,404, Case No. 2017-00340, *Fisher & Paykel Healthcare Limited, Petitioner* v. *ResMed Limited*, Patent Owner, filed Nov. 28, 2016 (102 pages).
Australian Provisional Application No. 2008906390, filed Dec. 10, 2008, for "Headgear for a Mask," IPR Exhibit 1007, (30 pages).
Australian Provisional Application No. 2009900327, filed Jan. 29, 2009, for "Headgear for Masks" IPR Exhibit 1008, (42 pages).
Australian Provisional Application No. 2009902731, filed Jun. 12, 2009, for "Headgear for Masks," IPR Exhibit 1009, (57 pages).
Australian Provisional Application No. 2009904236, filed Sep. 4, 2009, for "Headgear for Masks," IPR Exhibit 1010, (61 pages).
U.S. Appl. No. 60/842,741, filed Sep. 7, 2006, for "Headgear Assembly," IPR Exhibit 1011, (34 pages).
Declaration of Richard Lordo, P.E., in Support of Petition for Inter Partes Review of U.S. Pat. No. 8,950,404, executed Nov. 28, 2016, IPR Exhibit 1013, (214 pages).
Curriculum Vitae Richard J Lordo, PE, IPR Exhibit 1014, 4 pages.
Excerpts from the File History of U.S. Pat. No. 8,950,404, U.S. Appl. No. 12/998,420, IPR Exhibit 1015, (666 pages).
Answer of ResMed Corp. to Complaint for Patent Infringement and Counterclaims, *Fisher & Paykel Healthcare Ltd.* v. *ResMed Corp.*, Case No. 3:16-cv-02068-DMS-WVG (S.D. Cal.), IPR Exhibit 1016, (94 pages).
Proceeding Correspondence dated Sep. 28, 2016 by NZ Intellectual Property Office in NZ 616559 (2 pages).
AJ Park filing of Sep. 30, 2016 in NZ 616559 (2 pages).
Proceeding Correspondence dated Oct. 18, 2016 by NZ Intellectual Property Office in NZ 616559 (1 page).
Proceeding Correspondence dated Nov. 8, 2016 by NZ Intellectual Property Office in NZ 616559 (2 pages).
Proceeding Correspondence dated Dec. 15, 2016 by NZ Intellectual Property Office in NZ 616559 (1 page).
Decision of Reexamination dated Nov. 14, 2016 in Chinese Application No. 200980149789.4, with English translation (57 pages).
International Search Report issued in PCT/AU2009/001605 (dated Mar. 23, 2010), 6 pages.
Written Opinion of the International Preliminary Examining Authority issued in PCT/AU2009/001605 (dated Mar. 23, 2010), 9 pages.
Written Opinion of the International Preliminary Examining Authority issued in PCT/AU2009/001605 (dated Jan. 27, 2011), 13 pages.
International Preliminary Report on Patentability in PCT/AU2009/001605 (dated Oct. 7, 2010), 22 pages.
Patent Examination Report No. 1 issued in a related Australian Patent Appl. No. 2009326861 dated Jun. 25, 2012.
Examination Report issued in a related New Zealand Application No. 592064, dated Jul. 18, 2012.

(56) References Cited

OTHER PUBLICATIONS

Office Action issued in corresponding Japanese Application No. 2011-539848, dated Oct. 15, 2013, with English language translation thereof.
First Examination Report issued in a corresponding New Zealand Application No. 616559 dated Oct. 21, 2013.
Further Examination Report issued in a corresponding New Zealand Application No. 592064 dated Oct. 25, 2013.
Office Action issued in a corresponding Chinese Application No. 200980149789.4 dated Jan. 6, 2014, with English language translation thereof.
Office Action issued in corresponding Japanese Appln. No. 2011-539848 dated Mar. 17, 2014, with English translation thereof.
ResMed "Modular Mask System", 2 pages, before Apr. 19, 2010.
ResCare "Clinical Equipment (continued)", 2 pages, before Apr. 19, 2010.
ResMed "The Resmed Range of Mask Systems", 4 pages, before Apr. 19, 2010.
ResMed "Disposable Mask Systems", 4 pages, before Apr. 19, 2010.
Invitation Pursuant to Rule 63(1) EPC dated Jul. 3, 2014 in European Application No. 09 831 318.2 (3 pages).
Extended European Search Report dated Nov. 5, 2014 in European Application No. 09831318.2 (7 pages).
Extended European Search Report dated Aug. 19, 2016 in European Application No. 16159937.8 (8 pages).
Communication of a Notice of Opposition dated Jan. 5, 2017 in European Application No. 09831318.2 (EP Patent No. 2373368), with Opposition filed by Fisher & Paykel Healthcare GmbH, 60 pages.
Exhibit N1 from Opposition filed in EP Patent No. 2337368, "extract from the infringement action filed by the patentee against the opponent," dated Aug. 23, 2016, 3 pages.
Exhibit N4 from Opposition filed in EP Patent No. 2337368, "feature analysis of claim 1 of the opposed patent," 1 page.
Exhibit D1a from Opposition filed in EP Patent No. 2337368, "Declaration of Conformity—European Union OSA Masks," 4 pages.
Exhibit D1b from Opposition filed in EP Patent No. 2337368, "Declaration of Christopher Earl Nightingale dated Dec. 15, 2016," 8 pages.
Exhibit D1c from Opposition filed in EP Patent No. 2337368, design drawing of the headgear for the FlexiFit 431 Mask dated May 11, 2006 (Revision D), 1 page.
Exhibit D1d from Opposition filed in EP Patent No. 2337368, design drawings of the headgear for the FlexiFit 431 mask dated Oct. 27, 2009 (Revision E), 1 pages.
Exhibit D1e from Opposition filed in EP Patent No. 2337368, Declaration of Olivia Allan dated Dec. 15, 2016, 10 pages.
Exhibit D1f from Opposition filed in EP Patent No. 2337368, Invoices 1 to 3 for the FlexiFit 431 Mask (redacted), 4 pages.
Notification of the Second Office Action dated Feb. 4, 2017 in Chinese Application No. 201510026138.3, with English translation, 18 pages.
Notices of Reasons for Rejection dated Jan. 16, 2017 in Japanese Application No. P2016-036831, with English translation, 7 pages.
Notice of Opposition to Grant of Patent (Section 21) filed by Fisher & Paykel Healthcare Limited dated Mar. 24, 2017 with Application Under Regulation 168 for Extension of Time in New Zealand Application No. NZ 706870 (3 pages).
Notification of the First Office Action dated Mar. 31, 2017 in Chinese Application No. 201510475702.X with English translation (13 pages).
Decision Institution of Inter Partes Review entered May 16, 2017 in IPR2017-00340 of U.S. Pat. No. 8,950,404 (54 pages).
Scheduling Order Under 37 C.F.R. §42.5 entered May 16, 2017 in IPR2017-00340 of U.S. Pat. No. 8,950,404 (10 pages).
Second Notice of Opposition to Grant of Patent filed Jun. 8, 2017 in New Zealand Application No. 706870 (2 pages).
Statement of Case filed Jun. 8, 2017 in New Zealand Application No. 706870 (25 pages).
Petition for Inter Partes Review of U.S. Pat. No. 8,950,404, IPR2017-01905, filed Aug. 2, 2017 (106 pages).
Declaration of Richard Lordo, P.E. in Support of Petition for Inter Partes Review of U.S. Pat. No. 8,950,404, Case. No. IPR2017-01905, executed Aug. 1, 2017 (379 pages).
Notification of the Third Office Action dated Aug. 16, 2017 in Chinese Application No. 201510026138.3, with English translation (16 pages).

* cited by examiner

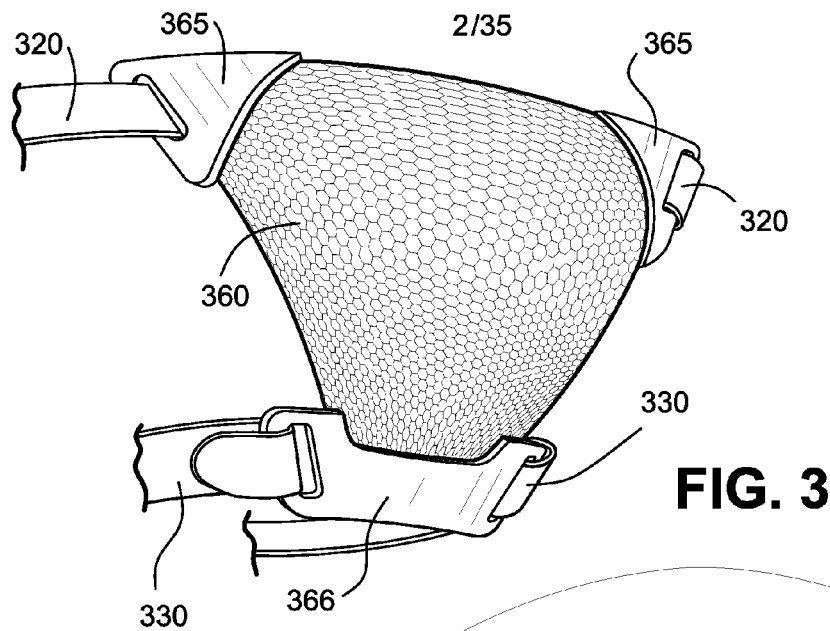
FIG. 3
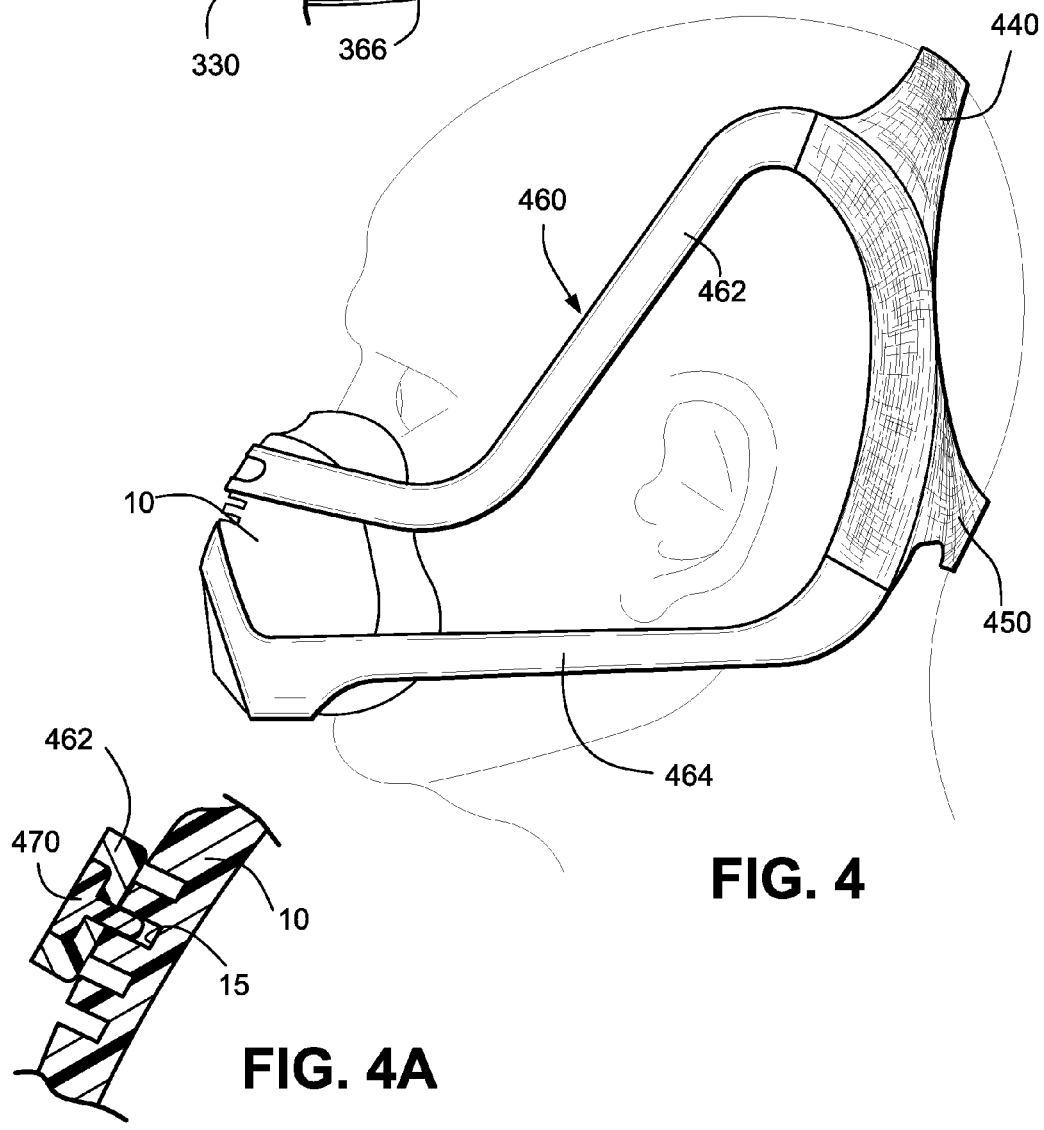
FIG. 4
FIG. 4A

HEADGEAR FOR MASKS

CROSS-REFERENCE TO RELATED APPLICATIONS

This application is a continuation of U.S. application Ser. No. 12/998,420, filed Apr. 19, 2011, which is the U.S. national phase of International Application No. PCT/AU2009/001605, filed Dec. 10, 2009, which designated the U.S. and claims the benefit of Australian Provisional Application Nos. AU 2008906390, filed Dec. 10, 2008, AU 2009900327, filed Jan. 29, 2009, AU 2009902731, filed Jun. 12, 2009, and AU 2009904236, filed Sep. 4, 2009, each of which is incorporated herein by reference in its entirety.

FIELD OF THE INVENTION

The present invention relates to headgear and a method of manufacturing the headgear for use in holding a mask in position on a patient's face, the mask being used for treatment, e.g., of Sleep Disordered Breathing (SDB) with Continuous Positive Airway Pressure (CPAP) or Non-Invasive Positive Pressure Ventilation (NIPPY).

BACKGROUND OF THE INVENTION

Masks used for treatment of SDB such as OSA are typically held on a patient's head by headgear. Headgear typically includes one or more headgear straps that are adapted to engage with the mask and hold the mask in position on the patient's face. In addition, headgear should be comfortable so that a patient can wear the mask at night while they sleep. There is a continuous need in the art for headgear that is comfortable, fits a wide range of patients, is easily manufactured, and is inexpensive.

A problem with some prior art headgear is that a given size may fit very few patients, or alternatively that they may require a large number of adjustments to fit. Another problem with some prior art headgear is that they have a tendency to leave facial marks in use. Another problem with some prior art headgear is that they are awkward and complicated to use.

SUMMARY OF THE INVENTION

A first aspect of the present technology is to provide headgear for a respiratory mask.

Another aspect of the present technology is to provide headgear that comfortably fits a wide range of patients. Another aspect of the present technology is to provide a lower cost method of manufacturing headgear for a respiratory mask. Another aspect of the present technology is to provide a headgear that is easy to use.

One aspect of a headgear in accordance with the present technology is that a rear portion of the headgear is constructed and arranged to remain relatively fixed in position in use. In one form, the headgear comprises a rear portion that does not substantially "ride" or slide forward. Another aspect that a preferred headgear does not impinge on the ears when in use.

In one form the rear portion of the headgear defines a rear loop that circumscribes the rear of the head. In one form the rear portion comprises a rear loop that is substantially inextensible along its length. In one form of the present technology headgear for a respiratory mask is provided having a first region with a first extensibility and at least one further region with a different extensibility. In one form the headgear comprises a generally inextensible rear portion and an elastic side portion.

One aspect of the present technology relates to headgear for use with a mask and may include a rigidizer constructed of a rigid or semi-rigid material and adapted to extend on either side of the patient's parietal bone, an upper strap adapted to removably connect the rigidizer to an upper portion of the mask, and a lower strap adapted to removably connect the rigidizer to a lower portion of the mask.

Another aspect of the present technology relates to headgear for use with a mask including a rigidizer constructed of a rigid or semi-rigid material and adapted to extend along the patient's parietal and zygomatic bones, and one or more straps adapted to support the rigidizer at the back of the patient's head.

Another aspect of the present technology relates to headgear comprising a relatively inextensible rear portion and a plurality of relatively extensible straps. Preferably in use the relatively extensible straps interconnect the rear portion and a mask.

Another aspect of the present headgear technology is a relatively low cost manufacturing technique.

Another aspect of the present technology relates to method of constructing headgear comprising the step of die cutting relatively straight portions from a sheet of material. Another aspect of the present technology relates to a high yield layout of headgear strap components in a sheet.

Another aspect of the present technology may include a method of manufacturing headgear for use with a mask, wherein the headgear comprises components that are generally simple geometric shapes and capable of being cut from a flat piece of material, wherein the method includes: a) cutting multiple components of the same type from a single flat sheet of said material; b) components are nested against each other on said sheet to minimize the amount of waste material that is removed and discarded; and c) wherein the method produces a high manufacturing yield. Preferably, the high manufacturing yield is defined by being greater than 11.5 headgears per meter$^2$ and the shapes may include: generally rectangular or arcuate shapes.

Preferably, the shapes may include: generally rectangular or arcuate shapes; and the components may include: straps or rigidizers.

Another aspect of the present technology may include a headgear assembly for use to attach medical equipment to a patient's head, wherein the headgear comprises: a plurality of elongated straps, wherein at least a portion of said straps includes a rigid or semi-rigid layer encapsulated between a first and second layer of flexible biocompatible material; and further wherein a cushioning layer is also encapsulated between the first layer of material and the rigid layer. Preferably, the layers of the straps are fixed by vulcanization or gluing and the straps may include the rigid layer are positioned to the posterior of the head, when in use. Preferably, the material is fabric.

Another aspect of a headgear in accordance with the present technology is that it has a lesser tendency to produce facial marks when compared to prior art. In one form, headgear in accordance with the present technology has softened edges. In one form, joins are located away from contact with the face. In one form, large radius edges are used. In one form, die cut edges are not presented to the face in use.

Another aspect of the present technology may include a process for making headgear including laminating foam and fabric material to one another, thermoforming the laminated foam and fabric material, ultrasonically die cutting the thermoformed and laminated foam and fabric material into one or more strap portions of the headgear, and joining the one or more strap portions to one another.

Another aspect of a preferred headgear in accordance with the present technology is that it is constructed and arranged to assume a predetermined shape when not in use. The predetermined shape may be substantially similar to the shape the headgear assumes when being worn, making the headgear intuitively easier to use. In one form, headgear in accordance with the present technology is constructed and arranged to "spring to life" and assume the predetermined shape when removed from packaging and/or when a force (e.g. compression) tending to deform the headgear is removed. In one form the headgear comprises a portion constructed from a resilient material. In one form the headgear comprises a self-supporting rear portion.

A further aspect of the present technology relates to a headgear for use with a mask comprising a rigidizer; a conformable material; and at least one fabric, wherein edges of the at least one fabric are sealed by at least one joint so that the rigidizer, the conformable material, and the at least one joint are encapsulated by the at least one fabric over at least a portion of the headgear.

A still further aspect of the present technology relates to a headgear for use with a mask comprising a first strap being configured to engage a back of a patient's head and extend on either side of the patient's parietal bone behind the patient's ears and assume, in use, a substantially circular or oval shape, wherein at least a portion of the first strap is substantially inextensible; and at least one second strap configured to removably connect the first strap to the mask.

Another aspect of the present technology relates to a headgear for use with a mask comprising a first strap being configured to extend over the crown of a patient's head and extend on either side of the patient's parietal bone and behind the patient's ears in use; and at least one second strap configured to removably connect the first strap to the mask, wherein at least a portion of the first strap is self-supporting such that the headgear maintains a three dimensional shape when not in use.

An even further aspect of the present technology relates to a headgear for holding a respiratory mask in position on a face of a patient comprising a rear portion; and respective left and right side portions adapted for connection with the respiratory mask, wherein the rear portion comprises a substantially inextensible arcuate region constructed to resiliently return to a predetermined shape when not in use, the arcuate region including a first portion being arranged to align substantially parallel with a top of the patient's head and a second portion being arranged to align substantially to a rear surface of the patient's head.

Yet another aspect of the present technology relates to a method of manufacturing a headgear for use with a mask comprising placing a rigidizer over a first foam and first fabric lamination; placing a second foam over the rigidizer and a second fabric over the second foam; thermoforming the first foam and the first fabric lamination, the rigidizer, the second foam, and the second fabric to form a thermoformed sheet; and ultrasonically cutting the thermoformed sheet around a perimeter of the headgear.

Another aspect of the present technology is to provide one size of headgear that fits a wide range of patients, reducing or eliminating the need to make adjustments to headgear to achieve a fit. In one form of the present technology, a rear portion of headgear is provided having a fixed size that does not require adjustment to fit a wide range of patients.

Other aspects, features, and advantages of this technology will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this technology. In such drawings:

FIG. 3 is a partial perspective view of headgear according to another embodiment of the present technology;

FIG. 4 is a side view of headgear in position on a patient's head according to another embodiment of the present technology;

FIG. 4A is a cross-sectional view showing attachment of the headgear of FIG. 4 to a mask according to an embodiment of the present technology;

DETAILED DESCRIPTION OF ILLUSTRATED EMBODIMENTS

Figure 1:
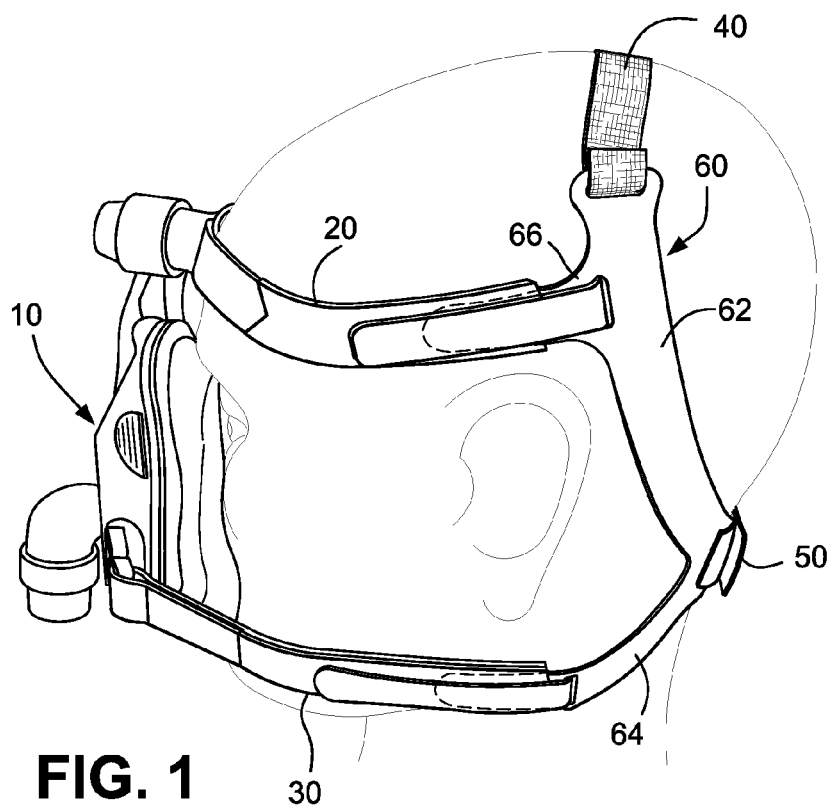
FIG. 1 is a side view of headgear in position on a patient's head according to an embodiment of the present technology.

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear. "Rigidizer" means and includes any reinforcing element that increases the rigidity of an another item and may include an object that increases rigidity in one or more axes.

In this specification, a substantially "inextensible" structure will be taken to mean a structure that when subject to the forces normally encountered in use of a respiratory mask, will have an elongation of less than about 5%, more preferably less than about 3%.

In this specification a "self-supporting" structure will be taken to mean a structure that can substantially support its own weight under the force of gravity. Such a self-supporting structure will be contrasted with a "floppy" structure that is unable to support its own weight under gravity.

In this specification a "rigid" structure is intended to mean a structure relatively more rigid than a "floppy" structure, such as the fabrics typically used as headgear. Such fabrics are typically unable to hold a predefined shape under gravity. A rigid structure may be able to redirect vectors around physical structures such as ears, unlike a floppy fabric that may bend or buckle.

1. Headgear

The figures illustrate headgear according to alternative embodiments of the present technology. In the illustrated embodiments, headgear are adapted to be removably attached to a mask to hold and maintain the mask in a desired position on a patient's face. While headgear may be illustrated as being used with a particular type of mask, it should be appreciated that each headgear may be adapted for use with other suitable masks. That is, the masks are merely exemplary, and each headgear embodiment may be adapted for use with any suitable mask, e.g., full-face mask, nasal mask, mouth mask, nozzles or puffs, nasal prongs, etc, with any suitable configuration, e.g., with or without forehead support.

Also, it should be appreciated that the headgear may be used with a new mask or the headgear may be retrofit to an existing mask.

In embodiments, the headgear arrangement, material, and/or adjustability may be designed to enhance usability, maintenance, comfort, and/or aesthetics. Also, the headgear arrangement, materials, and/or adjustability may be designed to enhance the range of fit, e.g., one size fits all.

An advantage of a headgear in accordance with the present technology is that it is relatively self-supporting and/or able to hold its shape without being worn. This can make it more intuitive or obvious for patients to understand how to use the headgear and may contrast with headgear systems that are entirely floppy and do not retain their shape. In one form the self-supporting aspect of the headgear is provided by the use of stiffened and/or thickened elements. In another embodiment, the headgear arrangement, material, and/or adjustability may be designed so that e.g., headgear springs out of the box and generally into its in-use configuration. In addition, the headgear arrangement may hold its in use shape once out of the box, for example a rigidizer may be formed to maintain the shape of some or part of the headgear.

Advantages to the patient of the present technology may include (but are not limited to) one or more of the following: a comfortable headgear system, a perceived level of comfort and quality, a smooth continuous headgear shape that is appealing to the consumer, a pillow-like appearance of the headgear that is soft to touch and comfortable to wear, and/or headgear that is pre-formed in the shape it is intended to be worn and is able to support itself in this shape such that the orientation of the headgear is clear. The orientation of the headgear is clear to the patient as the shape of the headgear is generally curved much like the rear portion of the patient's head. That is, the headgear is generally dome shaped.

In addition, the headgear is able to maintain its shape due to the manufacturing processes employed to construct the headgear and/or the combination of materials it comprises.

Another aspect of the headgear described herein is to direct the mask system to direct contact with the patient's face, that is, the vector of the headgear may cause the mask to apply pressure perpendicular or normal to the patient's face.

The headgear may further avoid contacting or obstructing the patient's eyes and ears.

The headgear may also be arranged such that it may fit a wider range of patients with only one size.

1.1 Headgear Attachment to Mask

Preferably, each headgear includes two side portions with a rear portion connecting the side portions. The side portions provide a four-point attachment with a mask which is consistent with prior headgear, e.g., allows headgear to be retrofit. However, it should be appreciated that the headgear may be structured to provide more or fewer attachment points, e.g., 2 point attachment with a mask, 3 point attachment with the mask, 5 point attachment with the mask.

In addition, the headgear may be constructed and arranged to provide force vectors at the mask which are consistent with prior headgear. For example, the headgear may be arranged such that the force vectors applied by the headgear to the mask are substantially perpendicular to the mask and substantially parallel to one another (e.g., see FIG. 1). This arrangement enhances the mask seal as the headgear forces the mask directly into the patient's face. However, adjustment of the headgear vectors may be necessary, e.g., depending on the type of mask used with the headgear.

1.2 Rigidizers

The headgear may include one or more rigidizers constructed of a rigid or semi-rigid material that are structured to add rigidity to the headgear and anchor the headgear in position in use. Rigidizer may be able to bend or deform along its length but resist or prevent stretching of the headgear in the lengthwise direction of the rigidizer. The rigidizers may be substantially inextensible. The rigidizer may be resilient. A rigidizer in accordance with the present technology preferably has one or more of the following features:

holds it shape;
allows headgear to redirect seal-force vectors around curves such as around the eyes, or around the ears;
ability to flex; and/or
in certain planes provides a structure to maintain a pre-defined form.

1.2.1 Rigidizer Positioning

The one or more rigidizers may be configured and positioned to engage alternative regions of the patient's head, e.g., for comfort, aesthetics, usability, etc.

The preferred positioning on the patient head is for the rigidizer to engage the posterior portion of the patient's skull or head. Additionally, it is advantageous not to cover the posterior portion of the patient's head to promote comfort whilst the patient is sleeping or in a prone position. Preferably, the rigidizer partially or fully surrounds or encompasses the parietal and/or occipital regions of the patient's skull. This rigidizer is preferably mounted in an axis that is approximately parallel to the orientation of the mask on the patient's face, when the headgear and mask combination are worn.

1.2.1.1 Parietal Rigidizer

Figure 2:
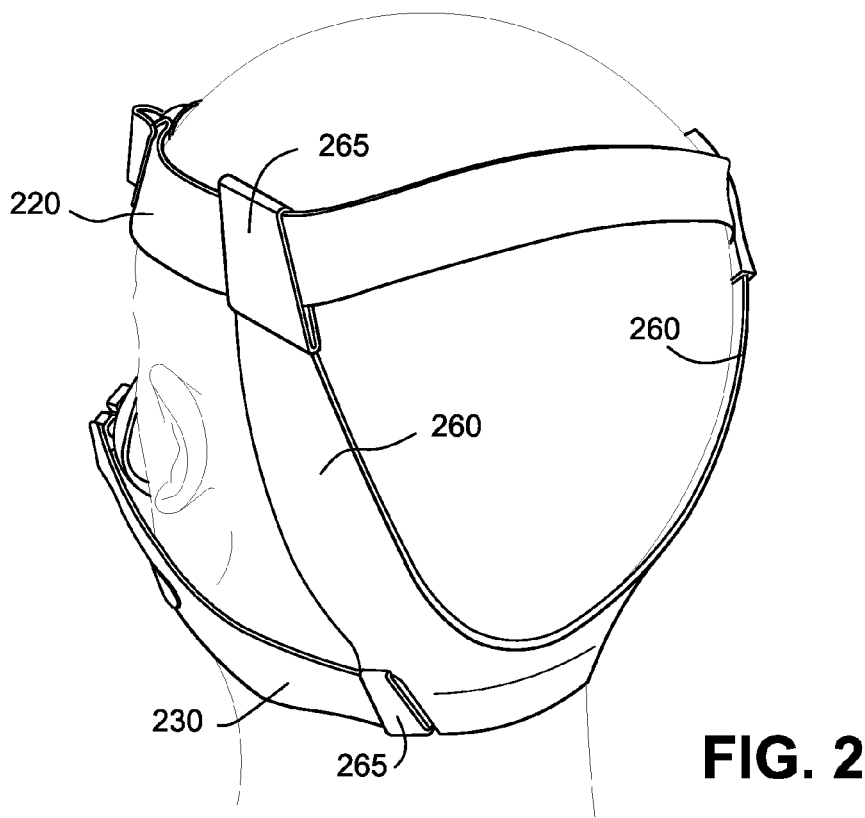
FIG. 2 is a rear perspective view of headgear in position on a patient's head according to another embodiment of the present technology.

FIGS. 1-3 illustrate headgear including rigidizers structured to conform to either side in a substantially vertical orientation on the patient's parietal bone to anchor the headgear in position.

Preferably, the rigidizer is relatively not elastic nor extendible along its length and is generally comprised of material that is resilient in nature.

In FIG. 1, a rigidizer 60 is provided on each side of the patient's head with each rigidizer 60 including an elongated main body 62, a lower arm 64 extending generally transverse from a lower end of the main body, and an upper arm 66 extending generally transverse and spaced downwardly from an upper end of the main body. An upper side strap 20 removably connects an upper portion of the mask 10 (e.g., via forehead support) to the upper arm 66, a lower side strap 30 removably connects a lower portion of the mask 10 (e.g., via headgear clip associated with clip receptacle) to the lower arm 64, a top strap 40 (e.g., elastic joining member) is adapted to pass over the top of the patient's head in use and interconnect the upper ends of opposing rigidizers 60, and a rear strap 50 is adapted to pass behind the patient's head in use and interconnect the lower ends of opposing rigidizers 60.

In an embodiment, the upper side strap 20 could be a single piece extending across the patient's forehead from one upper arm 66 to the opposing upper arm 66 on the other side of the patient's head. Preferably, the upper side strap 20 does not extend rearwardly significantly past the patient's ears. Also, FIG. 1 illustrates in dashed lines a potential extent of the upper and lower arms 66, 64. In an alternative embodiment, the upper arm 66 may be a single piece structured to extend across the patient's forehead from one main body 62 to the opposing main body 62 on the other side of the patient's head.

In FIG. 2, each rigidizer 260 has a composite construction (as described below) and is arranged such that the upper and lower side straps 220, 230 are continuous and extend from upper and lower portions of the mask, and through respective rigidizers 260, which rigidizers 260 extend along the parietal bone of the patient's head.

In an embodiment, each of the upper side straps 220, lower side straps 230 and rigidizer 260 may have different elastic properties so as to allow adjustability and stability to the mask on the patient's face in use.

In an example, the upper side strap 220 may be constructed from an extensible material to allow for adjustment of the mask when in use. For example, the upper side strap 220 may be made from elastic. Furthermore, the extensibility provided by the upper strap may allow for a greater fit range of patients. Additionally, the lower side straps 230 may be made from a material with lower extensibility than that of the upper side strap. That is, the lower side straps 230 may be constructed of a material with less stretch for a given force when compared to the material used for upper side strap 220. This is to secure the mask in position while allowing for some adjustment of the mask position on the face of the patient. Furthermore, the rigidizers 260 may be less extensible and less elastic than upper side strap 220 and/or lower side strap 230 so as to provide structure and support to the headgear and thus adequately anchor the mask to the patient's head in use.

Upper side straps 220 and/or lower side straps 230 may be constructed from a composite material such as Breath-O-Prene™, and die cut from bulk material. Upper side straps 220 and/or lower side straps 230 may be constructed from a narrow weave material so as to reduce or eliminate the waste incurred by die cutting.

In FIG. 3, the rigidizer 360 has a mesh construction adapted to sit over the patient's occiput. As illustrated, the rigidizer 360 is generally trapezoidal shaped with an upper end adapted to removably connect to upper side straps 320 associated with an upper portion of the mask and a lower end adapted to removably connect to lower side straps 330 associated with a lower portion of the mask. The mesh-like rigidizer 360 may be flexible to conform to the patient's head yet non-stretch to anchor the headgear in position, for example. However, the mesh may have other suitable constructions.

In each embodiment, the rigidizers extend generally vertical along the parietal bone of the patient's head and are adapted to cup and/or rest on the patient's occiput. As illustrated, the parietal bone rigidizers may be connected at the top and/or bottom (i.e., in order to sit over the occiput) and may include additional rigid or semi-rigid components to facilitate connection (e.g., see strap connectors in FIGS. 2 and 3). Also, the rigidizers avoid the use of any rigid or semi-rigid components at the back of the head where the patient's head would contact the bed in use. Preferably, the rigidizers are flexible or able to conform to the patient's head along their length, however cannot flex or deform across their width. This is so that the headgear is comfortable whilst maintaining its structural function of anchoring the mask in position.

1.2.1.2 Parietal and Zygomatic Rigidizer

Figure 5:
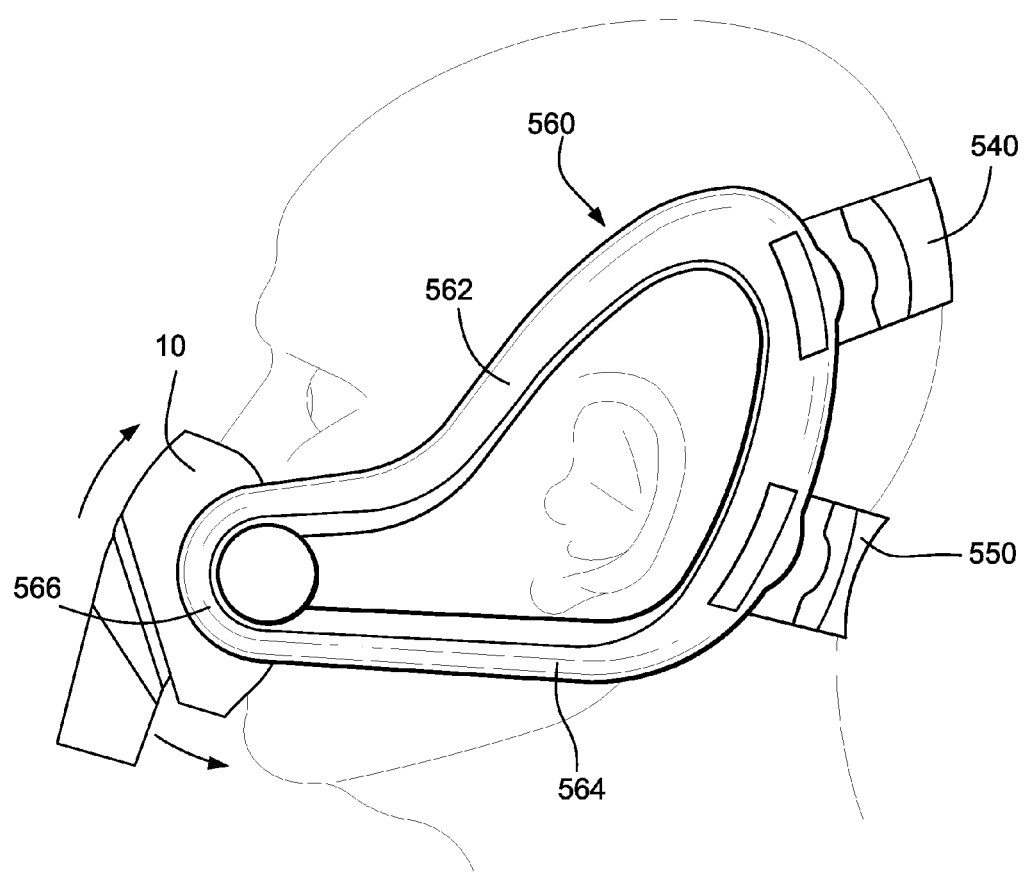
FIG. 5 is a side view of headgear in position on a patient's head according to another embodiment of the present technology.

FIGS. 4-5 illustrate headgear including rigidizers structured to conform to either side of the patient's parietal bone (i.e., in a generally vertical orientation) to anchor the headgear in position at the back of the patient's head, and extend to the front of the patient's head to the patient's zygomatic bone.

In FIG. 4, the rigidizer 460 is a continuous component with two side portions adapted to extend across the mask 10. As illustrated, each side portion includes an upper strap portion 462 that extends along the patient's parietal bone over the patient's ear and to the patient's zygomatic bone, and a lower strap portion 464 that extends below the patient's ear. The upper strap portion 462 extends across an upper portion of the mask 10 and the lower strap portion 464 extends across a lower portion of the mask 10.

As shown in FIG. 4A, the upper strap portion 462 may be removably clipped onto the mask 10. As illustrated, the upper portion of the mask 10 may include a plurality of spaced apart slots 15, and a clip 470 may extend through an opening in the upper strap portion 462 and into a selected one of the slots 15.

A flexible strap arrangement including an upper rear strap 440 and a lower rear strap 450 connect the left and right sides of the rigidizers 460 at the back of the patient's head. Upper rear strap 440 and lower rear strap 450 may be a continuous component, or may be separate components.

In FIG. 5, each rigidizer 560 is a continuous component adapted to connect to a respective side of the mask 10. As illustrated, each rigidizer 560 includes an upper strap portion 562 that extends along the patient's parietal bone over the patient's ear and to the patient's zygomatic bone, a lower strap portion 564 that extends below the patient's ear, and a front strap portion 566 adapted to connect to the mask 10.

In the illustrated embodiment, each rigidizer 560 is adapted to rotatably engage the side of the mask 10 (e.g., clip onto the side of the mask, wrap around anchor on the side of the mask) to allow rotational movement of the mask relative to the rigidizers 560, so that the mask can be rotated and adjusted for proper mask fit.

An upper rear strap 540 and a lower rear strap 550 connect the left and right sides of the rigidizers 560 at the back of the patient's head.

1.2.1.3 Occipital and Parietal Rigidizer

FIGS. 6-11 illustrate headgear including rigidizers structured to form a substantially complete circle/oval shape (e.g., could have an arc removed at the occiput for adjustability) to anchor the headgear in position at the back of the patient's head. As illustrated, the rigidizers extend along the patient's parietal and occipital bones.

Figure 6:
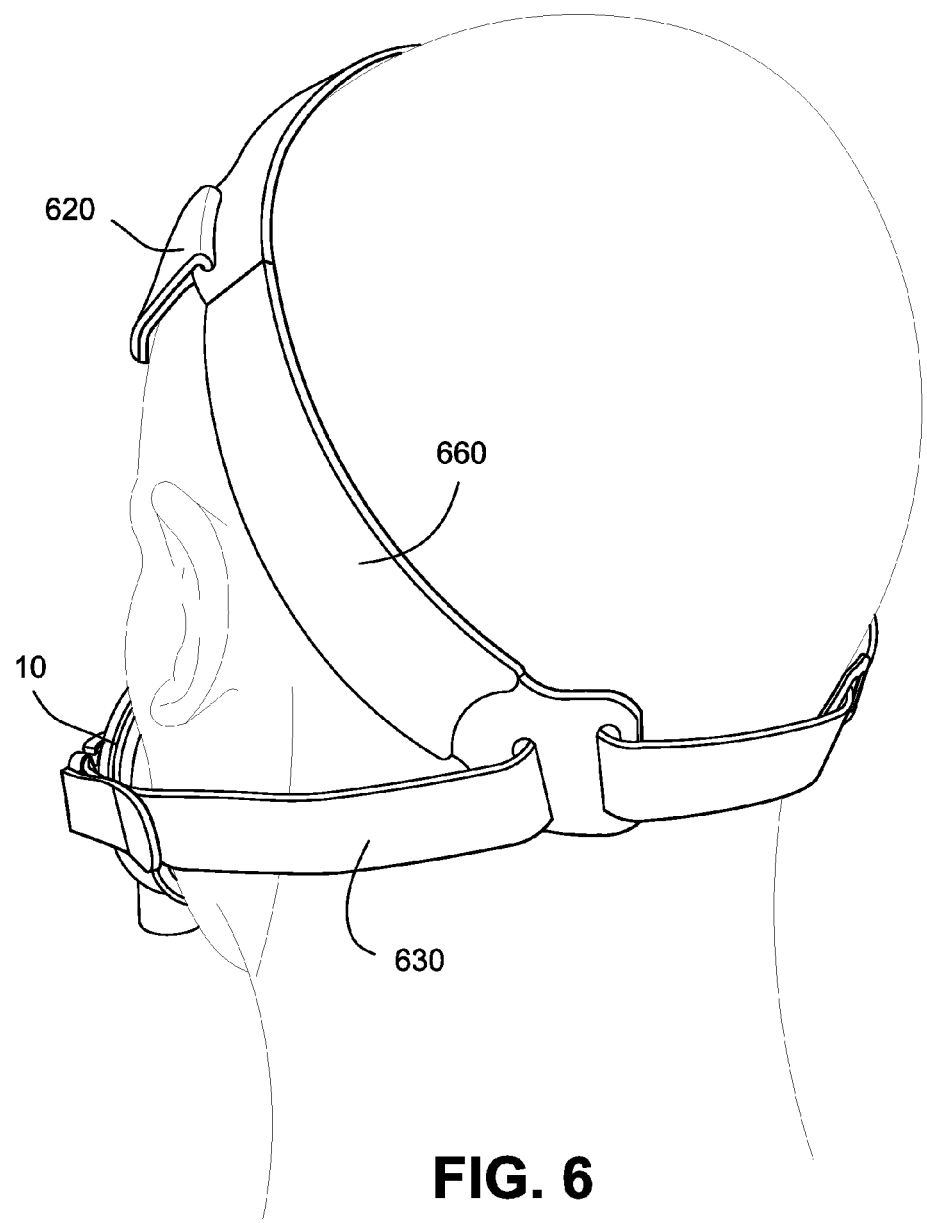
FIG. 6 is a rear perspective view of headgear in position on a patient's head according to another embodiment of the present technology.
Figure 7:
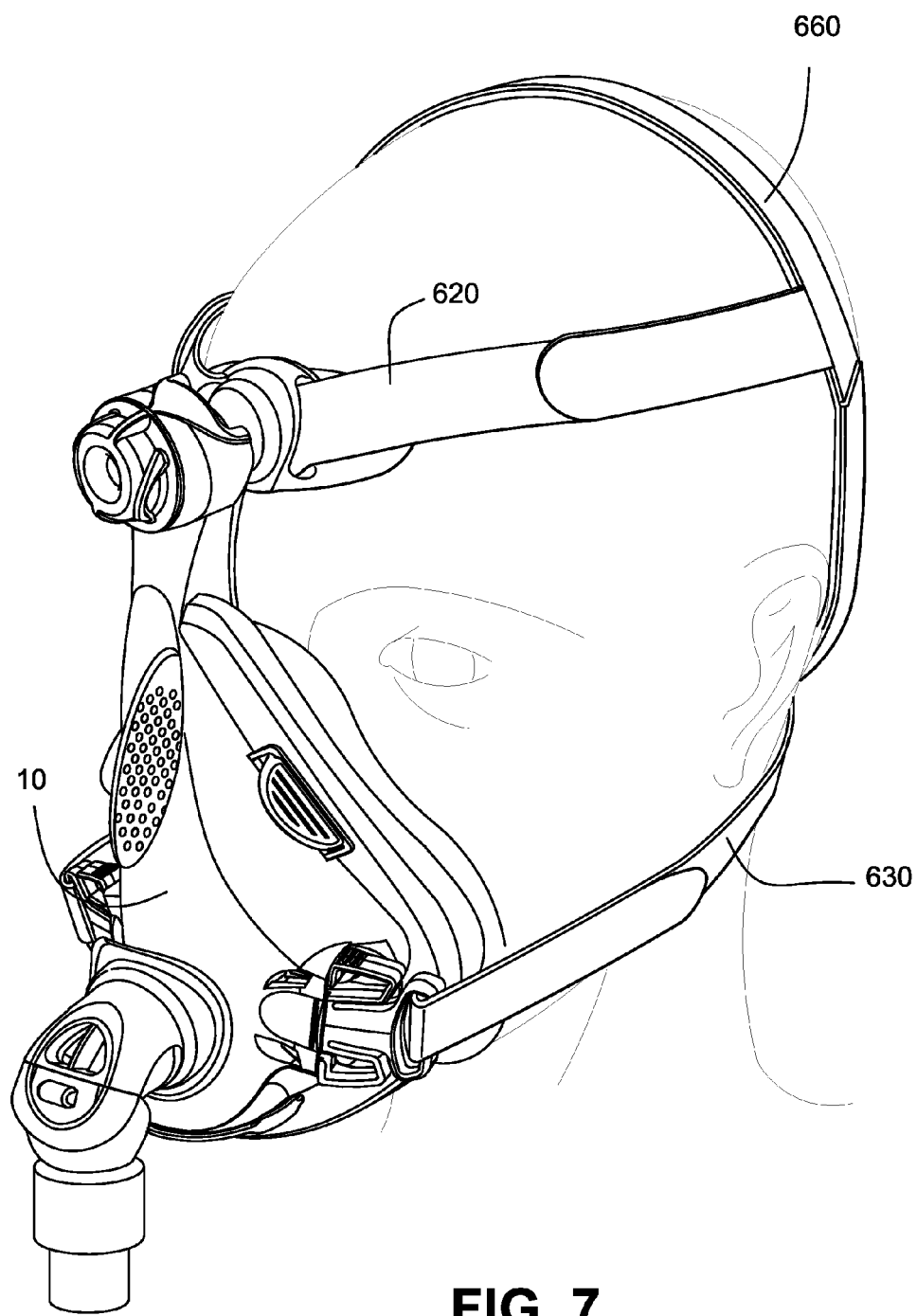
FIG. 7 is a front perspective view of the headgear of FIG. 6.

In FIGS. 6-7, the rigidizer 660 includes a substantially circular or oval shape with an arc removed at the lower end. The portion removed at the lower end may allow adjustment of the size of the circle/oval shape.

An upper side strap 620 removably connects an upper portion of the mask 10 (e.g., via forehead support) to the rigidizer and a lower side strap 630 removably connects a lower portion of the mask 10 (e.g., via headgear clip associated with clip receptacle) to the rigidizer.

Preferably, lower side strap 630 and/or rigidizer 660 engage with the occipital bone in order to maintain the rigidizer in position and prevent the headgear from riding up the back of the patient's head in use. In another preferred form, the upper side strap 620 and/or rigidizer 660 could capture or pass over the upper most part of the patient's parietal bone in use, so as to prevent the headgear from slipping back down the patient's head in use.

In another embodiment, upper side strap 620 and/or lower side strap 630 may have adjustable lengths. This may be achieved through the use of, for example, hook and loop fasteners. The lengths of the upper side strap 620 and/or lower side strap 630 should be such that the rigidizer 660 does not impinge on the patient's ear. For example, it could be possible to adjust the length of the upper side strap 620 or lower side strap 630 such that the rigidizer is urged towards the patient's face, and thus contacts the ear. This may cause discomfort to the patient.

In another preferred embodiment, lower side strap 630 is threaded through apertures in rigidizer 660 such that rigidizer 660 may slide along the length of lower side strap 630, thereby adjusting the size of the space encapsulated by rigidizer 660 and thus altering the shape of the headgear to suit different patient's head sizes. In another preferred form, lower side strap 630 may have engaging portions along its length such that if the size of the space encapsulated by rigidizer 660 is adjusted by sliding rigidizer 660 along the length of lower side straps 630, the position of the rigidizer 660 on lower side straps 630 can be secured in position. For example, engaging portions may be clips, Velcro, raised stitching, or any other means of securing the rigidizer 660 in position.

In another preferred embodiment, upper side strap 620, lower side strap 630 and/or rigidizer 660 maybe be formed individually such that each component is manufactured efficiently and cost effectively, (i.e. by nesting the components) as will be described below.

Figure 15:
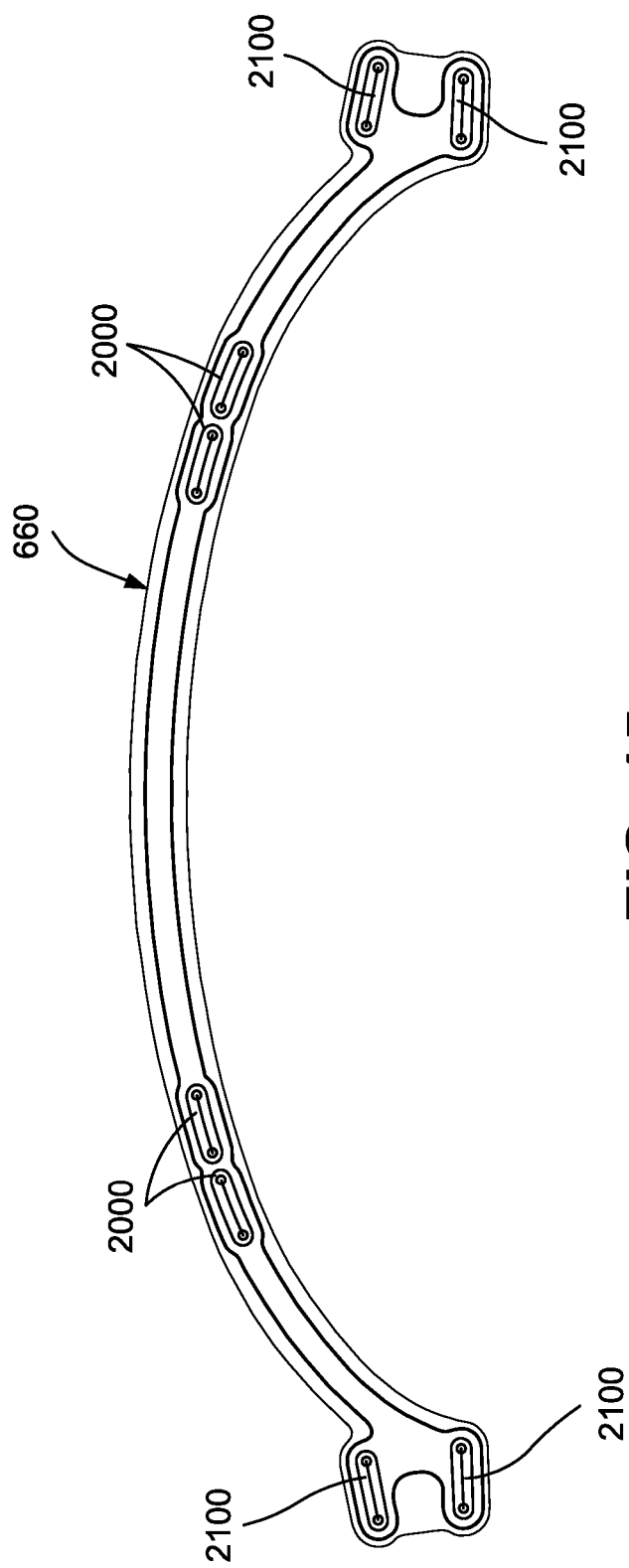
FIG. 15 is a front view of a rigidizer according to an embodiment of the present technology.

As shown in FIG. 15, rigidizer 660 may be formed from a flat component and then bent or deformed into a shape suitable for use. Rigidizer 660 may be die cut from sheet material. Rigidizer 660 may have upper apertures 2000 for engagement with upper side straps 620. Multiple upper apertures 2000 may be provided (for example, as shown in FIG. 15 there are 4 apertures) so that the patient can adjust the position of upper side strap 620. Rigidizer 660 may also have lower apertures 2100 for engagement with lower side straps 630.

Figure 8:
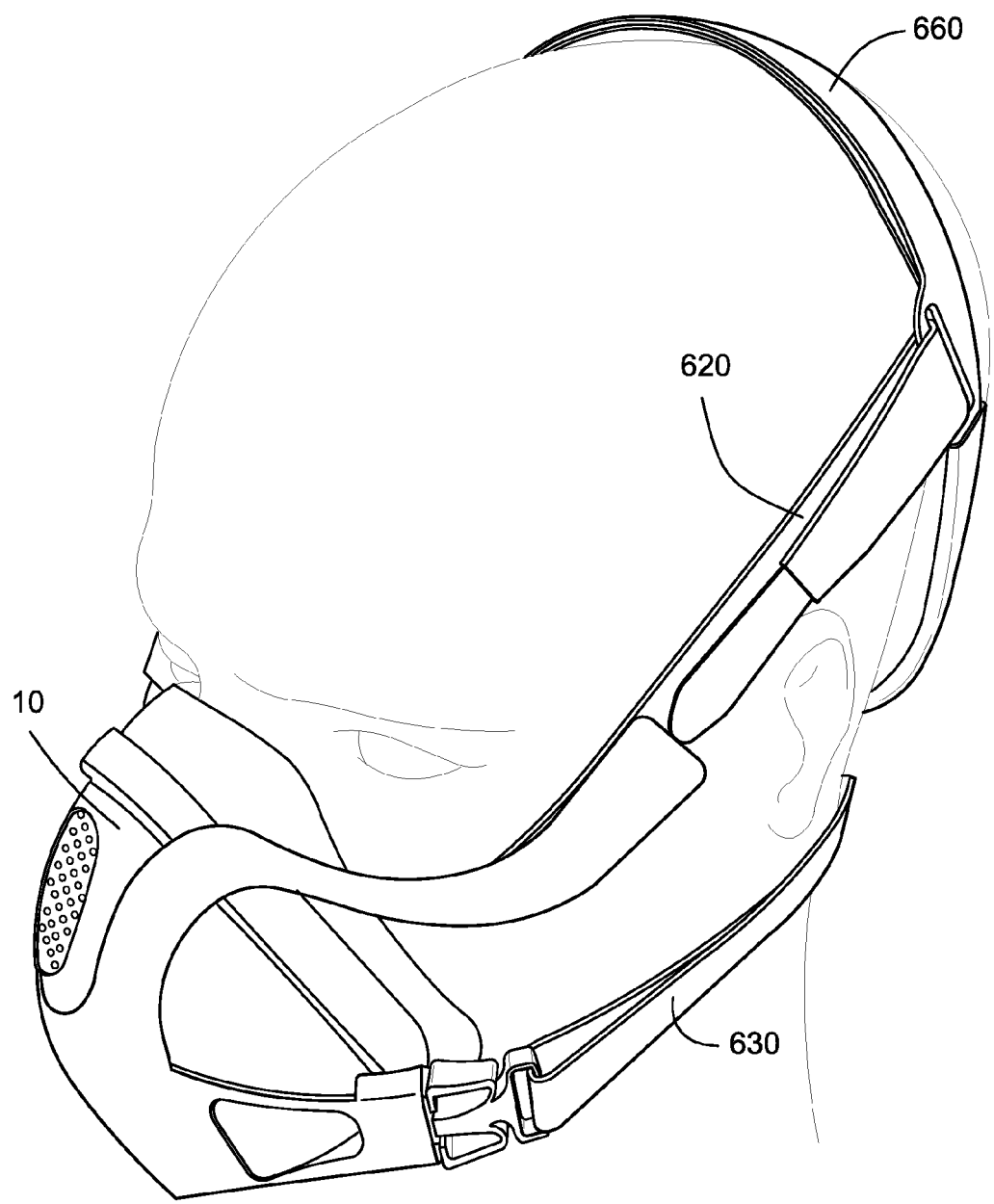
FIG. 8 is a front perspective view of the headgear of FIG. 6 provided to a different mask according to another embodiment of the present technology.
Figure 9:
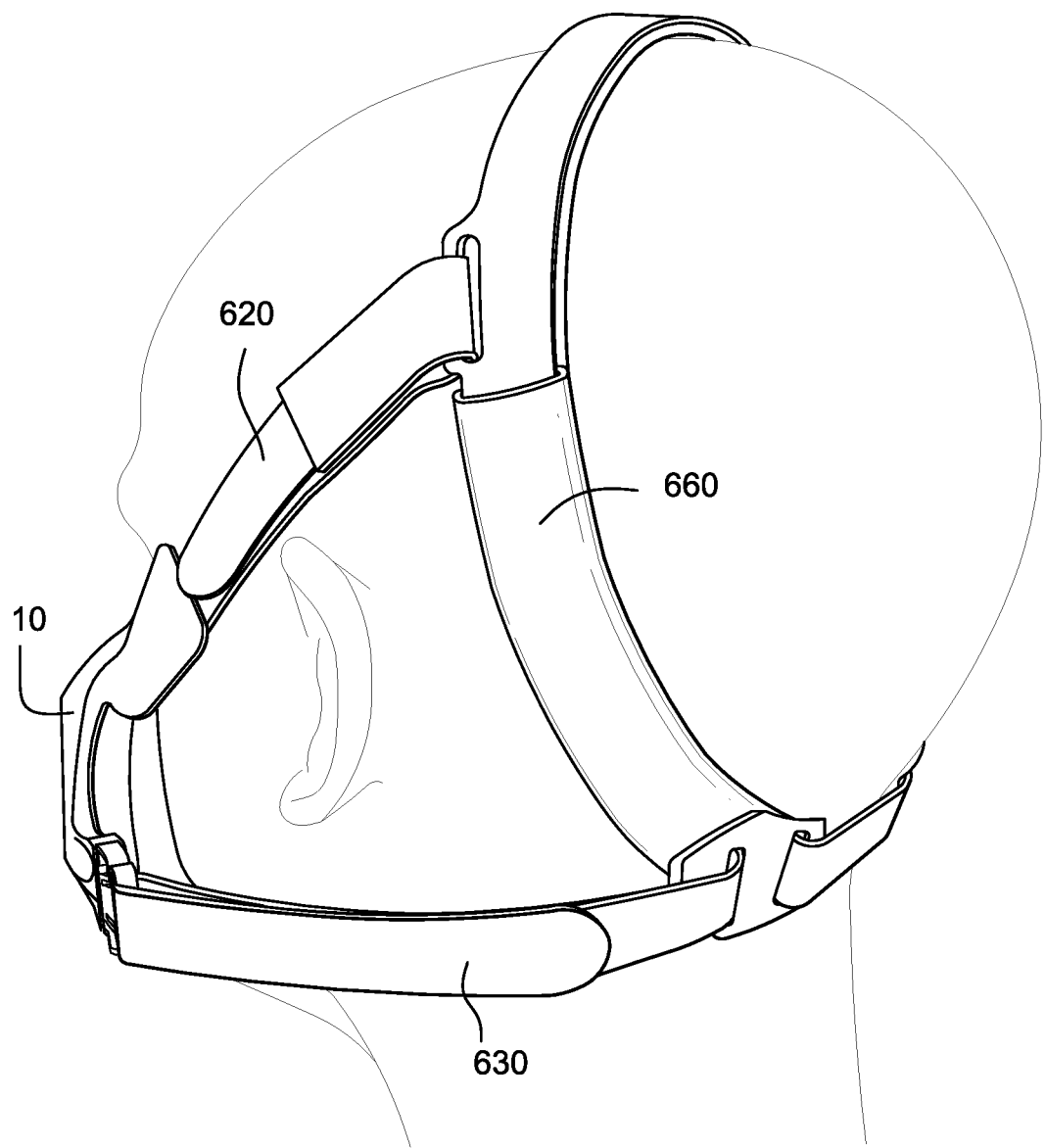
FIG. 9 is a rear perspective view of the headgear arrangement of FIG. 8.

FIGS. 8-9 show the headgear of FIGS. 6-7 attached to a mask with a different configuration. In this embodiment, the upper side strap 620 connects to a lateral outrigger of the mask 10 and the lower side strap 630 removably connects to the mask 10 via headgear clip associated with a mask clip receptacle. As best shown in FIG. 8, the upper side strap 620 may be connected to the lateral outrigger of the mask 10 by an adhesive, so that the upper side strap is adjustable only at the rigidizer. Alternatively, the upper side strap 620 may be adjustably connected to the slot provided at the end of the lateral outrigger of the mask 10, so that the upper side strap may be adjustable at both the rigidizer and lateral outrigger.

Figure 10:
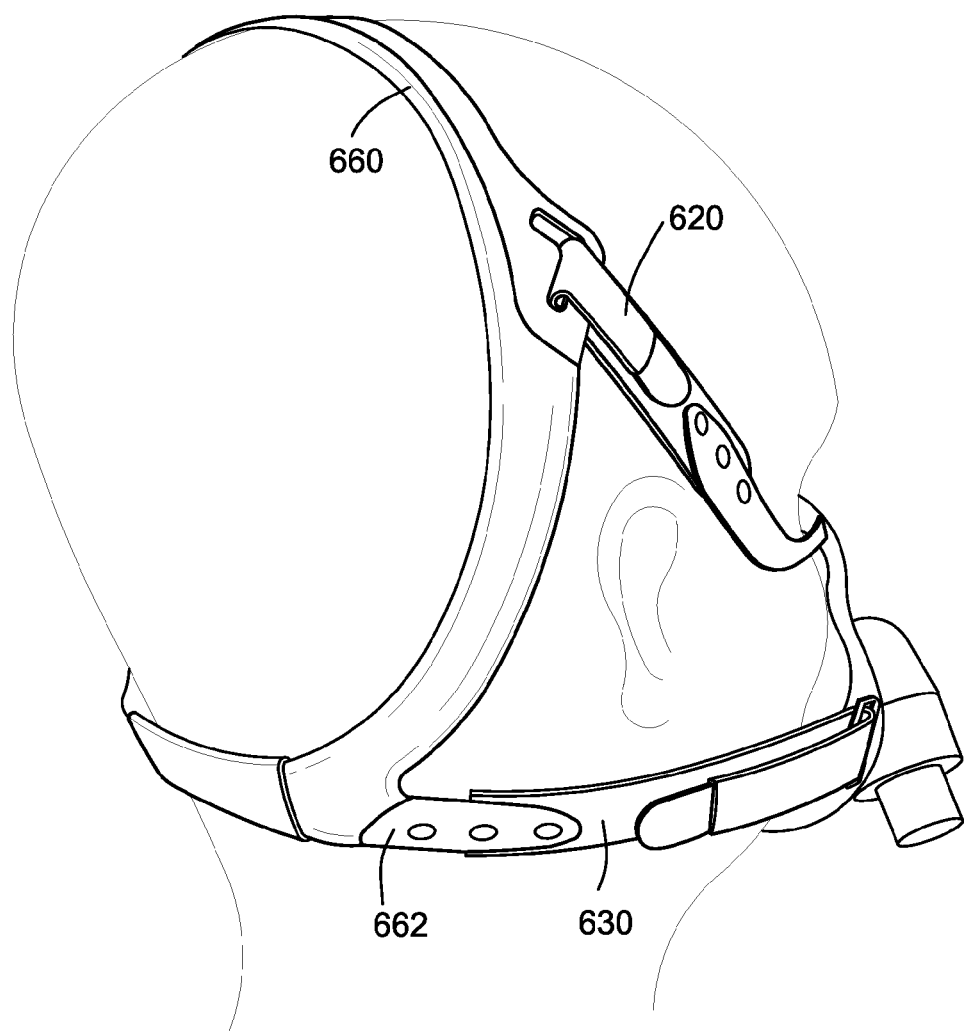
FIG. 10 is a rear perspective view of headgear in position on a patient's head according to another embodiment of the present technology.
Figure 11:
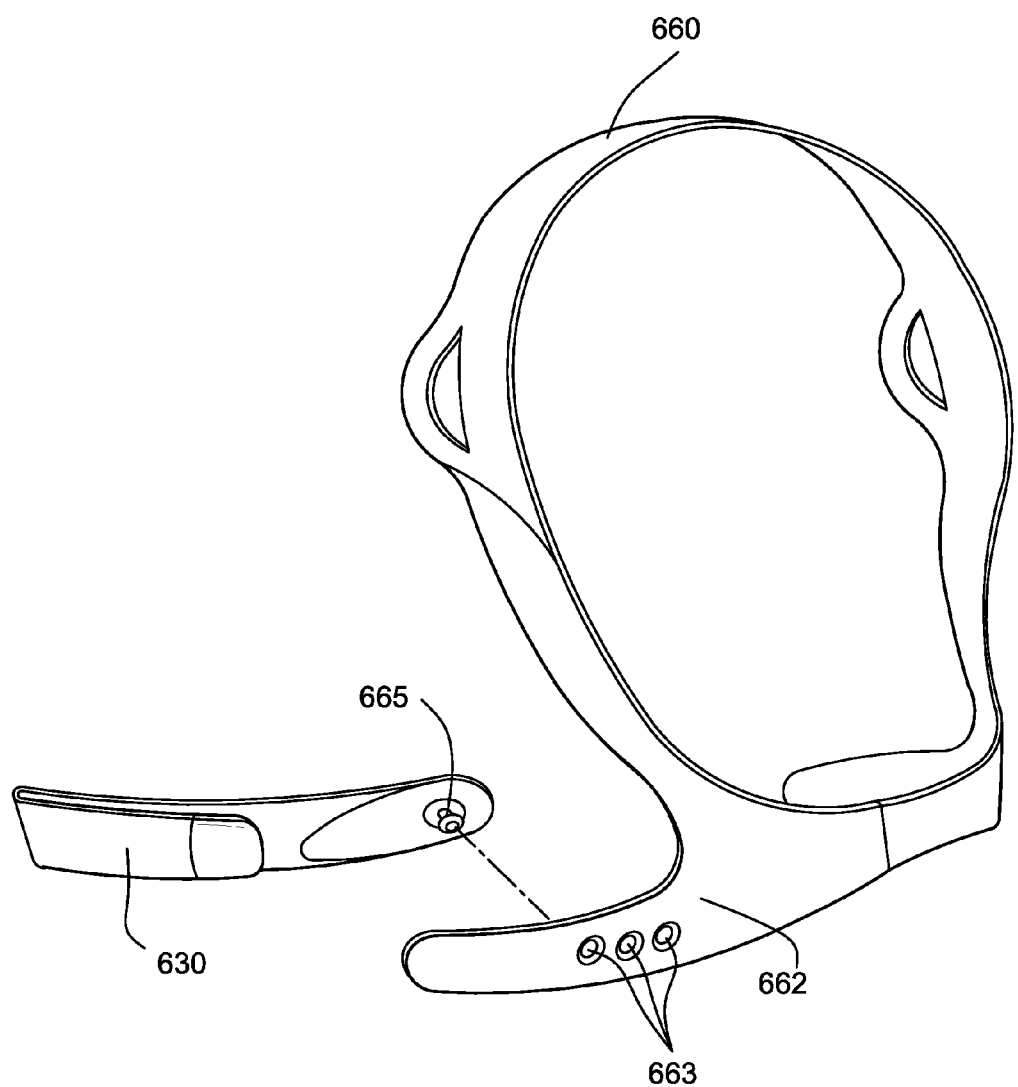
FIG. 11 is a perspective view of a rigidizer of the headgear of FIG. 10.
Figure 12:
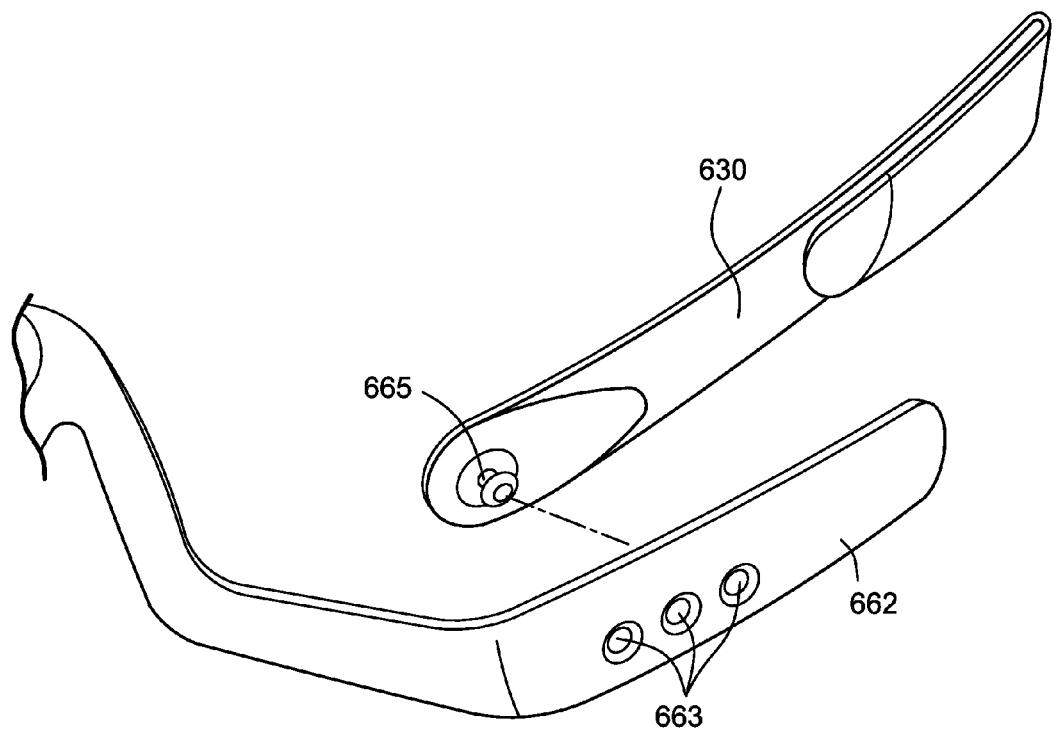
FIG. 12 is an enlarged view showing rigidizer attachment of FIG. 11.

FIGS. 10-11 show an alternative configuration for attaching the rigidizer 660 to the upper and lower side straps 620, 630 as described below.

Figure 40:
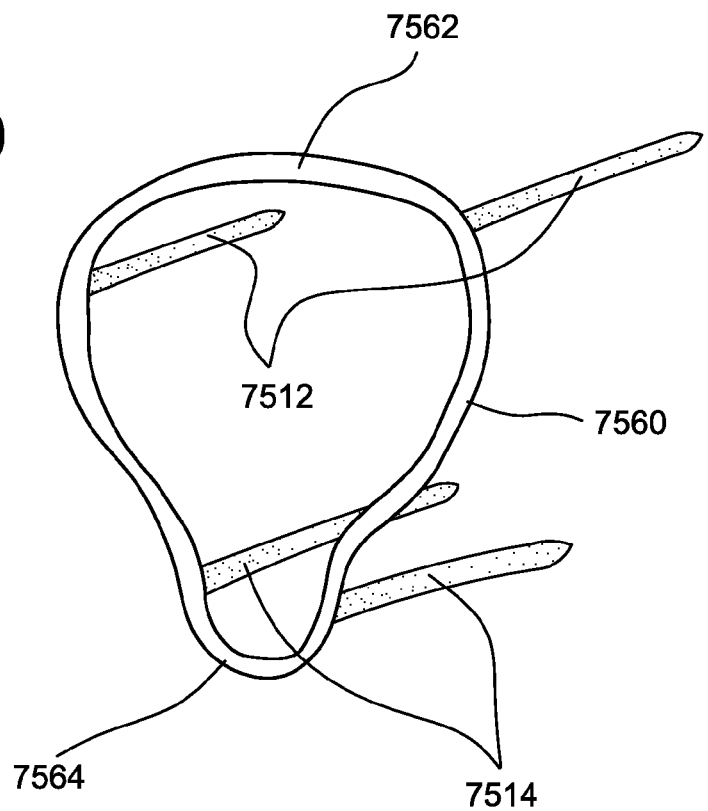
FIG. 40 shows a rigidizer according to an embodiment of the technology.

FIG. 40 shows an alternative arrangement for a rigidizer 7560 adapted to be positioned along a general rear portion of the patient's head in use. The rigidizer may be formed in a generally light bulb shape, where there are two generally round or curved portions, i.e., an upper portion 7562 adapted to engage the general region of the parietal bone of the patient's head in use and a lower portion 7564 adapted to engage the general region of the occipital bone of the patient's head in use. Upper straps 7512 are provided to the upper portion 7562 for engaging an upper portion of a mask, and lower straps 7514 are provided to the lower portion 7564 for engaging a lower portion of a mask.

1.2.2 Rigidizer/Strap Attachment

The one or more rigidizers may be coupled to the mask and/or with one another in alternative configurations.

In an embodiment, each rigidizer may include one or more slots to allow headgear straps to pass through it. For example, in FIG. 1, each end of the main body 62, the end of the lower arm 64, and the end of the upper arm 66 include a slot to allow the headgear strap to pass through it in use. FIG. 3 shows the mesh-like rigidizer 360 with upper and lower connectors 365, 366 (e.g., overmolded to mesh) with slots for receiving headgear straps. In FIG. 5, the rear portion of rigidizer 560 may include upper and lower slots for receiving upper and lower rear straps 540, 550. FIGS. 6-11 also show one or more slots provided to the rigidizer 660 for receiving headgear straps.

In another embodiment, the rigidizer may provide loops to receive headgear straps. For example, in FIG. 2, upper and lower ends of the rigidizer 260 include connectors 265 that provide a loop for receiving respective headgear straps. The lower connectors 265 are aligned with a slot in the rigidizer covering so that the lower strap 230 passes through the slot positioned at the back of the patient's head, i.e., lower strap 230 passes through a void in the rigidizer 260.

Figure 13:
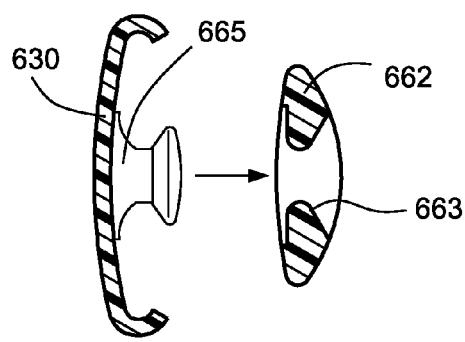
FIG. 13 is a cross-sectional view showing rigidizer attachment of FIG. 11.

FIGS. 10-13 show an arrangement wherein the rigidizer and straps provide a press stud arrangement. As illustrated, the lower end of the rigidizer may include a strap portion 662 with a plurality of holes 663, and one end of the lower strap 630 may provide a stud 665 (e.g., overmolded or sonically welded to strap) adapted to be press fit into a selected one of the holes 663. As shown in FIG. 13, the stud 665 and holes 663 are configured to provide a snap fit arrangement. The opposite end of the lower strap 630 may include a Velcro® tab for attachment to the mask.

Figure 25A:
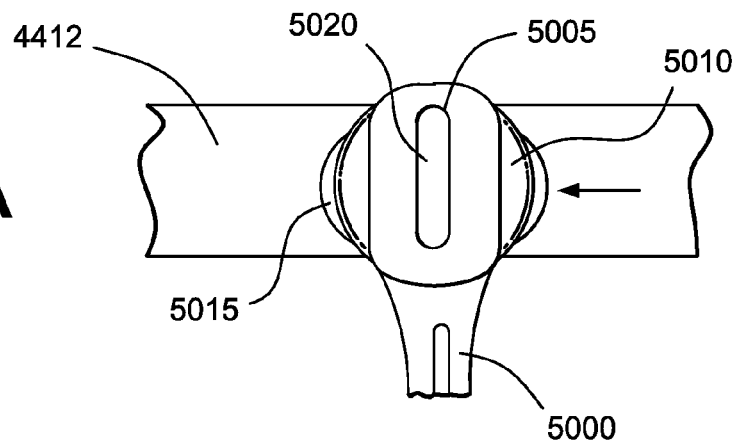
FIG. 25A is a front view of a forehead support according to a further embodiment of the present technology.
Figure 25B:
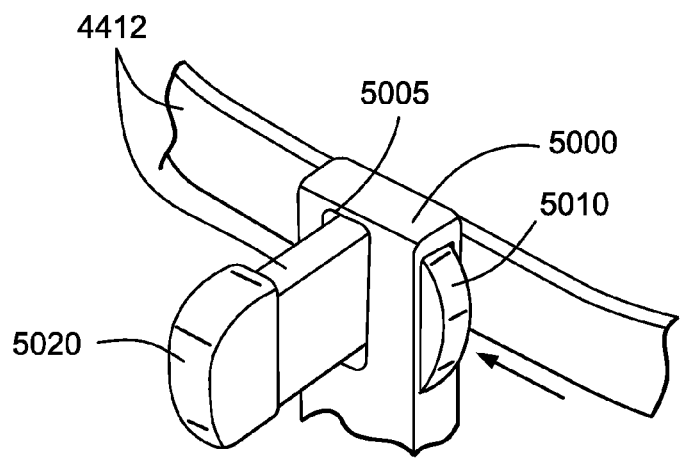
FIG. 25B is a perspective view of a forehead support according to a further embodiment of the present technology.
Figure 25C:
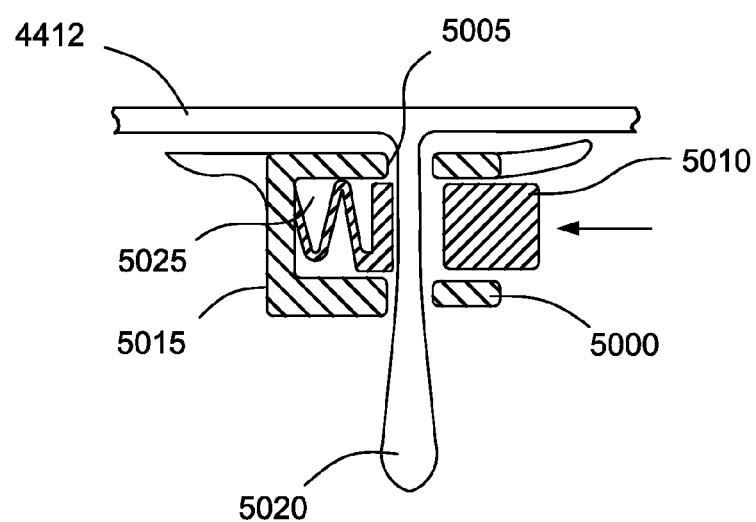
FIG. 25C is a cross section of a forehead support according to a further embodiment of the present technology.

FIGS. 25A to 25C show a further adjustment mechanism for a top strap 4412. A forehead support 5000 may be provided to a mask 10. Forehead support 5000 may allow the top strap to be looped through an aperture 5005. As best shown in FIG. 25C, forehead support may be provided with a push tab 5010 that is pre loaded or biased with spring 5025 so as to allow for engagement and disengagement of looped through portion of the top strap 4412. Gripping portion 5015 may be provided on an opposite side of the forehead support 5000 to push tab 5010 for the patient to stabilize the mechanism on their forehead. Additional gripping portion 5020 may be provided at the end of looped portion of top strap 4412. Additional gripping portion 5020 may also prevent disassembly of the looped portion by pulling it back through aperture 5005.

Figure 26:
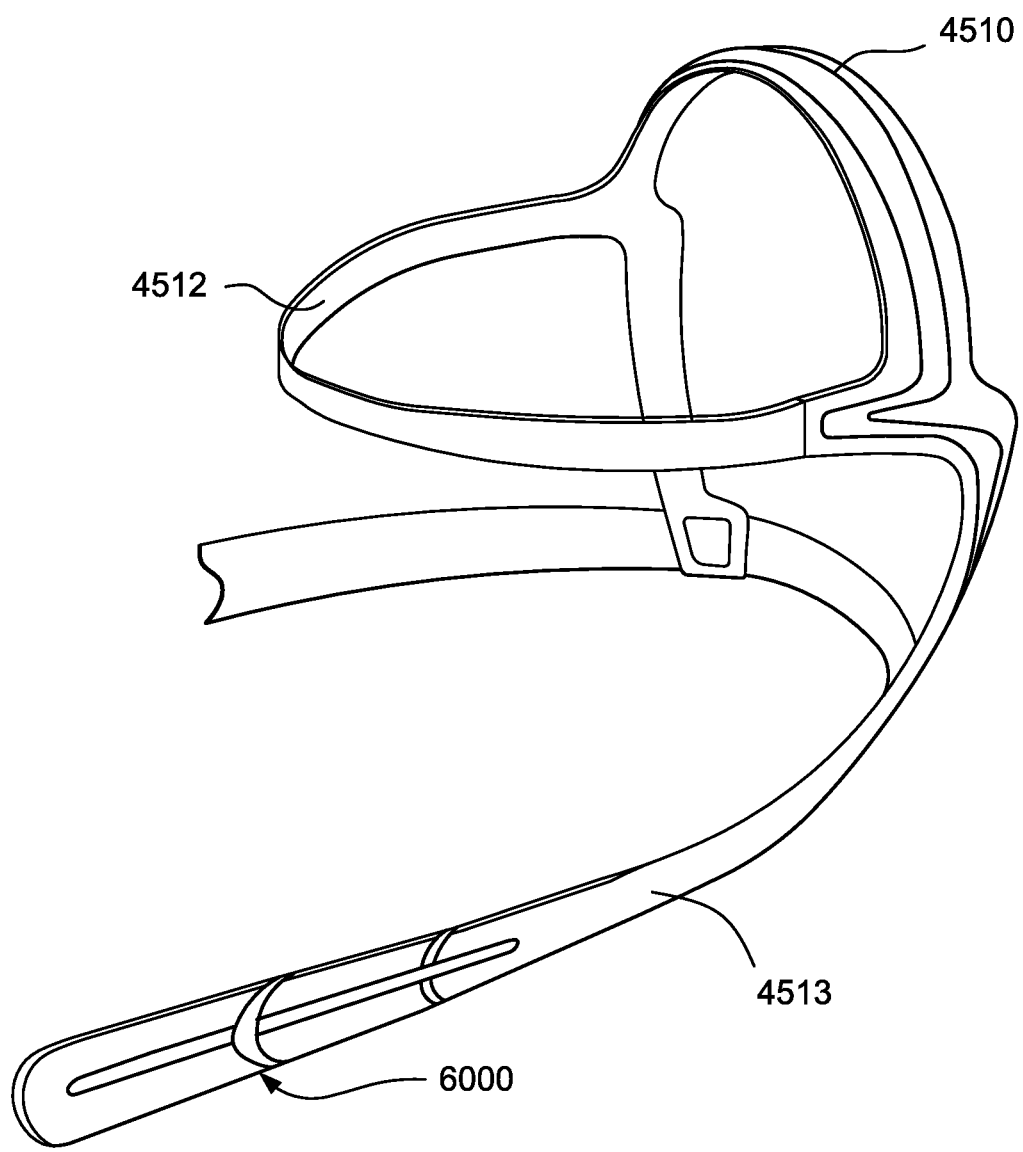
FIG. 26 is stylized perspective view of the assembled headgear according to a further embodiment of the present technology.

FIG. 26 also shows a further alternative method of adjusting bottom straps 4513, wherein the perforations 6000 may be provided along the length of the bottom strap 4513 that may allow the patient to tear or cut segments of the bottom strap 4513 off to shorten its length. Perforations 6000 may be weakened regions along the bottom strap 4513, for example thinner cross section, narrower strap width.

Additional Embodiments

Figure 18:
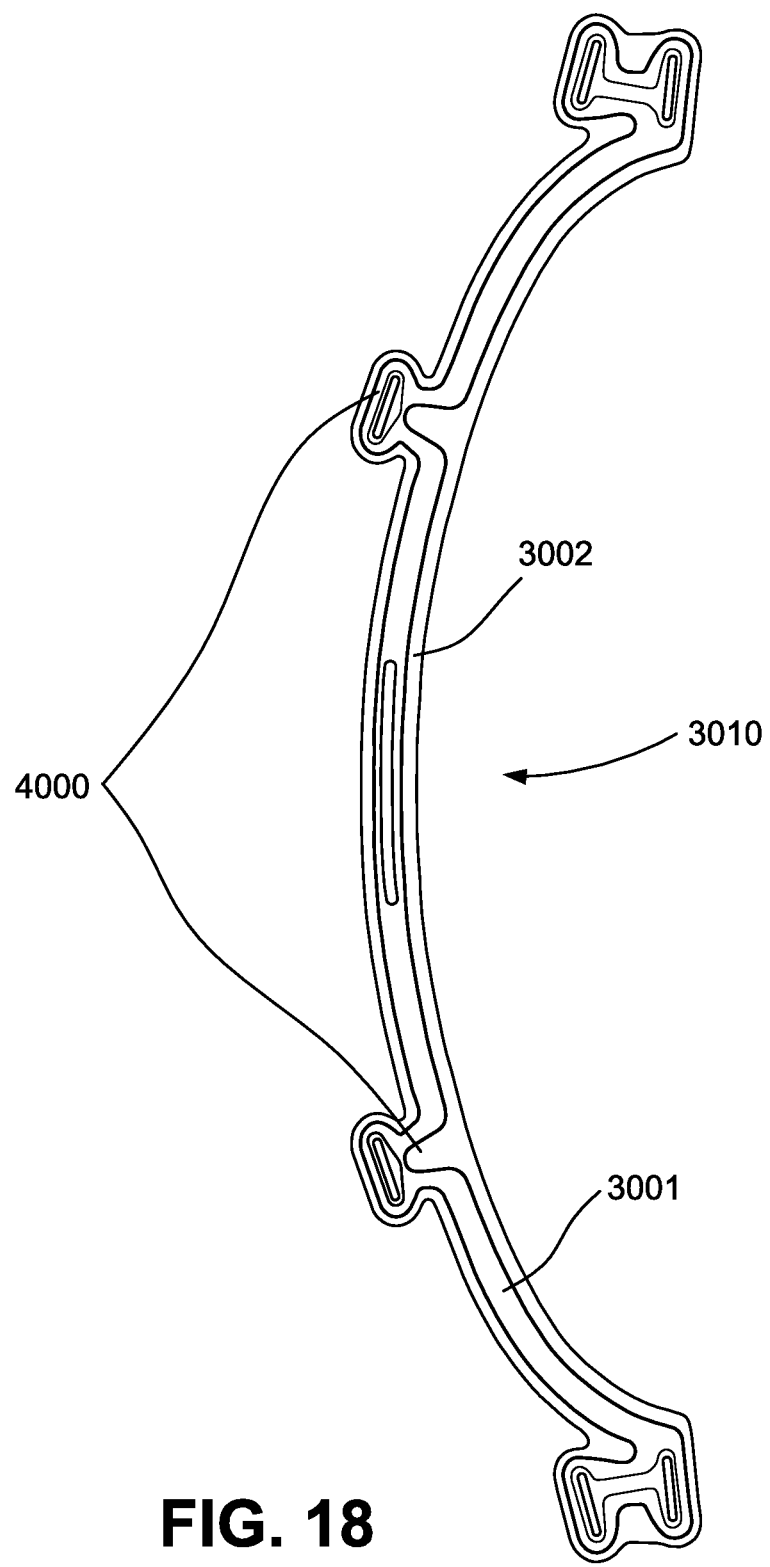
FIG. 18 is a cross-sectional top view of a strap according to the same embodiment depicted in FIG. 17.

FIG. 18 also shows a first strap 3010 with an encapsulated rigidizer 3001 that may have bows or bends 4000. Bends 4000 may be provided in select region(s) of rigidizer 3001 to allow the rigidizer to readily flex or hinge at the region(s). This may be beneficial for fitting a larger range of patient head sizes. As shown in FIG. 18, bends 4000 may be positioned so as to allow lower portions of the rigidizer to flex outwards towards the ears of the patient or inwards towards the centre of the patient's head. Bends 4000 may be weakened regions to achieve a similar flexibility in the rigidizer 3001. For example, bends 4000 may be curved portions, portions with a thinned cross section, narrowed portions of the width of the rigidizer 3001. This bending portion may not be in tension as other parts of the headgear, e.g., the upper and lower headgear straps for direct attachment to the mask system.

Figure 20:
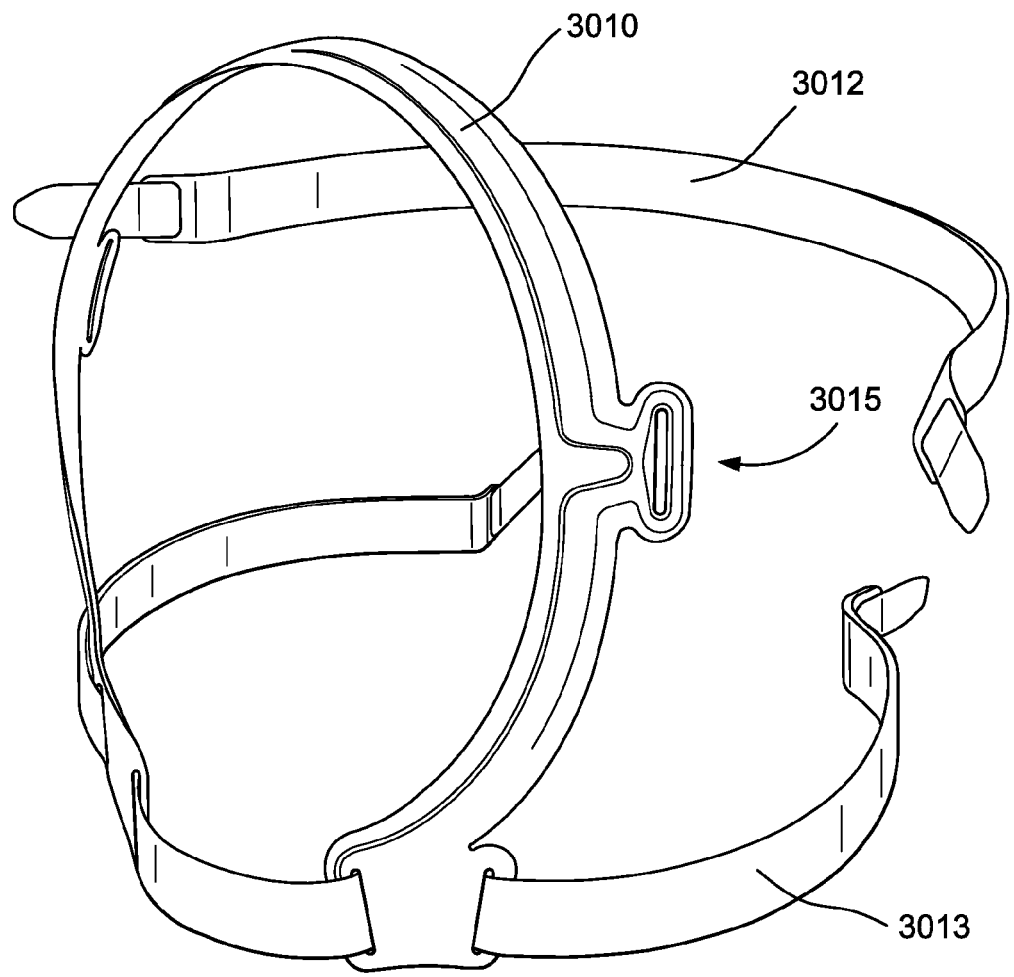
FIG. 20 is stylized perspective view of the assembled headgear pursuant to the embodiment depicted in FIG. 17.

FIG. 20 shows a further arrangement wherein the first strap 3010 may have an encapsulated rigidizer 3001 (not shown) and may be provided with a top strap 3012 and a bottom strap 3013. Top strap 3012 and bottom strap 3013 may each be a single length of material that may loop through or otherwise attach to first strap 3010. Securing means (for example, hook and loop attachment, press studs, adhesive) may be attached at the ends of top strap 3012 and bottom strap 3013 to allow for adjustment of the length of the straps.

Figure 21:
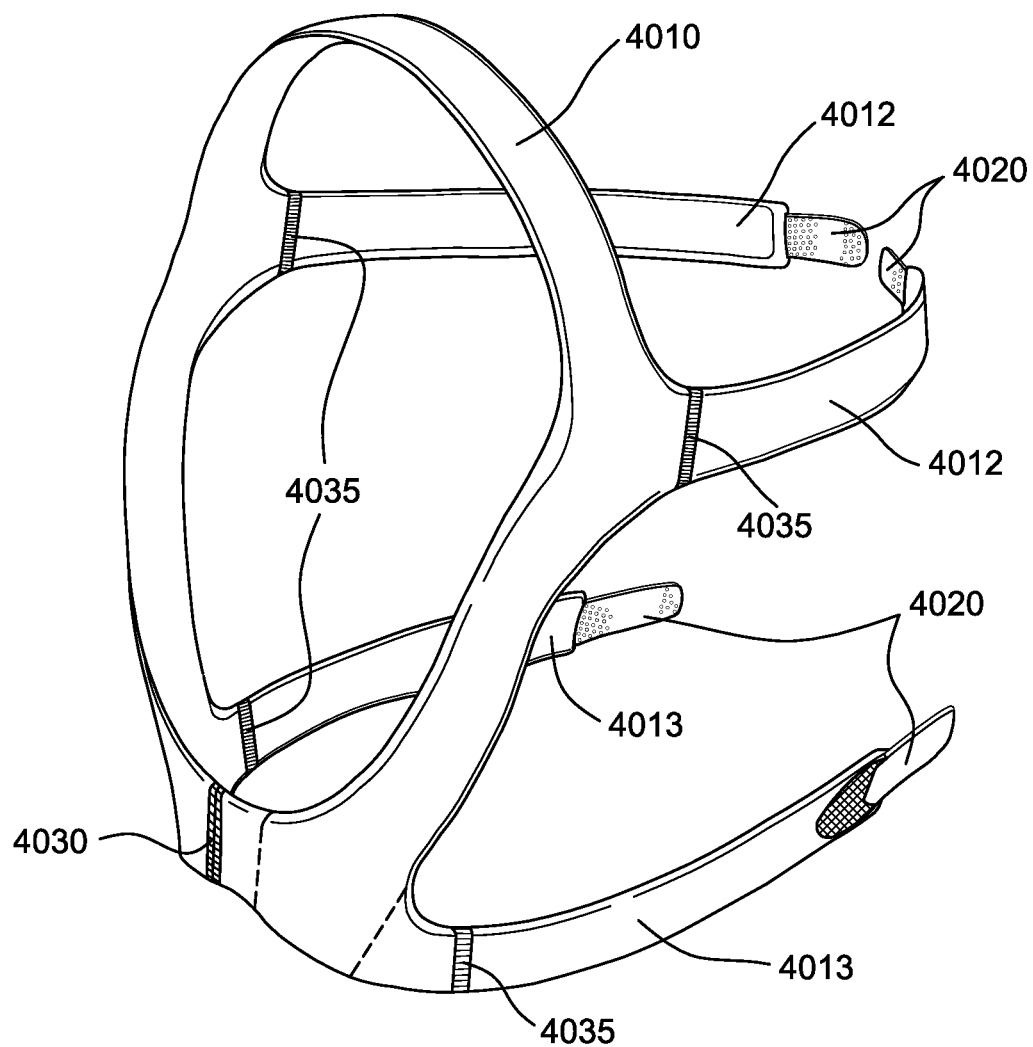
FIG. 21 is stylized perspective view of the assembled headgear according to a further embodiment of the present technology.

FIG. 21 shows a further arrangement wherein a first strap 4010 (that may be provided with an encapsulated rigidizer (not shown)) is joined at its lower end by stitching, gluing, welding, or other means. Alternatively, first strap 4010 may be formed of a single circle or loop or material. First strap 4010 may be formed in one piece by ultrasonic die cutting. The circumference of the first strap (measured from the inner edge, or edge that is furthest from the top strap 4012 and bottom strap 4013) may be about 420-600 mm. Preferably, the circumference may be about 480-540 mm. Preferably, the circumference may be about 490-505 mm. Preferably the circumference may be about 500 mm. With a circumference in these ranges, the headgear may fit the crown region of the head for a larger proportion of the population. Additionally, the rigidizer may avoid contacting the ears of the patient. Furthermore, the rigidizer may avoid contacting the lower neck or upper back or spine of the patient.

FIG. 21 also shows top straps 4012 attached to first strap 4010 at join 4035. Join 4035 may be stitching, ultrasonic welding, gluing, or any other joining means, or a combination of means. Top straps 4012 may be provided with adjustment means 4020 at their free ends, for example hook or loop material, press studs, etc. Bottoms straps 4013 may be attached to first strap 4010 by join 4035. Join 4035 may be stitching, ultrasonic welding, gluing, or any other joining means, or a combination of means. Bottom straps 4013 may be provided with adjustment means 4020 at their free ends, for example hook or loop material, press studs, etc. In a further alternative embodiment, first strap 4010, top straps 4012, and bottom straps 4013 may be formed in one piece. The single component may be formed by manually rolling an ultrasonic welder around the perimeter of the component. In an embodiment, this method may provide some edges that are not consistent as this method relies on manual control of the process. The single component may be constructed by ultrasonic die cutting. This may be advantageous as each headgear may be more uniform or consistent as the process can be more strictly controlled. Alternative methods of construction are also possible, including ultrasonic welding and CNC knife cutting.

Figure 22:
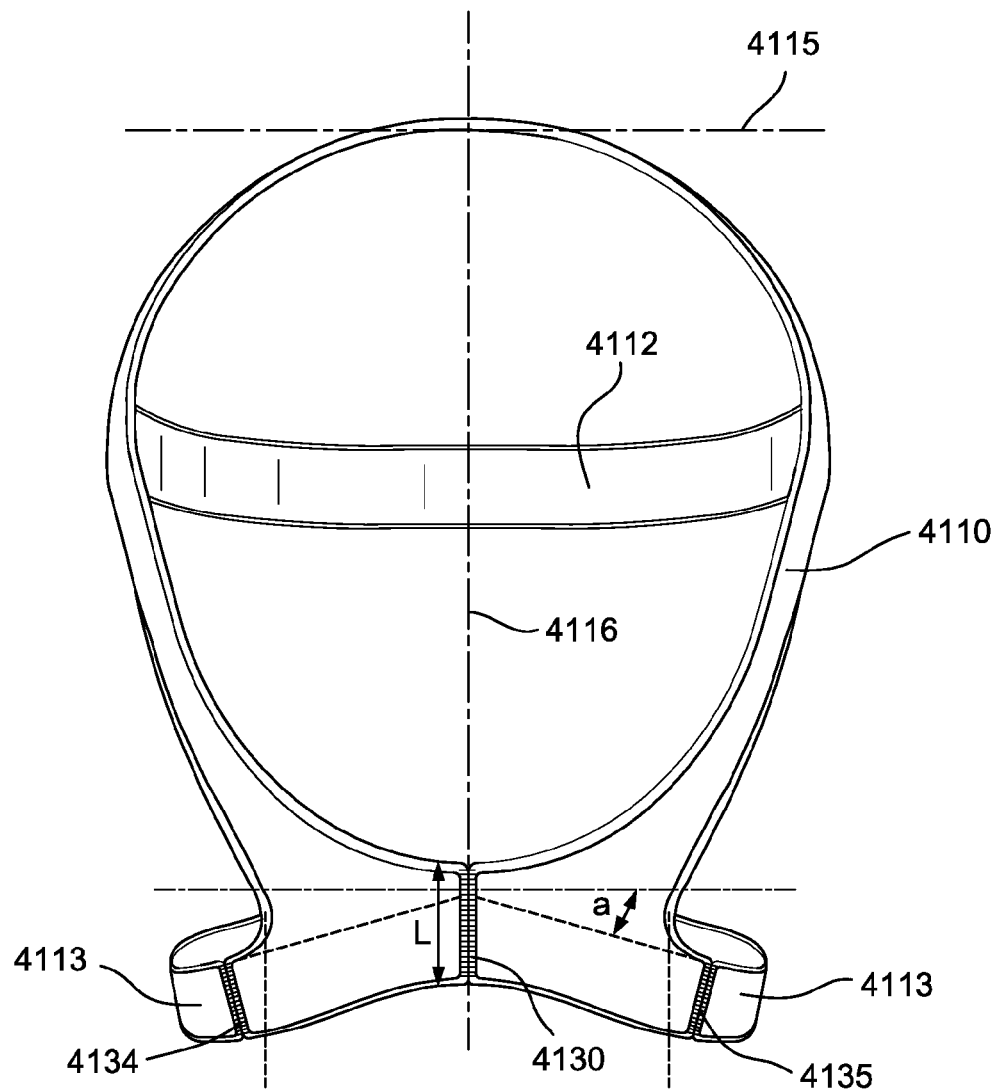
FIG. 22 is a rear view of the assembled headgear according to a further embodiment of the present technology.

FIG. 22 shows a rear view of a first strap 4110 (that may be provided with an encapsulated rigidizer (not externally visible in FIG. 22)) in its in use position. Angle a shows the angle of alignment of the bottom straps 4113 with respect to a horizontal plane. Bottom straps 4113 are preferably angled or deflected downward by angle a to guide the bottom straps below the ears of the patient. Angle a may be greater than 0°. Angle a may be 0°-90°. Preferably, angle a may be about 10°-30°. Preferably, angle a may be about 15°-20°. Angle a may be about 11°. First strap 4110 may also be provided with a top strap 4112 that may be elastic. Bottom straps 4113 may be attached to first strap 4110 by joins 4134, 4135.

FIG. 22 also shows length L, which is the width of the lower portion of the first strap nearest join 4130. Preferably, length L may be less than about 60 mm to avoid contact with the neck or upper back or spine of the patient. Preferably, length L may be about 30-50 mm.

As shown in FIG. 22, the upper region of the headgear defined by the first strap 4110 is arched to engage the crown of the patient's head. In use, the first strap 4110 extends in a horizontal plane 4115 through the widest portion of the arched region so as to lie flat on the crown of the patient's head. The lower portions or sides of the first strap 4110 extend through a vertical plane (parallel to vertical axis 4116) at the widest portions of the lower portions or sides of the first strap. This configuration allows the region of the headgear including the first strap 4110 to lie flat on the back of the patient's head. In the case where the first strap 4110 is provided with an encapsulated rigidizer, the configuration of the first strap 4110 in combination with the rigidizer provides the headgear with a 3D shape.

Figure 23:
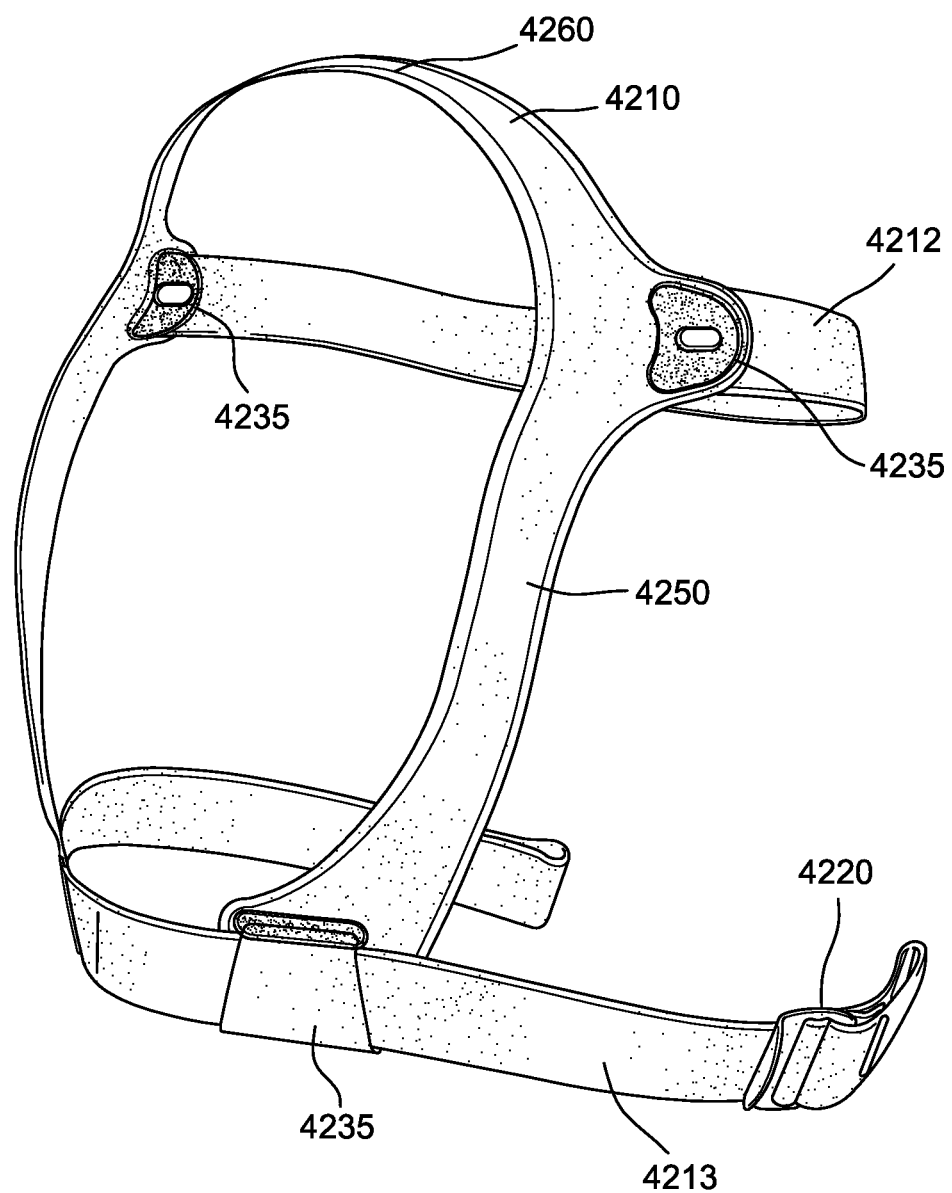
FIG. 23 is stylized perspective view of the assembled headgear according to a further embodiment of the present technology.

FIG. 23 shows a further arrangement wherein first strap 4210 (that may be provided with an encapsulated rigidizer (not shown)) may be attached to top strap 4212 by joins 4235. Joins 4235 are shown as ultrasonic welds, however may be any other reasonable method of attaching the top strap 4212 to first strap 4210. Top strap 4212 may be elastic, or any other suitable material. Bottom strap 4213 may be passed through loops 4235 on first strap 4210. Bottom strap 4213 may be made from elastic or any other suitable material. Bottom strap 4213 may also be adjustable by providing ladder locks 4220 on its ends. By sliding ladder locks 4220 along the length of bottom strap 4213, the length of the strap may change.

FIG. 23 further shows rigidizer lower portion 4250 that may be curved in such a way so as to avoid contacting the back of the patient's ear when in use. The curvature of this lower portion 4250 on FIG. 20 is such that the first strap 4210 follows a similar radius of curvature along its length. As shown in FIG. 23, the radius of curvature of lower portion 4250 is different to that of the upper portion 4260. Lower portion 4250 may have a radius of curvature less than that of upper portion 4260. The shape of first strap 4210 may be similar to the rigidizer 4201 (not externally visible in FIG. 23) encapsulated within it.

Figure 27:
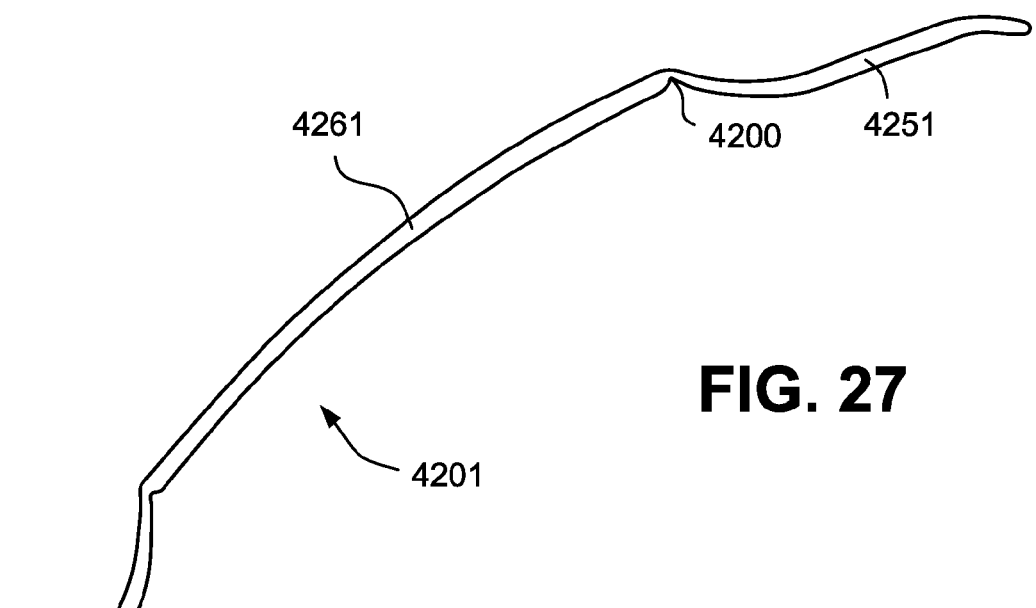
FIG. 27 is rigidizer according to a further embodiment of the present technology.

FIG. 27 shows rigidizer 4201 where the lower portion 4251 may have a radius of curvature less than that of upper portion 4261. Alternatively, a bend 4200 may be provided to rigidizer 4201 so that lower portion 4251 is positioned further in towards the centre of the patient's head thereby avoiding contact with the back of the patient's ears in use.

Figure 28:
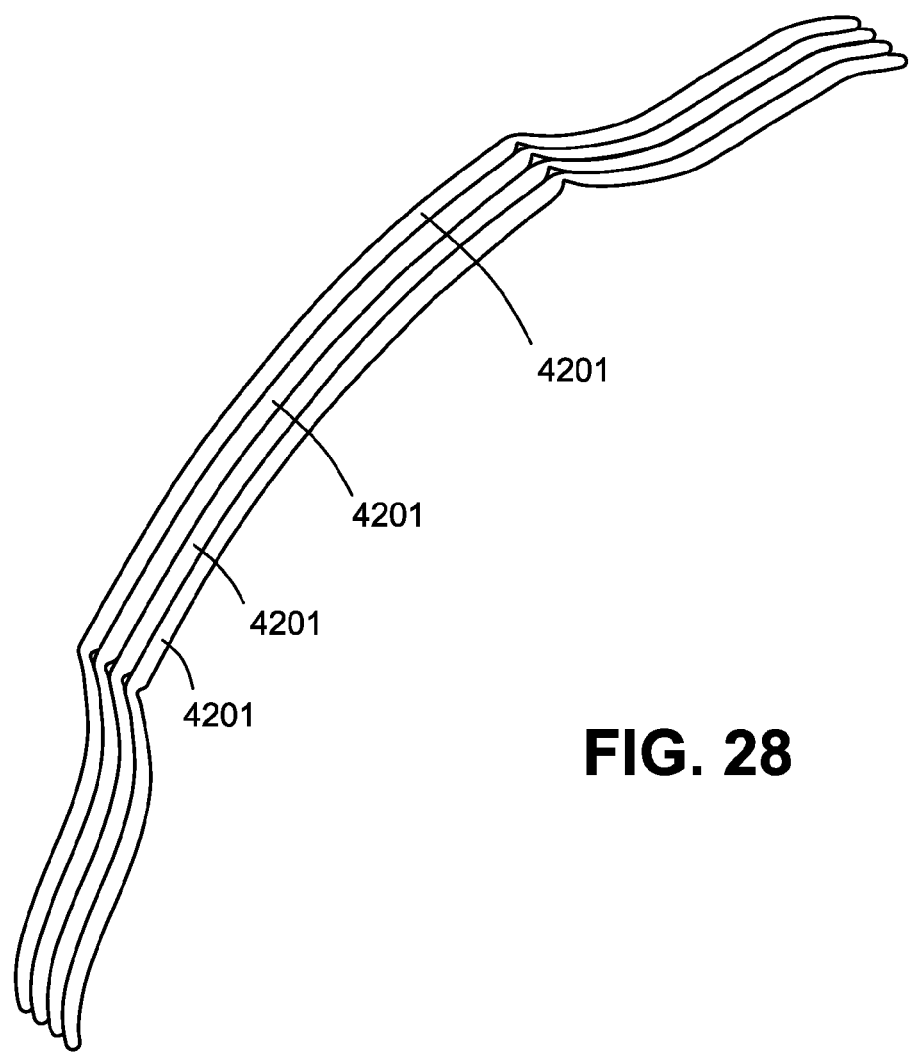
FIG. 28 is a series of rigidizers nested according to a further embodiment of the present technology.

FIG. 28 shows rigidizer 4201 nested or positioned multiple times on a single piece of base material to demonstrate the ability of the rigidizer's shape to be manufactured and wherein multiple rigidizers 4201 are produced with minimal wasted base material.

Figure 29:
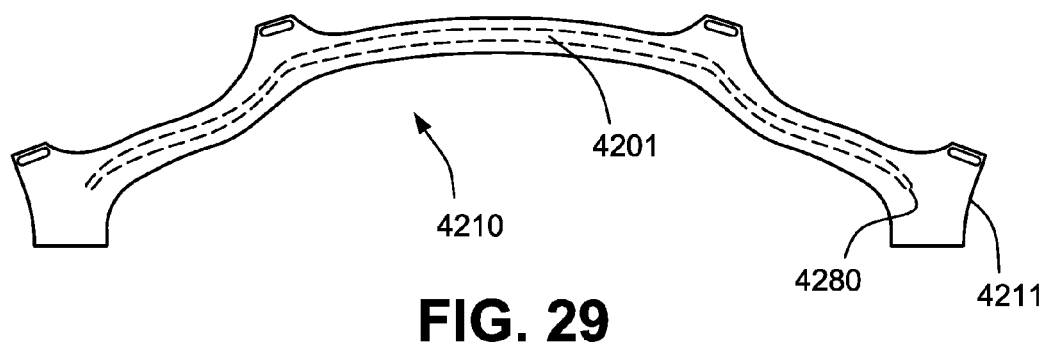
FIG. 29 is top view of the unassembled top strap according to a further embodiment of the present technology.

FIG. 29 shows a flattened first strap 4210 with the encapsulated rigidizer 4201 (as delineated by dashed lines) to demonstrate the similar curvature or general arcuate shape of the two parts when formed or joined together. In this embodiment, either end 4280 of rigidizer 4201 may preferably: have a maximum length no greater the furthest point of the end 4211 of first strap 4210; and have a preferred minimum length of no less than the distance required to prevent or limit the end 4211 from distorting or bending, when a further strap is connected to end 4211 and when the headgear is tightened on a patient's head. This feature may also avoid rigidizer 4201 causing discomfort or irritation on the patient's neck or upper back/spine.

Figure 30:
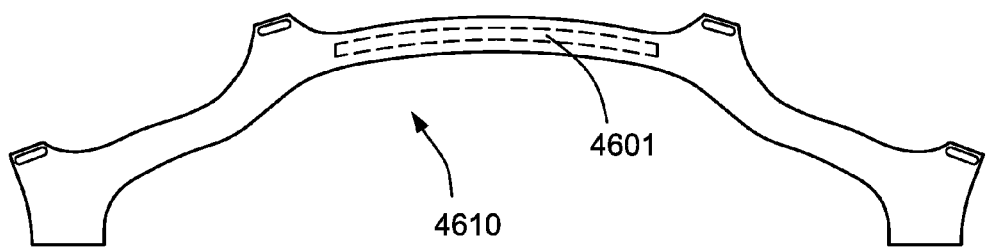
FIG. 30 is top view of the unassembled top strap according to a further embodiment of the present technology.

FIG. 30 shows a further embodiment of the present technology, where rigidizer 4601 may be encapsulated within a first strap 4610. Rigidizer 4601 may extend only across the centre portion of first strap 4610, such that when in use, is only located at approximately the top, upper half of the patient's head. This may increase comfort while maintaining the stability of previous embodiments. Additionally, the reduced length rigidizer 4601 may increase the comfort of this embodiment and yet more allow the strap to retain a shape and configuration that may allow a user or patient to quickly fit or wear the headgear. One advantage of rigidizer being mounted within the headgear is the part of the headgear that engages the rear portion of the patient's head includes enough support in the form of rigidity to maintain its basic shape and to prevent or limit distortion whilst the patient is donning the headgear.

Figure 24:
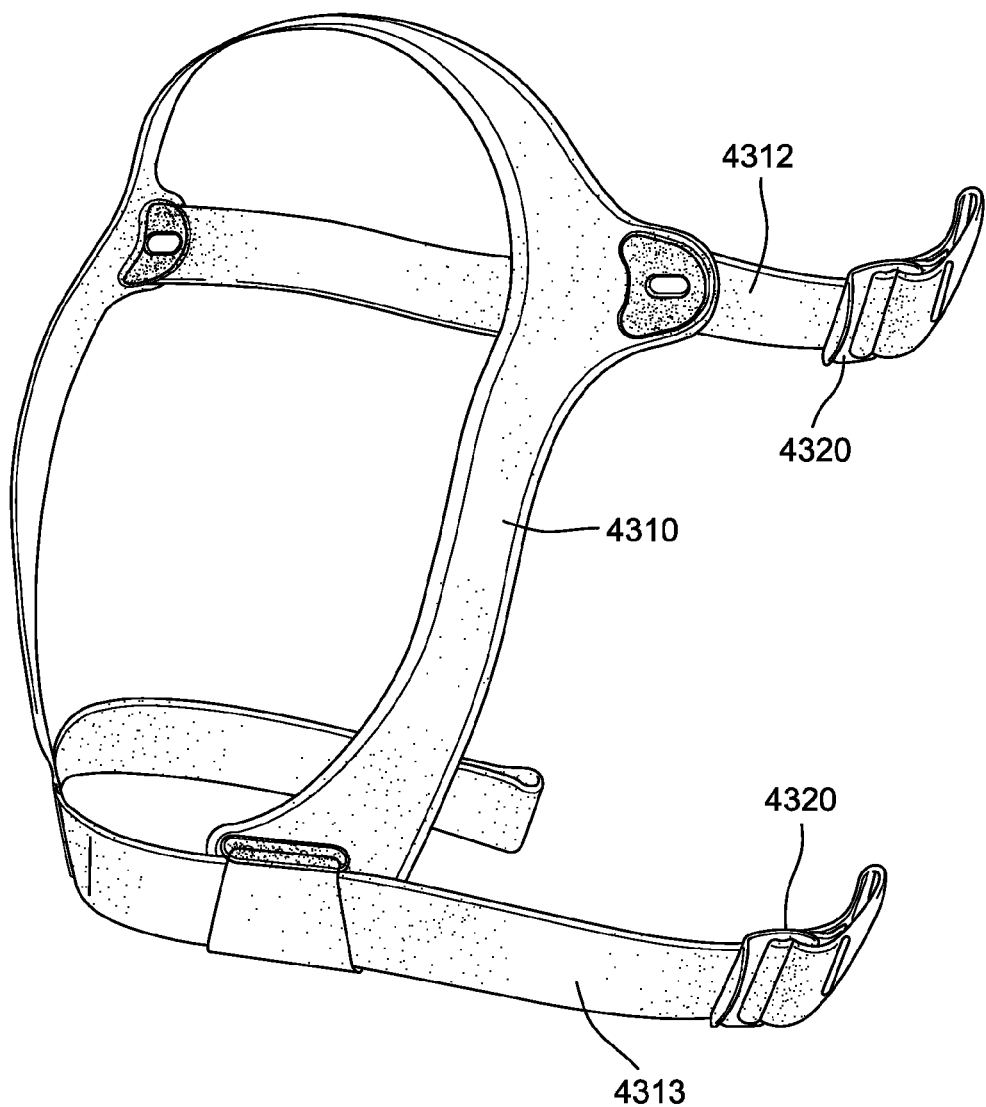
FIG. 24 is stylized perspective view of the assembled headgear according to a further embodiment of the present.

FIG. 24 shows a further embodiment where top strap 4312 and bottom strap 4313 may be adjustable with ladder locks 4320. Top strap 4312 and bottom strap 4313 may be attached to a first strap 4310 with an encapsulated rigidizer (not shown).

In an embodiment, one or more aspects of the headgear may be structured to prevent or at least reduce the chances of headgear riding up the patient's head and causing the straps to abut or touch underneath the patient's ears in use.

Figure 36:
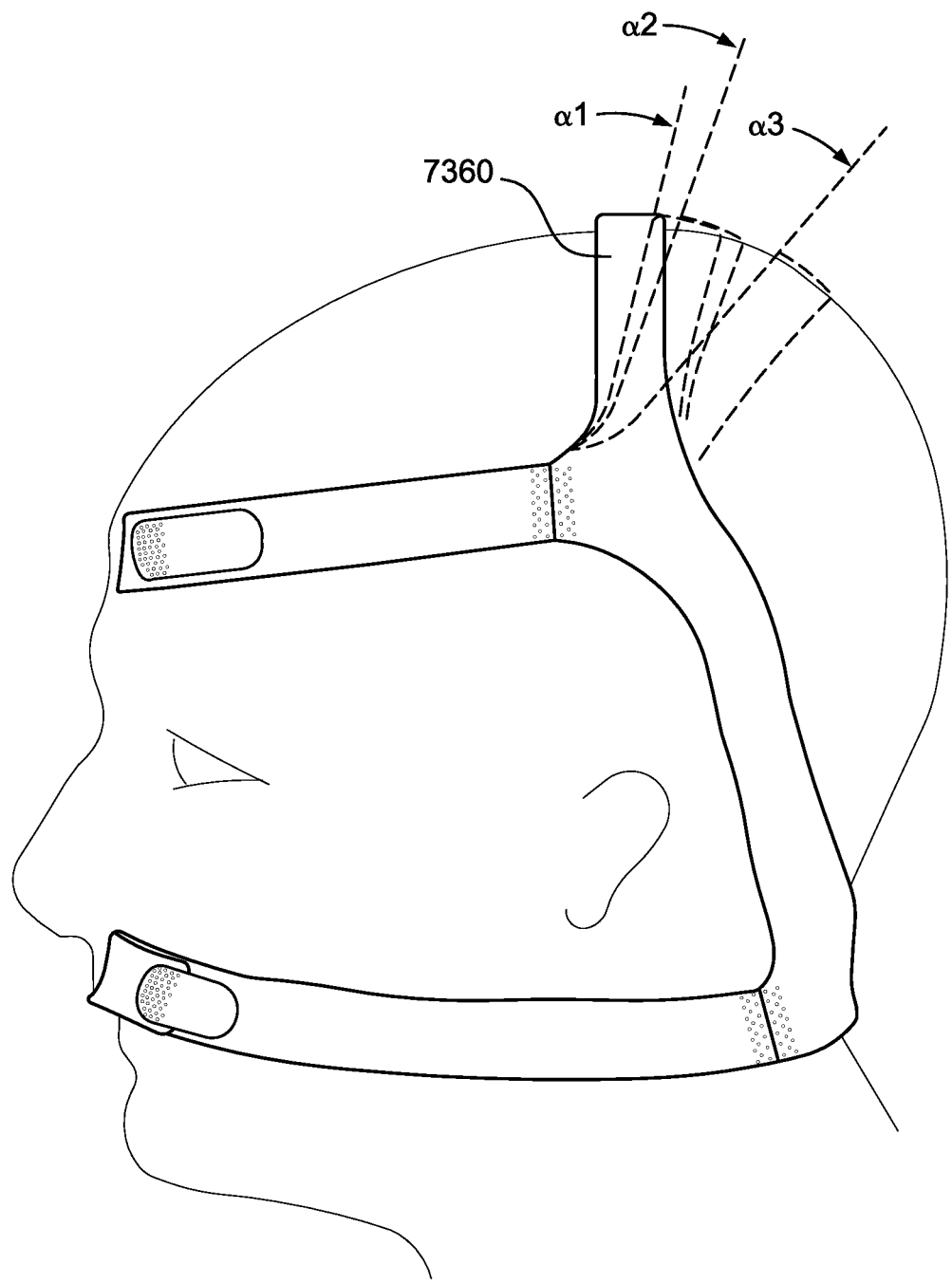
FIG. 36 shows alternative positions of the crown strap according to an embodiment of the present technology.
Figure 37:
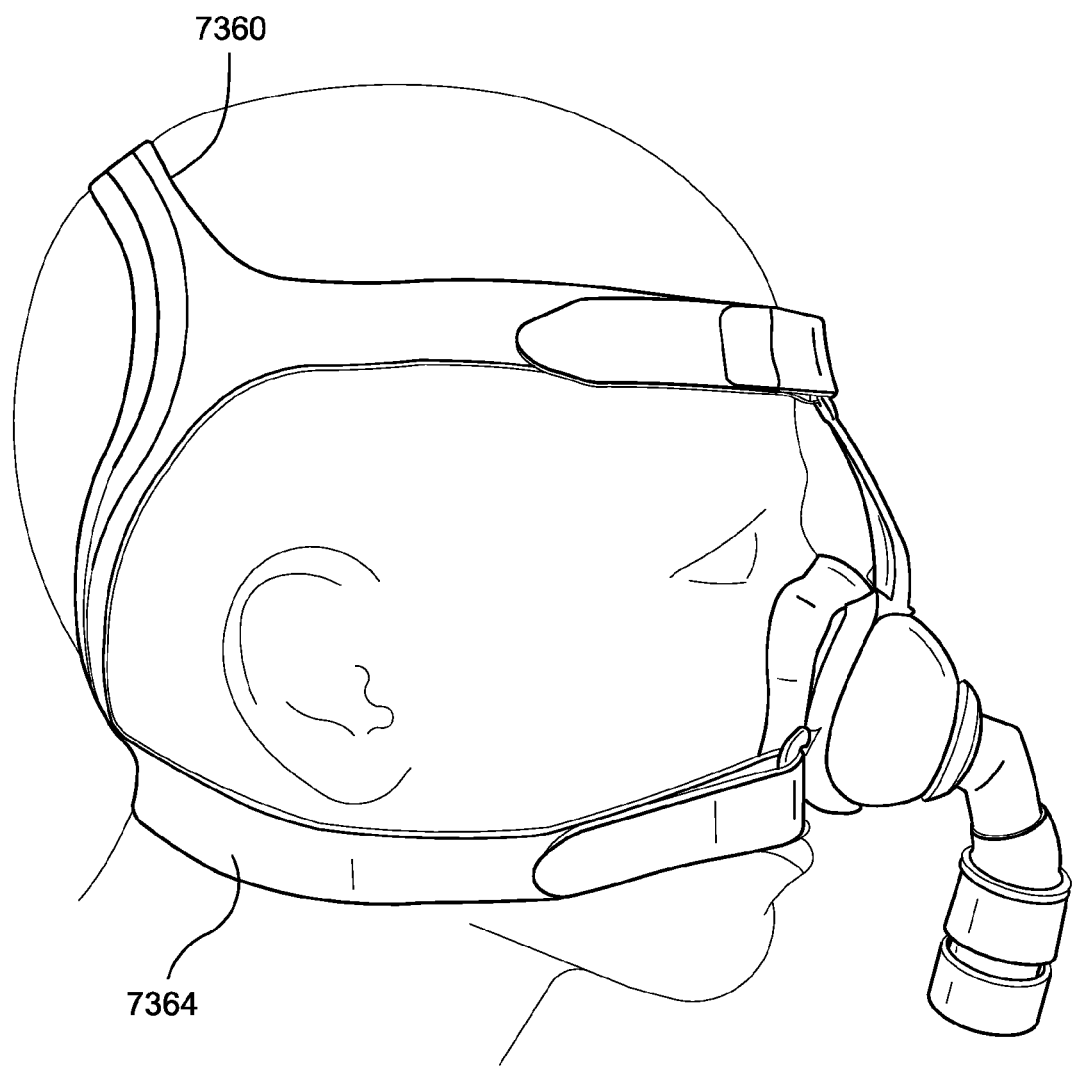
FIG. 37 shows an alternative position of the crown strap according to an embodiment of the present technology.

For example, as shown in FIG. 36, the position of the crown strap 7360 may be moved rearwardly (i.e., change the angle of the crown strap) to reduce the chances of headgear ride up. The original position of the crown strap 7360 is indicated in FIG. 36 by the solid line. The original position of the crown strap 7360 may be vertical direction or in the direction of the frontal plane of the body. In an example, the crown strap 7360 may be moved back by up to 40° from the position shown in FIG. 36, e.g., moved back 15° as indicated by α1, 20° as indicated by α2, and 40° as indicated by α3. Also, moving the crown strap rearwardly improves cradling in the crown region of the patient's head to enhance support, e.g., so crown strap is not too loose on the top of the patient's head. Furthermore the strap may include a curvature such as a J-shape, or a "dog leg" shape to direct a headgear vector around an ear, for example having a radius of approximately 50 mm to 70 mm, more preferably about 55 mm to about 65 mm, as shown in FIG. 36. FIG. 37 illustrates how the crown strap 7360 helps to maintain sufficient spacing of the lower strap 7364 from the patient's ear.

Figure 38:
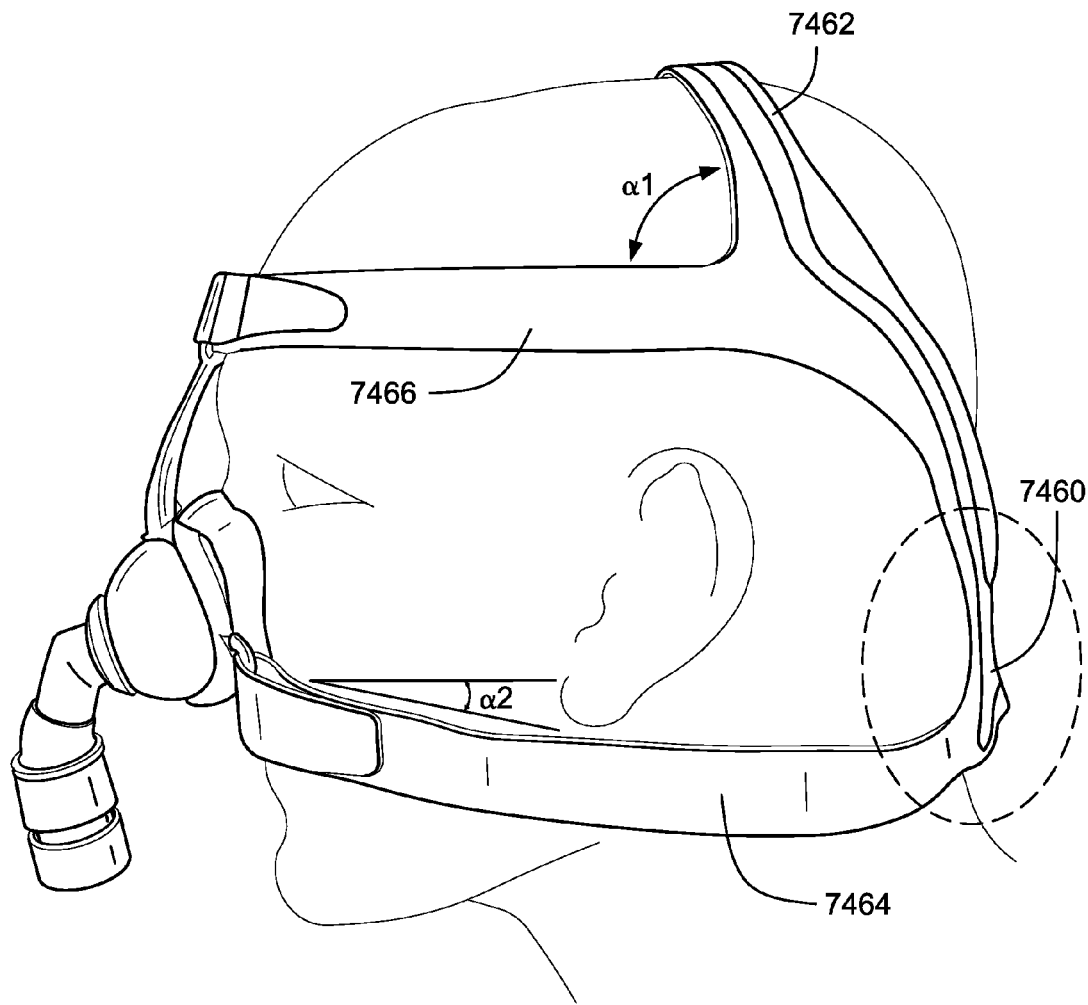
FIGS. 38 and 39 show headgear with a rigidizer according to an embodiment of the present technology.
Figure 39:
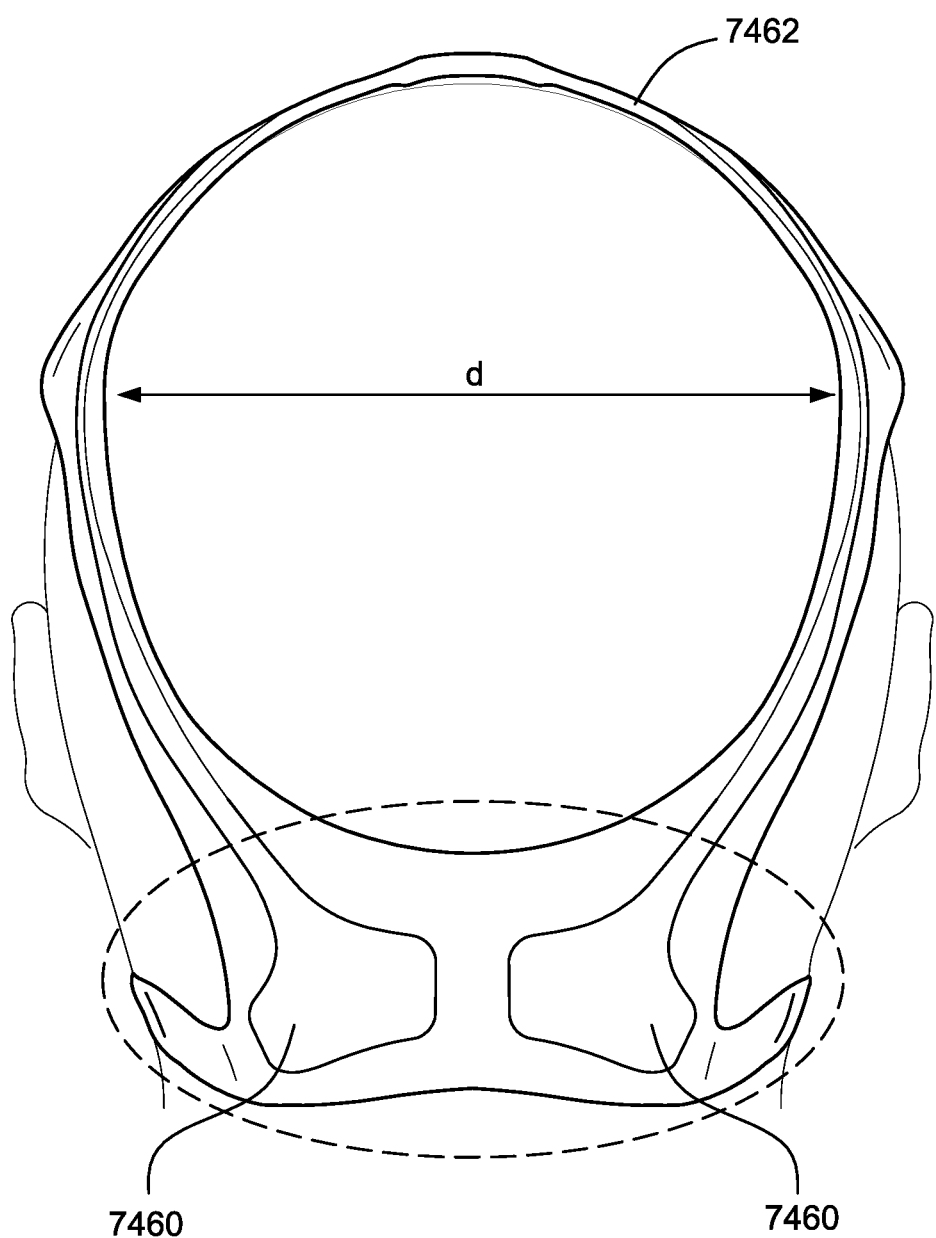

In another example, as shown in FIGS. 38 and 39, the rigidizer 7460 may be extended to enhance support along the bottom strap along the bottom of the neck. In addition, the length of the top strap 7466 may be extended to enhance the positioning of the crown strap. Preferably, the rigidizer 7460 may support or position the lower straps of the headgear underneath or out of contact with the patient's ears. Also, the rigidizer 7460 may prevent the headgear from riding up or translating vertically upwards on the patient's head, by securing the headgear at the occiput and/or neck of the patient. The inextensibility of the rigidizer 7460 also prevents the crown strap 7462 from being stretched into impinging on the patient's ears. The crown strap 7462 secures the headgear in position so that the headgear does not slide forward or around the patient's head. The bottom and top straps 7464, 7466 may be more elastic or extensible than the crown strap 7462.

In an example, as shown in FIGS. 38 and 39, the diameter d of the crown strap 7462 preferably may be about 500 mm, and the top strap 7466 may be oriented at an angle α1 of about 90° with respect to the crown strap. The lower strap 7464 may be oriented at an angle α2 of about 15-30°, e.g., 20°, down from horizontal. In a further example, the diameter d of the crown strap 7462 may be about 440 mm to about 600 mm. In a further example, the diameter d of the crown strap 7462 may be about 500 mm to about 600 mm. In a further example, the diameter d of the crown strap 7462 may be about 550 mm to about 600 mm. In a further example, the diameter d of the crown strap 7462 may be about 440 mm to about 550 mm. In a further example, the diameter d of the crown strap 7462 may be about 440 mm to about 500 mm. The diameter d defines a loop of a back portion of the headgear that circumscribes the rear of the patient's head such that little, or none, of the headgear is between the patient's head and the pillow or bed when the patient is lying on his/her back.

1.2.3 Rigidizer/Strap Adjustment

In an embodiment, adjustment of the rigidizers and headgear straps may be provided by hook and loop material (e.g., Velcro®), elastic, press studs, etc).

For example, in FIGS. 1-2 and 6-10, one or both ends of the straps 20, 30, 220, 230, 620, 630 include a Velcro® tab structured to engage the remainder of the strap to secure the strap in place and allow adjustment (e.g., with respect to the rigidizer and/or mask).

In FIGS. 1, 4, and 5, one or more straps 40, 440, 450, 540, 550 are in the form of an elastic component to allow adjustment.

Elastic provided to a top strap of a headgear (for example, top strap 3012 in FIG. 20) may be 250-450 mm in length. Preferably, elastic top strap may be about 320-400 mm. Preferably, elastic top strap may require no more than 10 N of force to stretch the elastic 100 mm from its original length. Preferably, elastic top strap may require no more than 6 N of force to stretch the elastic 100 mm from its original length. Preferably, elastic top strap may require no more than 4 N of force to stretch the elastic 100 mm from its original length. Preferably, elastic top strap may require no more than 3 N of force to stretch the elastic 100 mm from its original length. This may ensure the headgear is comfortable for a range of patient's head sizes.

In FIGS. 10-13, one or more straps include a press stud arrangement as described above to allow adjustment.

1.2.4 Rigidizer Material

The rigidizer may have composite construction with two or more materials (rigid or semi-rigid material with a covering constructed of a softer, patient contacting material), may be constructed of alternative fabric or polymeric materials (3D weave, knit, non-wovens, laminates), and may be manufactured in alternative manners.

For example, the rigidizer may be made from any flexible, conforming material such as nylon, polypropylene, polycarbonate, polystyrene, polyethylene, thermoplastic elastomer (TPE), thermoplastic urethane (TPU), silicone, polyester, etc (e.g., see FIG. 1). In FIG. 3, the rigidizer 360 is a 3D weave/knit with overlocked edges.

The rigidizer may also be constructed by thickening or treating a fabric such that it is stiffer or impedes the stretch of the material. For example, the fabric may be printed on such that the ink from the print restrains or reduces the capacity of the fabric to stretch. Additionally, the fabric may be stitched in selected regions to stiffen it. Also, the fabric may be ultrasonically welded in selected regions to stiffen it.

The rigidizer may be constructed from a non-woven material, for example netting, such that it is resistant to stretching in at least one direction.

The rigidizer may alternatively be formed from a woven material, where the grain of the material is aligned such that the fabric may not stretch in the lateral direction (when positioned on the patient's head) to secure and anchor the headgear in position on the patient's head.

The rigidizer may also be formed by a layer of additional material such as silicone, polyurethane or other tacky material, that may be applied to a fabric strap to reinforce the strap. Silicone beading or polymeric over molding may also be used.

The rigidizer may be 0.1 mm to 10 mm thick. Depending on the construction material of the rigidizer, the rigidizer may be preferably between 0.5 mm and 5 mm thick. Generally, the thinner rigidizers may result in more comfortable headgear for the patients. Thicker rigidizers may be the more dimensionally stable or rigid.

The rigidizer may be 1 mm to 30 mm wide. Preferably, the rigidizer may be 5-20 mm wide. Preferably, the rigidizer in some of the embodiments described herein may be 10 mm wide. To increase flexibility along the length of the rigidizer, the material may be thinner in its width than height, or narrower in its width for a thicker material.

In another embodiment, the rigidizer may have the same width or a width less than a fabric backing material. The fabric backing material is in contact with the patient's head in use. This is to increase the comfort of the headgear system in use.

In a further embodiment, the rigidizer may be encapsulated within a suitable fabric material to improve patient comfort and wearability.

The rigidizer may be overmolded (e.g., TPE overmolded with a softer material (e.g., see FIG. 10)) or formed separately and then a sock of patient contacting material (e.g., Breath-O-Prene™) may be wrapped or slid over the rigidizer (e.g., see FIGS. 2, 6, and 9). In alternative embodiments, the patient contacting material may be provided to the rigidizer by adhesive, ultra sonic welding, sewing, hook and loop material, and/or stud connectors. In an embodiment, the patient contacting material may only be on the patient contacting side of the rigidizer to reduce bulk and cost of headgear.

The resilient structure of the rigidizer may also improve the anchoring of the straps to it and may prevent the straps from tearing or ripping through the rigidizer under conditions of normal use by a patient.

Figure 14A:
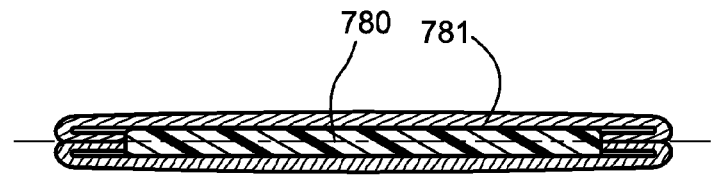
FIGS. 14A to 14J are cross-sectional views showing alternative materials and arrangements for a rigidizer according to embodiments of the present technology.

FIGS. 14A to 14G are cross-sectional views showing alternative rigidizer configurations. As shown in FIG. 14A, the rigidizer may include a die cut sheet material 780 that is covered in fabric 781, e.g., two pieces of fabric joined by stitching or gluing. Preferably, the joint of the fabric is within the strap, such that the joint is not able to contact the patient's face in use. This may be achieved by sewing the strap inside out and returning it to its intended orientation so that the stitching is within the pocket of the fabric. The fabric provides a softer material for contacting the patient's face in use. The softer material may also be suitable for the selective attachment of Velcro™ tabs. The fabric on the patient contacting side may be the same as the fabric on the non-patient contacting side. The fabric on the patient contacting side may preferably have the same weave as the fabric on the non-patient contacting side, such that the stretch characteristics of the straps are approximately equal on both sides. Also, it is preferred that the fabric on the patient contacting side have the same heat shrinkage characteristics as the non-patient contacting side. This is to prevent the headgear deforming unevenly when thermoformed or otherwise processed or exposed to heat. The fabric on the patient contacting side may be a different fabric to the non-patient contacting side, such that the fabric on the patient contacting side is more comfortable than the non-patient contacting side.

Figure 14B:
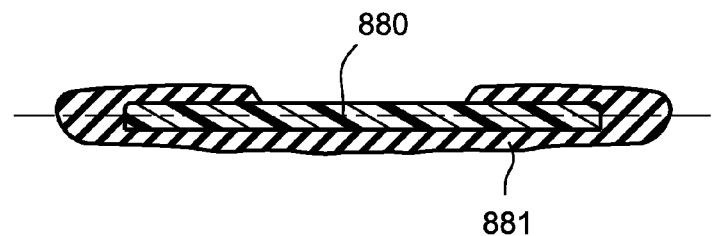

As shown in FIG. 14B, the rigidizer may include a die cut sheet material 880 that is overmolded with a soft polymeric material 881, e.g., TPE, TPU. The polymeric material provides a softer material for contacting the patient's face in use.

Figure 14C:
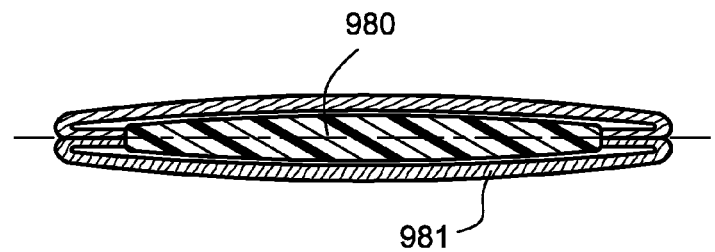

As shown in FIG. 14C, the rigidizer may include a semi-rigid molded component 980 that is covered in fabric 981, e.g., two pieces of fabric joined by stitching.

Figure 14D:
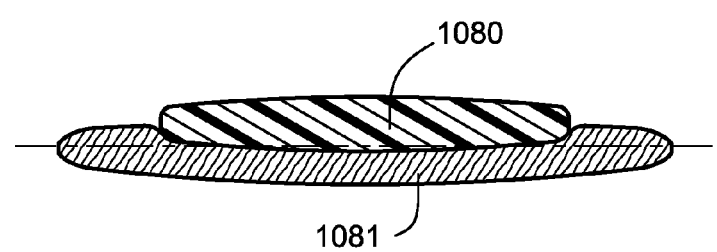

As shown in FIG. 14D, the rigidizer may include a semi-rigid molded component 1080 that is attached (e.g., welded, glued, overmolded) to a fabric composite material 1081 (e.g., Breath-O-Prene™ material or similar). The fabric composite material provides a softer material for contacting the patient's face in use.

Figure 14E:
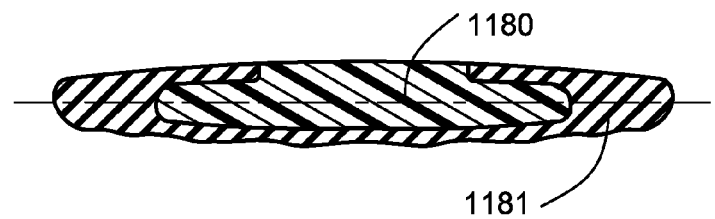

As shown in FIG. 14E, the rigidizer may include a semi-rigid molded component 1180 that is overmolded with a soft polymeric material 1181, e.g., TPE, TPU. The polymeric material provides a softer material for contacting the patient's face in use.

Figure 14F:

As shown in FIG. 14F, the rigidizer may include a soft molded component 1280 molded with a soft polymeric material, e.g., TPE, TPU. In an embodiment, the molded component may be provided with soft touch or flock coatings.

Figure 14G:
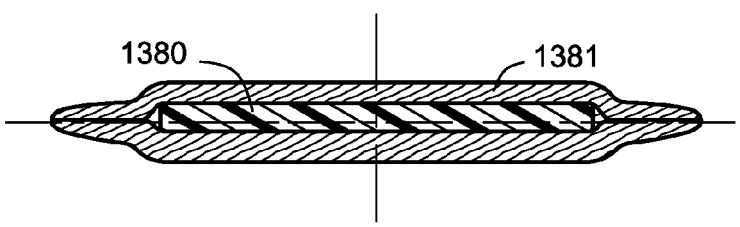
Figure 14H:
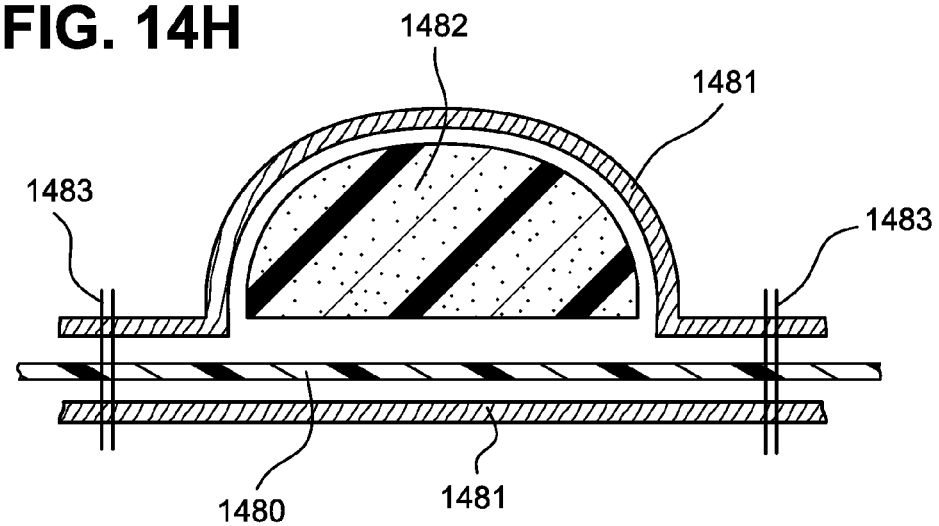

As shown in FIG. 14G, the rigidizer may include a fabric outer layer 1381 thermoformed and attached to a rigidizer 1380. The rigidizer may be a die cut sheet material. Alternatively, the rigidizer could be a molded part, machined part, or otherwise formed part. The fabric outer layers may be heat sealed together, stitched, ultrasonically cut, CNC knife cut, or otherwise joined. As illustrated, the fabric outer layer 1381 is joined at approximately the center or middle of the edge. Preferably, the joint is at the center or close to the center of the side of the headgear. Alternatively, the joint may be positioned away from the patient's face when in use. It is also possible to position the joint adjacent or close to the patient's face in use. Preferably, a layer of foam or other conformable material may be positioned around or about the rigidizer 1380. The foam may preferably extend to the lateral, horizontal edges of the rigidizer 1380 so as to prevent the ends of the rigidizer abutting the patient's face and causing discomfort or facial marking. For example, FIG. 14H illustrates a rigidizer 1480 with fabric outer layers 1481 and a foam layer 1482 provided along at least a portion of the rigidizer 1480. As illustrated, the foam layer 1482 positions the joints 1483 away from the patient's face when in use.

Figure 31:
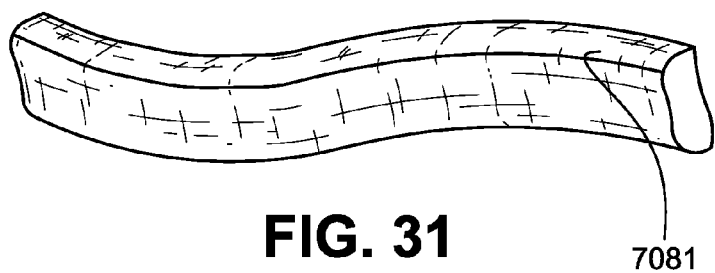
FIG. 31 is a perspective view of an ultrasonically cut headgear strap according to an embodiment of the present technology.

In an embodiment, the headgear strap may be thermoformed and then edges of the strap may be ultrasonically cut. The thermoformed and ultrasonically cut strap provides rounded edges 7081 (as shown in FIG. 31) which provides substantially reduced facial marking in use. In addition, the thermoformed and ultrasonically cut edges are softer and less abrasive, which provides a more comfortable feel on the patent's face in use, e.g., more comfortable feel around the patient's ears.

In a further embodiment, at least a portion of the headgear may be constructed from a spacer fabric, where the edges of the spacer fabric may be ultra sonically welded. This may cause the edges of the spacer fabric to be rounded, thereby reducing facial marking and increasing comfort for the patient.

Figure 14I:
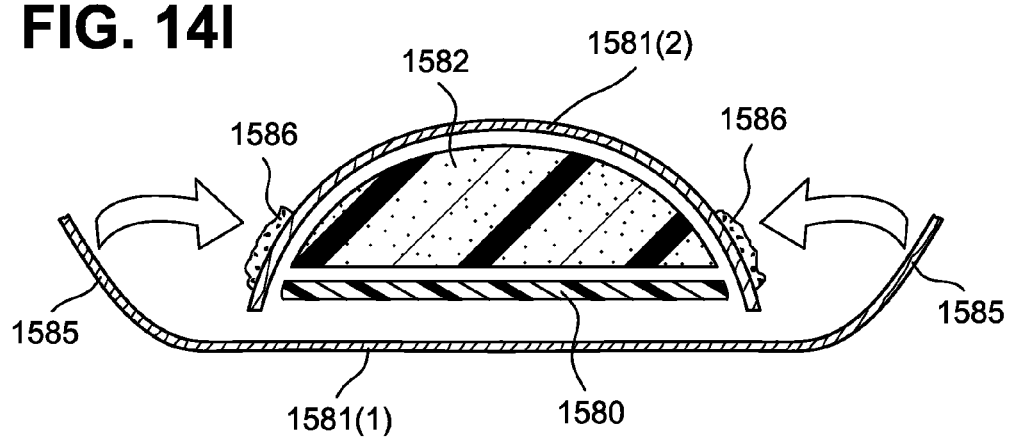
Figure 14J:
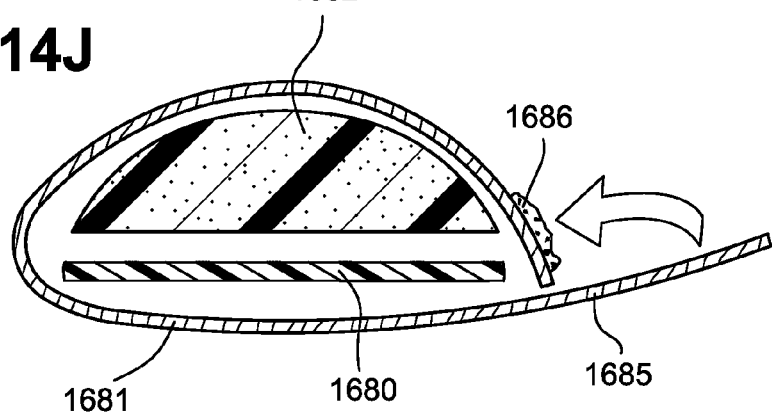

In an alternative embodiment, the fabric outer layers may be attached together by adhesive. For example, as shown in FIG. 14I, a first layer of fabric 1581(1) may have wings 1585 positioned at one or both ends. Adhesive 1586 (e.g., glue) may be positioned on ends of a second layer of fabric 1581(2), such that the wings 1585 can be folded onto the adhesive to seal the inner portions of the headgear within the fabric layers. As illustrated, the inner portions of the headgear may include a conformable material such as foam 1582, or a rigidizer 1580, or a combination of the two. Alternative internal components may include other elements disclosed herein, such as 3D weaves. It should further be appreciated that the adhesive and wings may be positioned in alternative arrangements, such as the adhesive positioned on the wings, or the wings positioned on the second layer of fabric. It is further possible for the first and second layers of fabric to be a single, continuous piece of fabric that is sealed at one end by a wing and adhesive arrangement. For example, FIG. 14J shows a single piece of fabric 1681 including a wing 1685 at one end that is adapted to be folded onto adhesive 1686 (e.g., glue) at the other end. As illustrated, the inner portions of the headgear include a conformable material such as foam 1682 and a rigidizer 1680.

Preferably, the edges of the headgear are completely closed, that is, the interior components of the headgear (such as the rigidizer and conformable material) are completely contained within the fabric outer layers. This is to avoid hair tangling in the internal components or discomfort due to contact with the interior elements. In addition, it may be easier to maintain the cleanliness and durability of the system if the internal components are completely encapsulated or contained within the fabric layers.

Preferably, the edges where the fabric layers meet one another are sealed or otherwise hidden to avoid the fabrics from parting or becoming dislodged. This arrangement may also be preferable for creating a rounded continuous edge. See FIG. 14A for example.

In an embodiment, one or more aspects of the headgear strap may be structured to enhance comfort of the crown strap (i.e., the strap adapted to pass over the top of the patient's head in use). For example, the rigidizer may be relatively thin, e.g., less than 1 mm such as 0.5 mm or 0.8 mm. In another example, the strap may include a nylon rigidizer enclosed in foam. In such embodiment, the density of the foam may be increased to improve comfort and reduce chances of feeling the nylon rigidizer. Alternatively, the thickness of the foam may be utilized to alter the softness or roundness of the edge of the headgear. For example, thicker layers of foam are more likely to produce rounder corners than thinner layers of foam. In a further embodiment, the foam may begin at one thickness, and be compressed to another thickness during processing. The first thickness of the foam may be 5 to 30 mm. Preferably, the first thickness may be 7 to 12 mm. Alternatively, the first foam thickness may be 10 to 20 mm. The second foam thickness may be 0.1 to 10 mm. Preferably, the second foam thickness may be 2 to 5 mm. The second foam thickness may alternatively be 3 to 7 mm.

Figure 32:
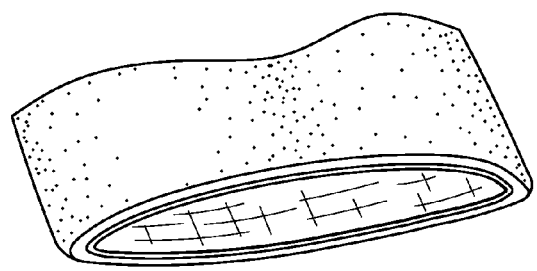
FIG. 32 is a perspective view of a headgear strap constructed of non-woven material according to an embodiment of the present technology.

In another example, a non-woven material (e.g., such as that shown in FIG. 32) may be used for the crown strap because it may be more rigid or less flexible than a woven material, e.g., business shirt collar stiffener is a non-woven material.

Figure 33:
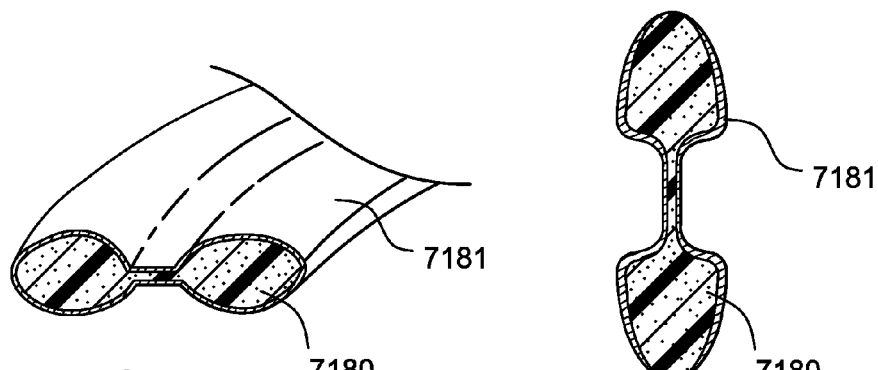
FIGS. 33 and 34 show a fabric headgear strap with a foam interior according to an embodiment of the present technology.
Figure 34:
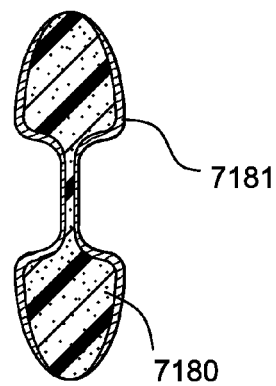

In another example, the rigid component may be removed from the crown strap and as an alternative a fabric crown strap 7181 may be heat pressed or embossed with a foam inner 7180 to melt the foam and create a stiffened region (see FIGS. 33 and 34). In an example, a thermoformed rib may be formed by compressing the foam by about 80%.

Figure 35:
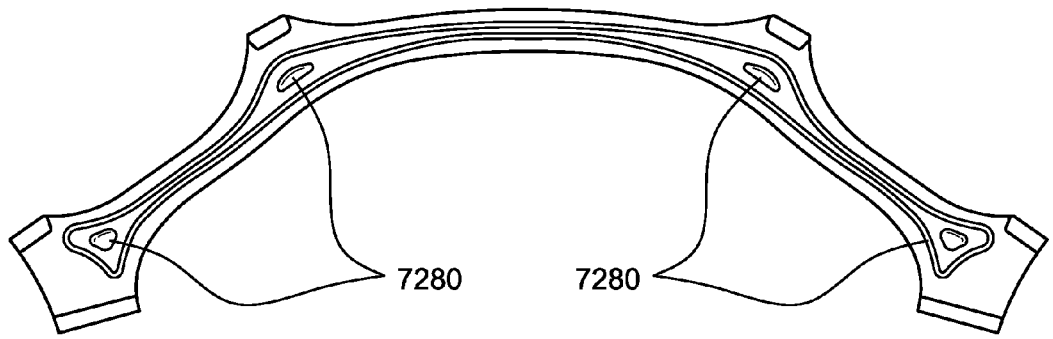
FIG. 35 shows a method of rigidising with embossed ribs according to an embodiment of the present technology.

In another example, multiple ribs 7280 may be embossed into the rigidizer to reduce visual bulk and add rigidity, as shown in FIG. 35.

Also, the rigidizer may include embossed ribs or other features to encourage flex or control movement of the headgear in specific regions. In addition, embossing may be used to stamp on a branding logo.

In an example, the headgear strap may include two layers of foam. However, other suitable configurations are possible, e.g., 1, 2, 3, or more layers of foam. In an embodiment, foam on the patient contacting side may be less dense or have a lower hardness than foam on non-patient contacting side. It is also possible to have more than one layer of foam and more than one rigidizer component. Alternatively, the headgear may comprise more than one rigidizer and a single layer of foam.

In an example, non-woven material may be inserted in-between additional foam or fabric layers in place of a nylon rigidizer.

In an embodiment, the materials and/or headgear configuration may be selected to reduce costs.

2.0 Manufacturing

Preferably, the method of manufacturing the headgear may reduce costs by maximizing volume and eliminating material wastage. For example, components may be shaped such that they can be nested closely on the bulk material such that when die cut into individual components, waste is reduced waste thereby reducing cost.

Figure 41:
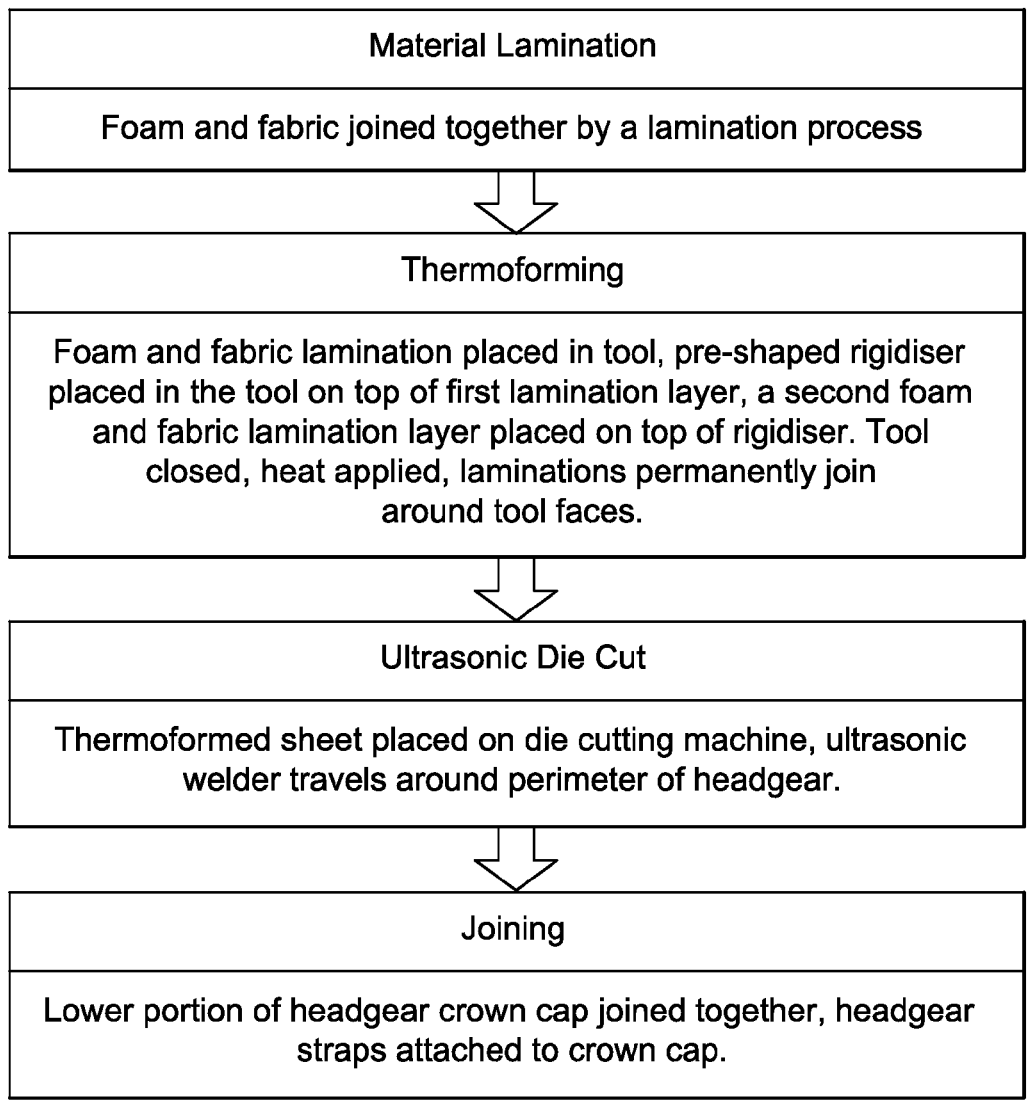
FIG. 41 shows an exemplary process for creating rigidized headgear according to an embodiment of the technology.
Figure 42:
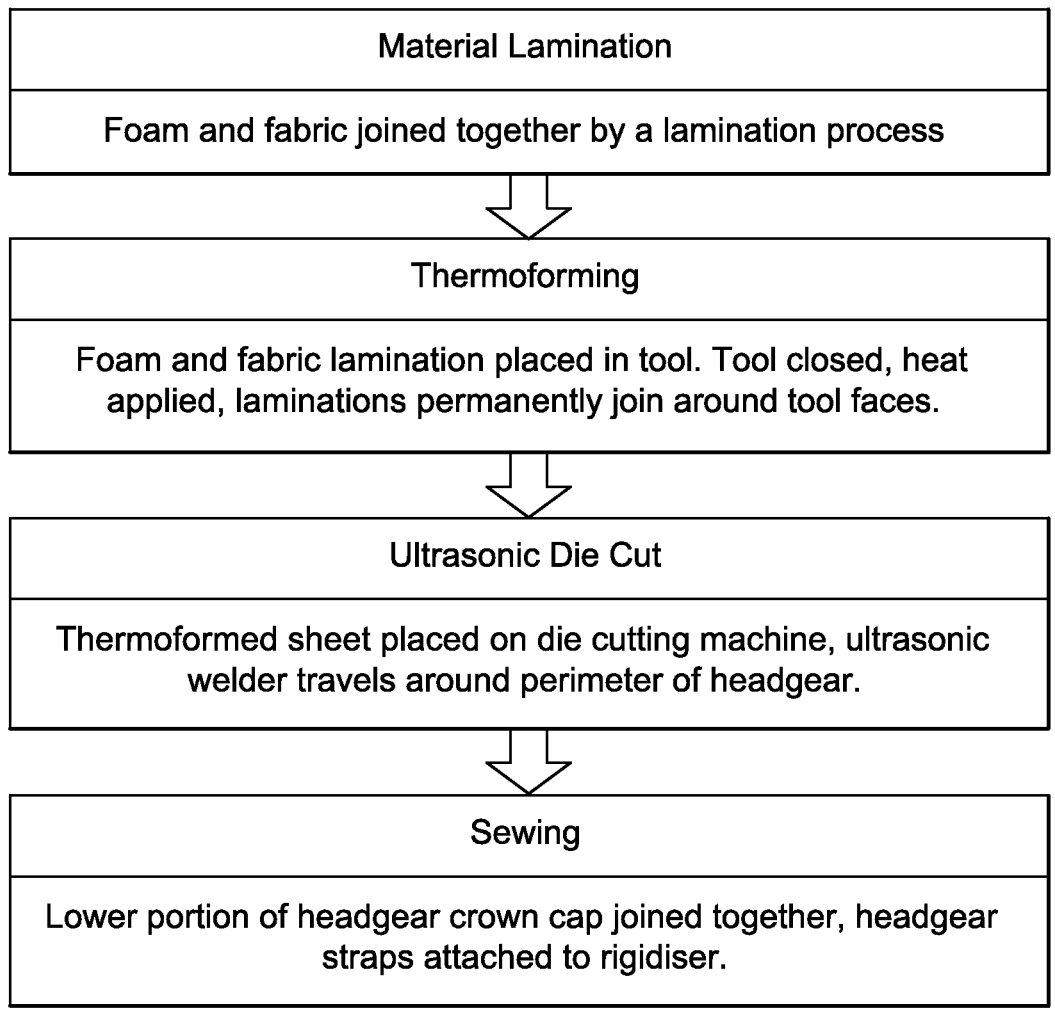
FIG. 42 shows an exemplary process for creating non-rigidized headgear according to an embodiment of the technology.

FIGS. 41 and 42 show exemplary processing steps for creating headgear as described. Alternative manufacturing steps are also possible.

For example, FIG. 41 shows an exemplary process for creating rigidized headgear. This exemplary process includes material lamination (foam and fabric joined together by a lamination process), thermoforming (foam and fabric lamination placed in tool, pre-shaped rigidizer placed in the tool on top of first lamination layer, a second foam and fabric lamination layer placed on top of rigidizer; tool closed, heat applied, laminations permanently join around tool faces) ultrasonic die cut (thermoformed sheet placed on die cutting machine, ultrasonic welder travels around perimeter of headgear), and joining (lower portion of headgear crown cap joined together, headgear straps attached to crown cap). In one process, the lamination step may be omitted. In another process the thermoforming and ultrasonic cutting may be completed in one step.

FIG. 42 shows an exemplary process for creating non-rigidized headgear. This exemplary process includes material lamination (foam and fabric joined together by a lamination process), thermoforming (foam and fabric lamination placed in tool; tool closed, heat applied, laminations permanently join around tool faces), ultrasonic die cut (thermoformed sheet placed on die cutting machine, ultrasonic welder travels around perimeter of headgear), and sewing (lower portion of headgear crown cap joined together, headgear straps attached to rigidizer).

Figure 16A:
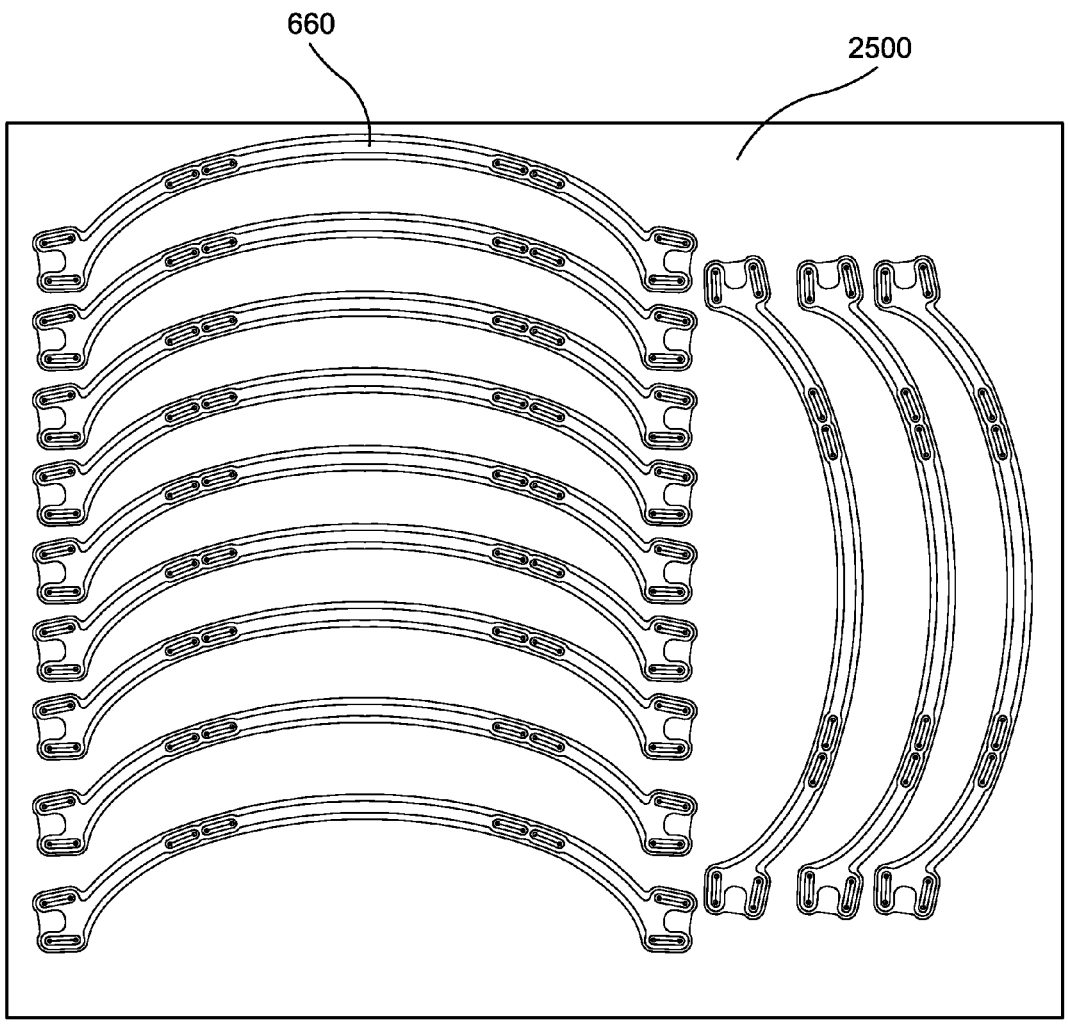
FIG. 16A shows an example of a relatively high or improved yield nested headgear components.
Figure 16B:
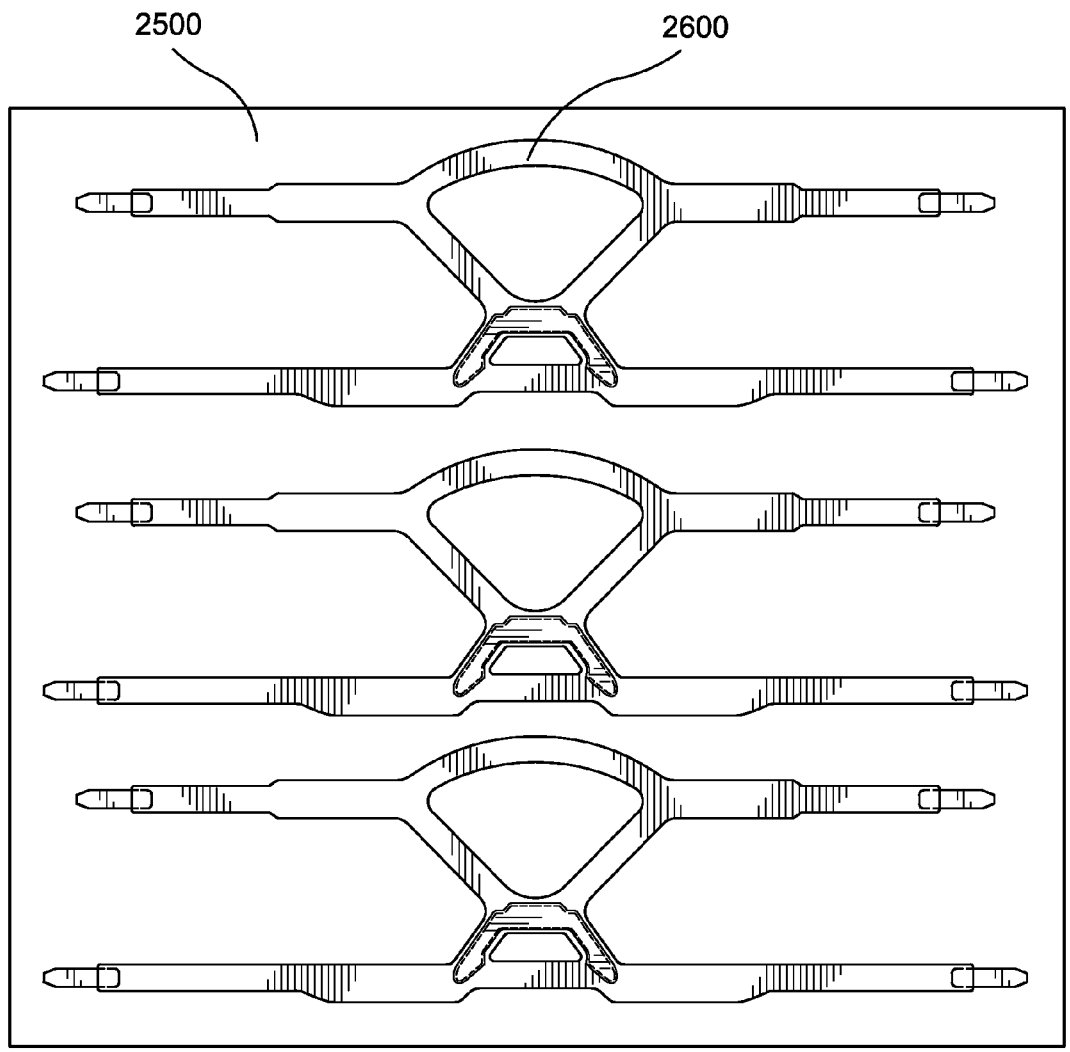
FIG. 16B shows a prior art example of low yield nested headgear components using a prior art method of manufacture.

As illustrated in FIG. 16A, a headgear component 660 in accordance with the present technology may be arranged for die cutting from a sheet. In the example of FIG. 16A, twelve headgear components 660 may be cut from a single sheet 2500 of fabric material. The headgear components 660 shown in FIG. 16A may be joined to a set of relatively straight straps that may also be efficiently nested (not shown), the combination making a complete headgear assembly. By way of contrast to a prior art configuration shown in FIG. 16B, only three headgear assemblies 2600 may be cut from a similarly sized sheet 2500 of a different design as shown in FIG. 16B. The manufacturing yield of FIG. 16B is approximately 11.5 headgears per meters$^2$. For purposes of this specification, "high manufacturing yield" is defined as any and all manufacturing yields higher than 11.5 headgears per meters$^2$.

In contrast to other prior art headgear configurations, such as the ResMed Quattro™ headgear, embodiments shown are constructed from multiple components that when separate, are simple geometric shapes that can be nested easily. For example, in the embodiment shown in FIG. 6, the upper headgear strap 620 and lower headgear strap 630 are substantially straight, rectangular components that could be nested and cut from a bulk piece of material without waste. Alternatively, upper headgear strap 620 and lower headgear strap 630 could be formed from woven materials and cut to length without waste. Rigidizer 660 may be formed from a flat piece, such as that shown in FIG. 15. In such a configuration, multiple rigidizers could be formed from a single bulk sheet of the rigidizer material with minimal waste as the rigidizers can be nested close together as shown in FIG. 16A. The Rigidizer 660 has a generally arcuate shape, but could be regarded by a person skilled in the art as a relatively simple geometric shape.

This is in contrast with prior art headgear such as the ResMed Quattro™ headgear, as such a shape can be nested closely but waste is generated due to the general shape of the headgear (i.e., apertures or holes in the headgear that must be stamped out).

A further embodiment is depicted in FIGS. 17-20. FIG. 20 depicts an assembled headgear 3015 for use attaching medical equipment to the head of a patient. In this embodiment, the preferred medical equipment is the mask of a CPAP machine.

The depicted headgear 3015 is adapted to mount a face mask on the face of a patient. The headgear 3015 comprises first 3010, second 3012, and third 3013 straps. The second 3012 and third 3013 straps are attached to the first strap 3010 by attachment means, which comprises a series or plurality of holes or apertures in the first strap 3010 adapted to receive the other straps. The second 3012 and third 3013 straps may be fixed or connected to the first strap 3010 by the use of one or more Velcro™ tabs adapted to loop back onto the original strap and attach to the preferably soft fabric material on the outer surface of the straps. Preferably, the Velcro™ tabs and the soft fabric used in the straps could selectively engage each other in "hook and loop" attachment common to the use of Velcro™.

Figure 17:
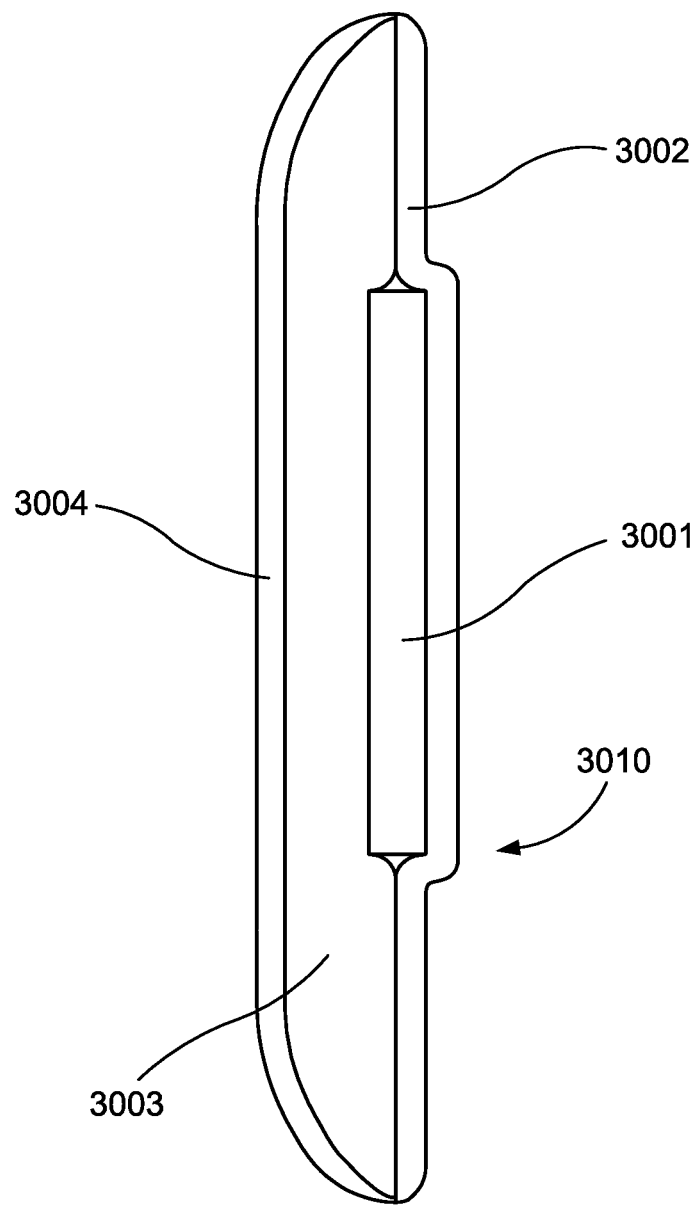
FIG. 17 is a cross-sectional view of a portion of a strap according to a further embodiment of the present technology.

The first strap 3010 comprises a construction shown in FIG. 17 and FIG. 18. A rigid or semi-rigid layer 3001 of resilient material is encapsulated between a first 3004 and a second layer 3002 of soft fabric material. Preferably, the soft fabric is adapted to be biocompatible, as in use, the layers 3002 and 3004 may contact the skin layer of the patient. Biocompatibility and softness may both reduce skin irritation to the patient.

Encapsulated between the rigid layer 3001 and the first soft fabric layer 3004 is a layer of cushioning 3003. Preferably, this cushioning layer 3003 is constructed a soft foam like material. In use, the first strap 3010 is preferably adapted to contact the skin layer of patient by contact with the first soft fabric layer 3004. The layered configuration of the first strap 3010 as depicted in FIG. 17 may only be required to extend along a portion of one of the straps to function correctly as disclosed in this embodiment.

Preferably, the layers of the first strap 3010 may be attached to each other by vulcanization or gluing. Additionally, the first fabric layer 3004 and second fabric layer 3002 are not required to be of the same or identical material and may be substitute to improve the aesthetic appearance of the headgear 3015.

In this embodiment, the second strap 3012 and third strap 3013 may be entirely constructed of soft fabric material to improve comfort. However, other strap configurations are possible.

The rigid layer 3001 or rigidizer may preferably be constructed of polycarbonate, Lexan™ or similar resilient material of about a thickness of 1-2 mm. The soft fabric material may be Breath-O-Prene™ or other soft fabric material including but not limited to nylon or Spandex™.

Preferably, the first strap 3010 may function as a rigidizer within the overall headgear assembly or configuration 3015 as shown in FIG. 20. One advantage with including a rigidizer within this construction is that it may allow for equalized distribution of pressure around the patient's head, particularly, when mounted in the configuration shown in FIG. 20. This embodiment may increase patient comfort by the rigidizer being mounted around or on the posterior of the patient's head.

Figure 19:
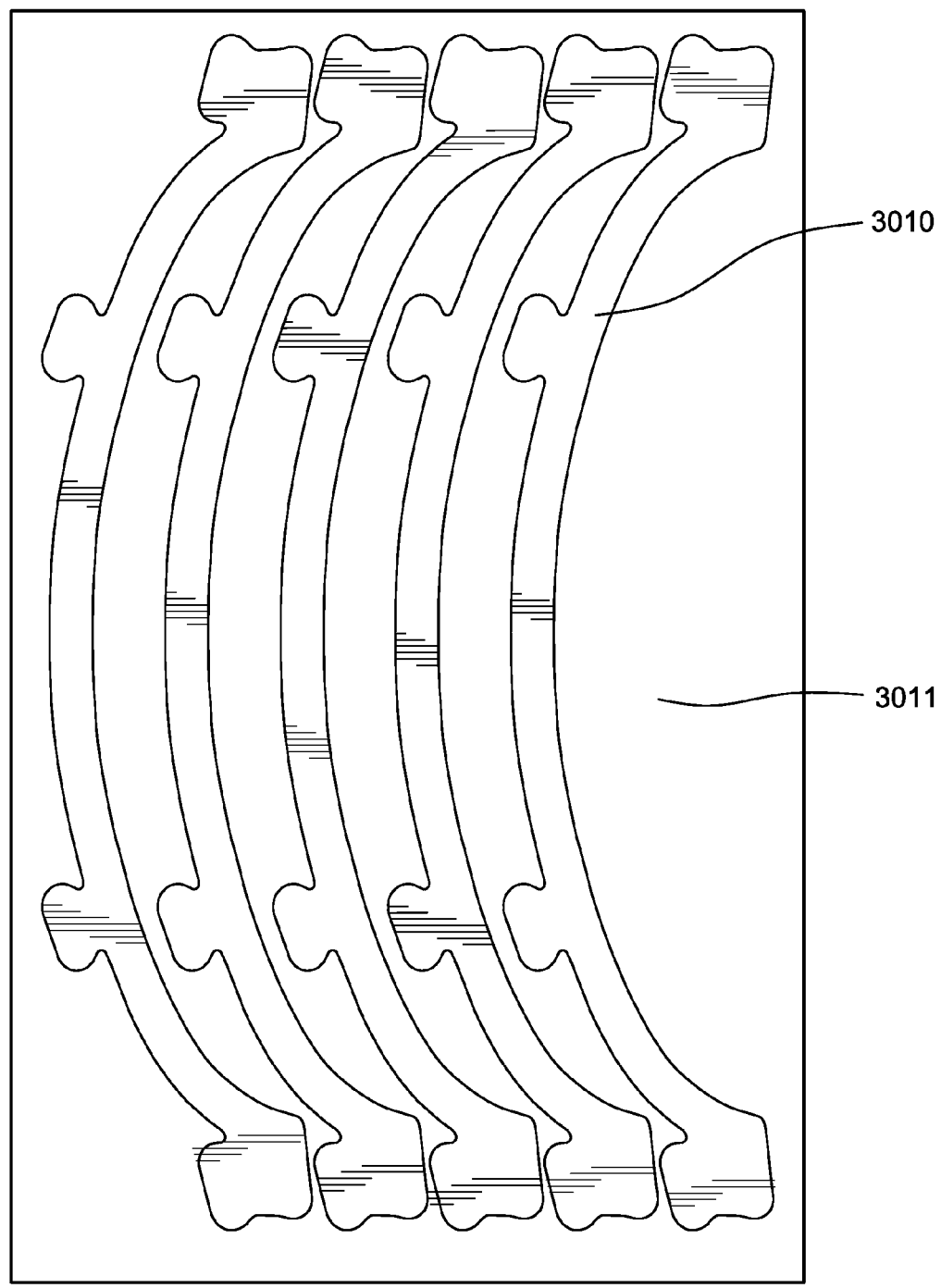
FIG. 19 is a top view showing a bulk sheet of material used in the manufacture of the embodiment depicted in FIG. 17.

Of further advantage in this embodiment, the construction of the straps may be optimized to reduce wastage. Previously, straps of headgear were constructed by cutting the entire headgear from a single bulk piece of material, which created a relatively large amount of waste material. FIG. 19 depicts a plurality of straps to be cut out of a bulk piece of manufacturing material. As depicted, the second layer 3002 of soft fabric material of the first strap 3010 is shown within a bulk sheet 3011 of material. In this example, the wastage is limited and minimized by nesting each of the component straps closely together on the same bulk sheet 3011.

In a further embodiment, an inner layer of foam may be molded, such that a skinned foam is formed in the shape of the headgear. Alternatively, any foam (skinned, unskinned or partially skinned) may first be formed or otherwise shaped to the shape of the headgear. Fabric may then be laminated onto the foam layer.

In a further alternative embodiment, a fabric or textile may be placed within a mold and a polymer or other such moldable material may be injected onto the fabric to the desired shape of the headgear.

In a further embodiment, the fabric outer layer may be filled with gel, air and/or other gas. The gas may be selectively filled in pockets with varying volumes in each pocket to influence the rigidity or support provided by that section of the headgear. The fabric outer layer may need to be gas tight, so may for example be laminated with an impermeable polymer layer.

Figure 43:
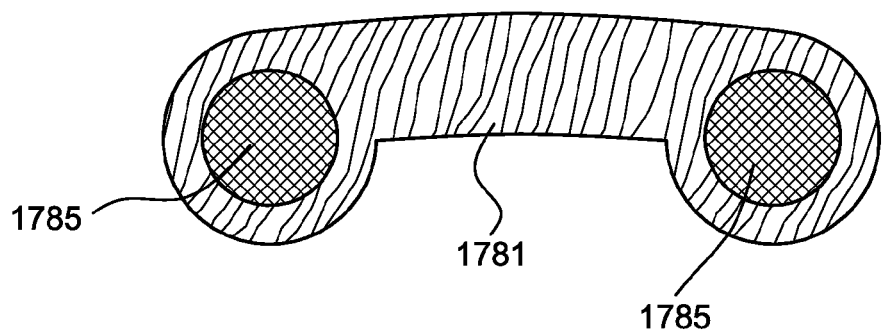
FIG. 43 shows headgear including an outer layer of fabric formed around or over two cords of material according to an embodiment of the technology.

In a further alternative embodiment, the outer layer of fabric may be formed around or over two cords of material. The cords of material are intended to create a round edge at the sides of the material. For example, FIG. 43 shows a cross section through a proposed headgear or portion thereof, wherein the cords 1785 provided within the outer fabric layer 1781 are rounded sections of material. The cords may be provided to both sides (as shown) or may be provided to just one side of the headgear strap. The cords may be constructed of foam, gel, polymer, or any other conformable material. The cords may have alternative shapes, for example they may have an ovoid or elliptical cross section. The cords are further shown as being separate (that is, not joined together through the center portion of the headgear section), however it is possible for the cords to be connected to one another.

It should also be appreciated that the foam outer layer may also be constructed of a single piece of material that is continuously weaved to make a tube of fabric.

It should be appreciated that while this technology has been described in relation to a headgear for a mask system, this technology may be applicable to other portions of the mask system, such as forehead pads, mask cushions, comfort pads, tube wraps, comfort socks, chin straps, mask frames or any other suitable portion of the mask system.

It is possible for a quick release mechanism to be attached to the headgear, for example a selectively releasable portion at the rear of the headgear. This may include a hook and loop material connection with a pull cord. Alternatively, the quick release mechanism may be a clip or any other mechanism to allow the patient to remove the mask system in an emergency.

In a further embodiment, it is possible for a tube mounting component to the attachable or formed with the headgear. For example, a strap for wrapping around a tube may be provided to the headgear, that may be attached to the tube by a hook and loop connection. Alternatively, clips or rings may be attached or formed with the headgear for engagement with a tube.

The rigidizer may also be formed from a selectively adjustable shape changeable material. For example, the rigidizer may be formed from a metal such that the patient can adapt the shape of the headgear to their desired position. It may also be possible to form the rigidizer from a heat deformable material, such that the headgear may be heated and positioned on the patient's head, and then taking on the form or shape of the patient's head. When the headgear is cooled, it may retain this shape. The rigidizer may also be formed of a malleable material, such as nitinol, that is able to be shaped.

The headgear may also be provided with pockets or gaps for inserting additional material or removing material. This may be provided so that the patient can alter and adapt the stiffness or comfort of the headgear in specific regions. For example, a pocket or space may be provided to the rear of the headgear so that the patient can add padding or conformable materials to this portion of the headgear.

In a further embodiment, the headgear may be provided with socks or wraps of padded or soft material to provide the patient with additional comfort should they require it. The socks or wraps may be selectively attachable to the headgear straps, for example by clipping, hook and loop material, pulling over or any other reasonable attachment method.

It may also be possible to provide the headgear with sensors for diagnosing or monitoring the patient.

In an alternative embodiment, the above described rigidizer may be replaced or supplemented with one or more elements possessing substantial inextensibility and/or resilience. For example, instead of using the above described rigidizer, stitching or embossing may be used to create a substantially inextensible structure. Furthermore, a non-rigid spring structure may provide resilience.

While the technology has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A respiratory mask assembly for treatment of sleep disordered breathing in a patient, comprising:
    a mask frame;
    a cushion provided to the mask frame; and
    a headgear system having a rear portion having a closed rear loop to engage and circumscribe the back of the patient's head, a pair of upper straps attached to the rear loop via stitching, and a pair of lower straps attached to the rear portion via stitching, the upper and lower straps being adjustably connected to the mask, the upper straps being connected to an upper part of the mask frame and the lower straps being connected to a lower part of the mask frame via clips,
    wherein the upper straps are relatively more extensible than the lower straps, the rear strap loop is inextensible compared to each of the upper straps, and the headgear system has at least one strap that is substantially inextensible,
    wherein each of the upper straps, lower straps and rear portion is constructed from a laminate having at least a first fabric layer and a second fabric layer, said first fabric layer being constructed and arranged to be located on a patient-contacting side in use, and said second fabric layer being constructed and arranged to be located on a non patient-contacting side in use, and further wherein said first fabric layer and said second fabric layer are joined at a joint configured to be positioned away from the patient's face when in use, and wherein each of the upper straps, the lower straps and the rear portion has a first rounded lateral edge when viewed in cross-section, and
    wherein each said joint is positioned at approximately a center or middle of the first rounded lateral edge when viewed in cross section.

2. The respiratory mask assembly of claim 1, wherein the laminate comprises a layer of resilient material between the first fabric layer and the second fabric layer.

3. The respiratory mask assembly of claim 1, wherein the laminate comprises a layer of rigid material between the first fabric layer and the second fabric layer.

4. The respiratory mask assembly of claim 1, wherein the laminate comprises a layer of semi-rigid material between the first fabric layer and the second fabric layer.

5. The respiratory mask assembly of claim 1, wherein the laminate further comprises a foam layer.

6. The respiratory mask assembly of claim 5, wherein said foam layer is positioned between said first fabric layer and said second fabric layer.

7. The respiratory mask assembly as claimed in claim 1, wherein each of the upper and lower straps includes a second rounded lateral edge, opposite said first rounded lateral edge, as seen in said cross section.

8. The respiratory mask assembly of claim 1 wherein the rear loop is configured to engage a back of a patient's head in a substantially circular or oval shape, the rear loop having at least a portion that is substantially inextensible.

9. The respiratory mask assembly of claim 1, wherein the rear portion comprises an arcuate region constructed to resiliently return to a predetermined curved shape to substantially match a portion of the patient's head when not in use.

10. The respiratory mask assembly of claim 1, wherein the rear portion comprises a substantially inextensible portion and is configured to be located at the upper half of the patient's head while in use.

11. The respiratory mask assembly of claim 1, wherein the a rear portion configured to engage a back of a patient's head and extend on either side of the patient's parietal bone behind the patient's ears and assume, in use, a substantially circular or oval shape.

12. The respiratory mask assembly of claim 1, wherein the lower straps are configured to extend below the patient's ear in use, the lower straps including a hook and loop material tab for attachment to the clips.

13. The respiratory mask assembly of claim 1, wherein the upper straps are configured to extend above the patient's ear in use, wherein each of the upper straps includes a hook and loop material tab for attachment to the mask frame.

14. The respiratory mask assembly of claim 1, wherein the headgear system comprises a portion that is configured to maintain a three dimensional shape when not in use so that orientation of the headgear is self-evident to the patient.

15. The respiratory mask assembly of claim 1, wherein the first fabric layer and the second fabric layer are stitched in a region to stiffen the at least the rear strap portion.

16. The respiratory mask assembly of claim 1, wherein the first fabric layer and the second fabric layer are ultrasonically welded in a region to stiffen at least one strap of said upper straps, said lower straps or said rear portion.

17. The respiratory mask assembly of claim 1, wherein the first fabric layer and the second fabric layer are compressed in a region to stiffen at least one strap of said upper straps, said lower straps or said rear portion.

18. The respiratory mask assembly of claim 1, wherein the first fabric layer and the second fabric layer are thickened or treated in a region to stiffen at least one strap of said upper straps, said lower straps or said rear portion.

19. The respiratory mask assembly of claim 1, wherein a stiffened region provides the rear loop with a three dimensional shape substantially matching a shape of the patient's head when not in use.

20. The respiratory mask assembly of claim 1, wherein the lower straps are angled downwardly with respect to a horizontal plane to guide the lower straps below the ears of the patient.

21. The respiratory mask assembly of claim 20, wherein the upper and lower straps are thermoformed and ultrasonically cut.

22. The respiratory mask assembly of claim 20, wherein the rear loop includes lower ends that are connected via a stitched joint that runs vertically relative to the horizontal plane.

23. The respiratory mask assembly of claim 1, wherein each of said first fabric layer and said second fabric layer forms an exterior surface of said first rounded lateral edge.

24. A respiratory mask system for treating a patient with sleep disordered breathing, comprising:
a respiratory mask having a mask frame;
a mask cushion provided to the frame;
a pair of upper outriggers extending from the frame and configured to pass under the patient's eyes and curve upwardly towards the patient's temples, each of the upper outriggers including an upper slot;
a pair of lower outriggers extending from the frame, the lower outriggers being shorter than the upper outriggers; and
a headgear system to hold the respiratory mask in a position on a face of a patient to enhance sealing of the cushion with the patient's face, the headgear system including a plurality of straps for attachment with the mask frame, said plurality of straps comprising:
a pair of upper straps each configured to extend above the patient's ear in use, each of the upper straps including loop material and an end with hook material, for adjustable attachment to a respective one of the upper slots;
a pair of lower straps angled downwardly with respect to a horizontal plane to guide the lower straps below the patient's ear in use, each of the lower straps including loop material and an end with hook material for adjustable attachment to a respective one of said lower outriggers; and
a rear strap portion having a rear loop configured and dimensioned to circumscribe the rear of the patient's head, the upper straps and the lower straps being attached to the rear strap portion,
wherein each of the upper straps and the lower straps is constructed from a laminate having at least a first layer and a second layer, said first layer being constructed and arranged to be located on a patient-contacting side in use, and said second layer being constructed and arranged to be located on a non patient-contacting side in use, and further wherein each of said first layer and said second layer jointly forms a part of an exposed surface having at least one rounded lateral edge when viewed in cross-section, such that the first layer forms part of the exposed surface and the second layer forms part of the exposed surface.

25. The respiratory mask system of claim 24, further comprising a joint located along mutual edges of the first and second layers.

26. The respiratory mask system of claim 25, wherein the joint is positioned at approximately a center or middle of the at least one rounded lateral edge when viewed in cross section.

27. The respiratory mask system of claim 24, wherein the laminate comprises a layer of rigid or resilient material between the first layer and the second layer.

28. The respiratory mask system of claim 24, wherein the laminate comprises a layer of semi-rigid material between the first and the second layer.

29. The respiratory mask system of claim 24, wherein the laminate further comprises a foam layer.

30. The respiratory mask system of claim 29, wherein said foam layer is encapsulated between said first layer and said second layer.

31. The respiratory mask system of claim 24, wherein the plurality of straps further comprises a stretch portion and a portion configured not to stretch.

32. The respiratory mask system of claim 24, wherein the rear loop comprises a first strap being configured to engage a back of a patient's head in a substantially circular or oval shape, the first strap having at least a portion that is substantially inextensible.

33. The respiratory mask system of claim 24, wherein the rear loop comprises a rear loop of straps configured to circumscribe the rear of the patient's head, the rear loop being substantially inextensible along its length.

34. The respiratory mask system of claim 24, wherein the rear strap portion comprises a substantially inextensible arcuate region constructed to resiliently return to a predetermined three dimensional shape substantially matching its in-use configuration when not in use.

35. The respiratory mask system of claim 24, wherein the rear strap portion comprises a substantially inextensible rear portion that is configured to be located at the upper half of the patient's head while in use.

36. The respiratory mask system of claim 24, wherein the rear strap portion is configured to engage a back of a patient's head and extend on either side of the patient's parietal bone behind the patient's ears and assume, in use, a substantially circular or oval shape.

37. The respiratory mask system of claim 24, wherein the plurality of straps comprises a portion that is configured to maintain a three dimensional shape when not in use so that a shape of the rear strap portion of the headgear system is curved substantially like the rear portion of the patient's head.

38. The respiratory mask system of claim 24, further comprising a stiffened region that provides the headgear system with a three dimensional shape that substantially matches a shape of a portion of the patient's head when not in use.

39. The respiratory mask system of claim 24, wherein said plurality of straps comprises a crown strap.

40. The respiratory mask system of claim 39, wherein the crown strap is configured to lie flat on the crown of a patient's head in use.

41. The respiratory mask system of claim 24, wherein the rear strap portion is configured to lie flat on the rear of a patient's head in use.

42. The respiratory mask system of claim 24,
wherein the first and second layers have abutting edges that define a joint positioned at approximately a center or middle of the at least one rounded lateral edge when viewed in cross section;
wherein the laminate further comprises a foam layer;
wherein said foam layer is substantively between said first layer and said second layer;
wherein the rear loop includes one or more straps dimensioned to circumscribe the rear of the head, at least a portion of the rear loop being substantially inextensible along its length;
wherein the rear strap portion comprises an arcuate region constructed to resiliently return to a predetermined three dimensional shape that substantially matches a shape of a rear portion of the patient's head when not in use, wherein the arcuate region springs out into substantially its in-use configuration; and
wherein the first and second layers form a substantially continuous convex terminal end of the at least one lateral edge, and the joint is substantially continuous with the substantially continuous convex terminal end.

43. A respiratory mask for treating a patient with sleep-disordered breathing, comprising:
a mask frame;
a mask cushion to seal with the patient's face, and
a plurality of straps comprising:
a pair of upper straps each configured to extend above the patient's ear in use, each said upper strap including an outwardly facing loop material layer and an end with hook material to adjustably engage the outwardly facing loop material layer, for length-adjustable attachment to the mask frame;
a pair of lower straps each angled downwards relative to a horizontal plane to extend below the patient's ear in use, each said lower strap including an outwardly facing loop material layer and an end with hook material to adjustably engage the outwardly facing loop material layer, for length-adjustable attachment with a lower part of the mask; and
a rear strap portion having a rear loop configured and dimensioned to circumscribe the rear of the patient's head, each said lower strap being attached to the rear strap portion, wherein the rear strap portion, when not in use, is structured to spring into a predetermined three dimensional curved shape similar to the curved shape the headgear assumes when being worn by the patient;
wherein each of said upper strap and each said lower strap is constructed from at least a patient-contacting fabric material layer and a respective said outwardly facing loop material layer, each said patient-contacting fabric material layer being constructed and arranged to engage the patient's face while in use, and further wherein edges of the patient-contacting fabric material layer and said outwardly facing loop material layer form a joint positioned, as seen in cross-section, at a lateral edge of each said upper strap and each said lower strap.

44. The respiratory mask of claim 43, wherein each said lateral edge includes a rounded or tapered portion including a part of the patient-contacting fabric material layer and a part of the outwardly facing loop material layer.

45. The respiratory mask of claim 44, wherein each said joint is positioned at approximately a center or middle of said rounded or tapered portion when viewed in cross section.

46. The respiratory mask of claim 43, wherein each upper strap and each lower strap comprises a layer of rigid or resilient material between the patient-contacting fabric material layer and the outwardly facing loop material layer.

47. The respiratory mask of claim 43, further comprising a semi-rigid material layer between the patient-contacting fabric material layer and the outwardly facing loop material layer.

48. The respiratory mask of claim 43, further comprising a foam material layer for each said upper strap and each said lower strap.

49. The respiratory mask of claim 48, wherein said foam material layer is between each said patient-contacting fabric material layer and a respective said outwardly facing loop material layer.

50. The respiratory mask of claim 43, wherein the plurality of straps further comprises a stretch portion and a portion configured not to stretch.

51. The respiratory mask of claim 43, wherein the rear loop comprises a first strap being configured to engage a back of a patient's head in a substantially circular or oval shape, the first strap having at least a portion that is substantially inextensible.

52. The respiratory mask of claim 43, wherein the rear loop comprises a rear loop of straps configured to circumscribe the rear of the patient's head, the rear loop being substantially inextensible along its length, and each said upper strap being substantially extensible along its length.

53. The respiratory mask of claim 43, wherein the rear strap portion comprises a substantially inextensible arcuate region constructed to resiliently return to the predetermined three dimensional curved shape when not in use.

54. The respiratory mask of claim 43, wherein the rear strap portion comprises a relatively inextensible rear portion that is configured to be located at the upper half of the patient's head while in use.

55. The respiratory mask of claim 43, wherein the rear strap portion is configured to engage a back of a patient's head and extend on either side of the patient's parietal bone behind the patient's ears and assume, in use, a substantially circular or oval shape.

56. The respiratory mask of claim 43, wherein the three dimensional curved shape is a dome shape.

57. The respiratory mask of claim 43, further comprising a stiffened region that provides the rear loop with the three dimensional curved shape when not in use.

58. The respiratory mask of claim 43, wherein said plurality of straps comprises a crown strap.

59. The respiratory mask of claim 58, wherein the crown strap is configured to lie flat on the crown of a patient's head in use.

60. The respiratory mask of claim 43, wherein the rear strap portion is configured to lie flat on the rear of a patient's head in use.

61. The respiratory mask of claim 43,
wherein each said lateral edge includes a rounded or tapered portion including a part of the patient-contacting fabric material layer and a part of the outwardly facing loop material layer;
wherein each said joint is positioned at approximately a center or middle of said rounded or tapered portion when viewed in cross section;
wherein a foam material layer is between said patient-contacting fabric material layer and said outwardly facing loop material layer;
wherein the rear loop comprises a rear loop of straps configured to circumscribe the rear of the patient's head, the rear loop being substantially inextensible along its length and each said upper strap being substantially extensible along its length;

wherein the rear strap portion comprises a substantially inextensible arcuate region constructed to resiliently return to the predetermined three dimensional curved shape when not in use;

wherein the rear strap portion is configured to engage a back of a patient's head and extend on either side of the patient's parietal bone behind the patient's ears, in use, wherein the plurality of straps comprises a portion that is configured to be relatively self-supporting such that the rear loop maintains the three dimensional curved shape that is pre-formed in the curved shape it is intended to be worn when not in use;

wherein the upper straps have a first extensibility and the lower straps have a different extensibility; and wherein the rear strap portion is configured to lie flat on the rear of a patient's head in use.

* * * * *